(12) United States Patent
Olofsson et al.

(10) Patent No.: US 7,705,023 B2
(45) Date of Patent: Apr. 27, 2010

(54) INDOLES USEFUL IN THE TREATMENT OF INFLAMMATION

(75) Inventors: Kristofer Olofsson, Solna (SE); Benjamin Pelcman, Solna (SE); Ivars Kalvins, Riga (LV); Edgars Suna, Riga (LV); Vita Ozola, Riga (LV); Martins Katkevics, Riga (LV)

(73) Assignee: Biolipox AB, Solna (SE)

( * ) Notice: Subject to any disclaimer, the term of this patent is extended or adjusted under 35 U.S.C. 154(b) by 0 days.

(21) Appl. No.: 11/629,624

(22) PCT Filed: Jun. 17, 2005

(86) PCT No.: PCT/GB2005/002391

§ 371 (c)(1),
(2), (4) Date: Aug. 15, 2007

(87) PCT Pub. No.: WO2005/123673

PCT Pub. Date: Dec. 29, 2005

(65) Prior Publication Data

US 2007/0287715 A1    Dec. 13, 2007

(51) Int. Cl.
| A61K 31/404 | (2006.01) |
| A61K 31/44 | (2006.01) |
| A61K 31/497 | (2006.01) |
| A61P 29/00 | (2006.01) |
| C07D 209/32 | (2006.01) |
| C07D 401/02 | (2006.01) |

(52) U.S. Cl. .................. 514/339; 514/416; 514/254.09; 514/256; 514/314; 514/318; 514/333; 514/419; 544/333; 544/373; 546/167; 546/193; 546/256; 546/278.1; 548/465; 548/483; 548/492

(58) Field of Classification Search .................. 514/339, 514/420; 546/278.1; 548/466, 483
See application file for complete search history.

(56) References Cited

U.S. PATENT DOCUMENTS

| 4,960,786 | A | 10/1990 | Salituro et al. | |
|---|---|---|---|---|
| 5,081,138 | A | 1/1992 | Gillard et al. | |
| 5,081,145 | A | 1/1992 | Guindon et al. | |
| 5,189,054 | A | 2/1993 | Salituro et al. | |
| 5,236,916 | A | 8/1993 | Weller, III et al. | 514/229.2 |
| 5,294,722 | A | 3/1994 | Kim | 548/251 |
| 5,374,615 | A | 12/1994 | Poss | 514/3.81 |
| 5,399,559 | A | 3/1995 | Curtze et al. | |
| 6,075,037 | A | 6/2000 | Elliott et al. | |
| 6,288,103 | B1 | 9/2001 | Faull et al. | |
| 6,337,344 | B1 | 1/2002 | Defossa et al. | |
| 6,353,007 | B1 | 3/2002 | Sharma | 514/339 |
| 6,441,004 | B1 | 8/2002 | Faull et al. | |
| 6,479,527 | B1 | 11/2002 | Barker et al. | |
| 6,500,853 | B1 | 12/2002 | Seehra et al. | |
| 6,569,888 | B1 | 5/2003 | Kettle et al. | |
| 6,613,760 | B1 | 9/2003 | Kettle et al. | |
| 6,630,496 | B1 | 10/2003 | Seehra et al. | |
| 6,787,651 | B2 | 9/2004 | Stolle et al. | |
| 6,828,344 | B1 | 12/2004 | Seehra et al. | |
| 6,833,387 | B1 | 12/2004 | Faull et al. | |
| 6,916,841 | B2 | 7/2005 | Seehra et al. | |
| 2003/0119830 | A1 | 6/2003 | Faull et al. | 514/232.8 |
| 2008/0249091 | A1* | 10/2008 | Pelcman et al. | 514/235.2 |

FOREIGN PATENT DOCUMENTS

| EP | 0 166 491 A2 | 1/1986 |
| EP | 0 275 667 A1 | 7/1988 |
| EP | 0 429 257 A2 | 5/1991 |
| EP | 0 275 667 B1 | 3/1992 |
| EP | 488 532 | 6/1992 |
| EP | 186 367 B1 | 3/1993 |
| EP | 0 535 924 A1 | 4/1993 |
| EP | 547 556 A1 | 6/1993 |
| EP | 986 666 | 12/1993 |
| EP | 0 639 573 A1 | 2/1995 |
| EP | 0 643 695 B1 | 8/1996 |
| EP | 0 483 881 B1 | 1/1998 |
| EP | 1 056 719 | 9/1999 |
| EP | 1 173 421 | 8/2000 |
| EP | 0 633 886 B1 | 10/2000 |
| EP | 1 159 269 B1 | 3/2003 |
| EP | 1 314 733 A1 | 5/2003 |
| EP | 1 003 504 B1 | 7/2003 |
| EP | 1 150 953 B1 | 9/2003 |
| EP | 1 042 287 B1 | 4/2005 |

(Continued)

OTHER PUBLICATIONS

STN search report-U.S. Appl. No. 11/629,624.*

(Continued)

*Primary Examiner*—Yong Chu
(74) *Attorney, Agent, or Firm*—Morgan Lewis & Bockius LLP

(57) ABSTRACT

There is provided a compound of formula: (I), wherein X, $R^1$, $R^2$, $R^3$, $R^4$, $R^5$ and $R^6$ have meanings given in the description, and pharmaceutically-acceptable salts thereof, which compounds are useful in the treatment of diseases in which inhibition of the activity of microsomal prostaglandin E synthase-1 is desired and/or required, and particularly in the treatment of inflammation.

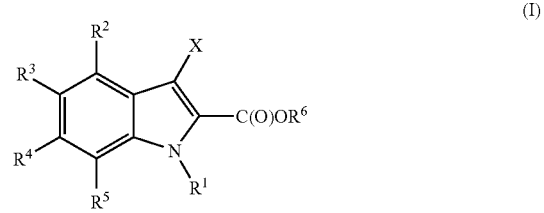

(I)

31 Claims, No Drawings

FOREIGN PATENT DOCUMENTS

| | | |
|---|---|---|
| WO | WO 93/25524 A1 | 12/1993 |
| WO | WO 93/25546 A1 | 12/1993 |
| WO | WO 94/13662 A1 | 6/1994 |
| WO | WO 94/14434 A1 | 7/1994 |
| WO | WO 95/33748 A1 | 12/1995 |
| WO | WO 96/03377 A1 | 2/1996 |
| WO | WO 96/18393 A1 | 6/1996 |
| WO | WO 98/08818 A1 | 3/1998 |
| WO | WO 99/05104 | 2/1999 |
| WO | WO 99/07351 A2 | 2/1999 |
| WO | WO 99/07678 A1 | 2/1999 |
| WO | WO 99/15501 | 4/1999 |
| WO | WO 99/33800 A1 | 7/1999 |
| WO | WO 99/40914 A1 | 8/1999 |
| WO | WO 99/43434 A1 | 9/1999 |
| WO | WO 99/43651 A2 | 9/1999 |
| WO | WO 99/43654 A2 | 9/1999 |
| WO | WO 99/43672 A1 | 9/1999 |
| WO | WO 00/46195 | 8/2000 |
| WO | WO 00/46195 A1 | 8/2000 |
| WO | WO 00/46197 A1 | 8/2000 |
| WO | WO 00/46198 A1 | 8/2000 |
| WO | WO 00/46199 A2 | 8/2000 |
| WO | WO 01/00197 A2 | 1/2001 |
| WO | WO 01/30343 A1 | 5/2001 |
| WO | WO 01/32621 A1 | 5/2001 |
| WO | WO 02/06273 | 1/2002 |
| WO | WO 02/30895 A1 | 4/2002 |
| WO | WO 03/029212 | 4/2003 |
| WO | WO 03/044014 | 5/2003 |
| WO | WO 03/057670 | 7/2003 |
| WO | WO 2004/022537 | 3/2004 |
| WO | WO 2005/005415 | 1/2005 |
| WO | WO 2005/123673 | 12/2005 |
| WO | WO 2005/123674 | 12/2005 |
| WO | WO 2006/123675 | 12/2005 |

OTHER PUBLICATIONS

Rajur et al., Indian Journal of Chemistry, vol. 31B, 1992, p. 551-554. This reference was disclosed in IDS.*

Rajur, Sharanabasava B., et al.: "Attempted Synthesis of 9-Substituted 3-Amino-7Methyl (or Phenyl)-5, 6-Dihydroindolo '1, 2-a!quinoxalines as Possible Antiallergic Agents" Indian Journal of Chemistry, Section B: Organic Chemistry Including Medicinal Chemistry, 31B98), 551-554, (1992).

Rajur, S.B., et al., "Attempted synthesis of 9-substituted 34-amino-7-methyl (or phenyl)-5,6-dihydroindolo[1,2-α]quinoxalines as possible antiallergic agents", Indian Journal of Chemistry Section B; Organic Chemistry Including Medicinal Chemistry; 31B:551-554 (1992).

Rajur, S.B., et al., "Attempted synthesis of 9-substituted 34-amino-7-methyl (or phenyl)-5,6-dihydroindolo[1,2-α]quinoxalines as possible antiallergic agents", Indian Journal of Chemistry Section B; Organic Chemistry Including Medicinal Chemistry; 31B:551-554 (1992).

Roy, P.J., et al., "The Hemetsberger-Knitted Synthesis of Substituted 5-, 6-, and 7-Azaindoles", Synthesis, 16:2751-2757(2005).

Lachance, N., et at, "Rapid and Efficient Microwave-Assisted Synthesis of 4-, 5-, 6- and 7-Azaindoles", Synthesis, 15:2571-2577 (2005).

Dropinski, J.F., et al., "Synthesis and biological activities of novel aryl indole-2-carboxylic acid analogs as PPARγ partial agonists", Bioorganic & Medicinal Chemistry Letters, 15:5035-5038 (2005).

Sornmen, G., et at, "Preparation of thieno[2,3-*b*]pyrroles starting from ketene-*N,S*-acetals", Tetrahedron, 59:1557-1564 (2003).

Sommen, G., et al., "An Easy Access to Variously Substituted Thieno[2,3-*b*]pyrroles by Using Isothiocyanates", Synlett., 11(10):1731-1734 (2001).

El Hamed, M.K.A., et al., "Synthesis of Some Fused Thienopyrimidine Derivatives of Potential Antimicrobial Activity", Bulletin of the Faculty of Pharmacy (Cairo University), 39(3):11-21 (2001).

El-Shafei, A.K., et al., "Synthesis of Thienol(2,3-b) Thiophenes and Related Structures", Phosphorus, Sulfur and Silicon and the Related Elements, 73:15-25 (1992).

Kumar, P.R., et al., "Synthesis and biological evaluation of thiopene [3,2-*b*] pyrrole derivatives as potential anti-inflammatory agents", Bioorganic & Medicinal Chemistry, 12:1221-1230 (2004).

* cited by examiner

INDOLES USEFUL IN THE TREATMENT OF INFLAMMATION

FIELD OF THE INVENTION

This invention relates to novel pharmaceutically-useful compounds, which compounds are useful as inhibitors of enzymes belonging to the membrane-associated proteins in the eicosanoid and glutathione metabolism (MAPEG) family. Members of the MAPEG family include the microsomal prostaglandin E synthase-1 (mPGES-1), 5-lipoxygenase-activating protein (FLAP), leukotriene $C_4$ synthase and microsomal glutathione S-transferases (MGST1, MGST2 and MGST3). The compounds are of potential utility in the treatment of inflammatory diseases including respiratory diseases. The invention also relates to the use of such compounds as medicaments, to pharmaceutical compositions containing them, and to synthetic routes for their production

BACKGROUND OF THE INVENTION

There are many diseases/disorders that are inflammatory in their nature. One of the major problems associated with existing treatments of inflammatory conditions is a lack of efficacy and/or the prevalence of side effects (real or perceived).

Inflammatory diseases that affect the population include asthma, inflammatory bowel disease, rheumatoid arthritis, osteoarthritis, rhinitis, conjunctivitis and dermatitis.

Inflammation is also a common cause of pain. Inflammatory pain may arise for numerous reasons, such as infection, surgery or other trauma. Moreover, several diseases including malignancies and cardioavascular diseases are known to have inflammatory components adding to the symptomatology of the patients.

Asthma is a disease of the airways that contains elements of both inflammation and bronchoconstriction. Treatment regimens for asthma are based on the severity of the condition. Mild cases are either untreated or are only treated with inhaled β-agonists which affect the bronchoconstriction element, whereas patients with more severe asthma typically are treated regularly with inhaled corticosteroids which to a large extent are anti-inflammatory in their nature.

Another common disease of the airways with inflammatory and bronchoconstrictive components is chronic obstructive pulmonary disease (COPD). The disease is potentially lethal, and the morbidity and mortality from the condition is considerable. At present, there is no known pharmacological treatment capable of changing the course of the disease.

The cyclooxygenase (COX) enzyme exists in two forms, one that is constitutively expressed in many cells and tissues (COX-1), and one that is induced by pro-inflammatory stimuli, such as cytokines, during an inflammatory response (COX-2).

COXs metabolise arachidonic acid to the unstable intermediate prostaglandin $H_2$ ($PGH_2$). $PGH_2$ is further metabolised to other prostaglandins including $PGE_2$, $PGF_{2\alpha}$, $PGD_2$, prostacyclin and thromboxane $A_2$. These arachidonic acid metabolites are known to have pronounced physiological and pathophysiological activity including pro-inflammatory effects.

$PGE_2$ in particular is known to be a strong pro-inflammatory mediator, and is also known to induce fever and pain. Consequently, numerous drugs have been developed with a view to inhibiting the formation of $PGE_2$, including "NSAIDs" (non-steroidal antiinflammatory drugs) and "coxibs" (selective COX-2 inhibitors). These drugs act predominantly by inhibition of COX-1 and/or COX-2, thereby reducing the formation of $PGE_2$.

However, the inhibition of COXs has the disadvantage that it results in the reduction of the formation of all metabolites of arachidonic acid, some of which are known to have beneficial properties. In view of this, drugs which act by inhibition of COXs are therefore known/suspected to cause adverse biological effects. For example, the non-selective inhibition of COXs by NSAIDs may give rise to gastrointestinal side-effects and affect platelet and renal function. Even the selective inhibition of COX-2 by coxibs, whilst reducing such gastrointestinal side-effects, is believed to give rise to cardiovascular problems.

An alternative treatment of inflammatory diseases that does not give rise to the above-mentioned side effects would thus be of real benefit in the clinic. In particular, a drug that inhibits (preferably selectively) the transformation of $PGH_2$ to the pro-inflammatory mediator $PGE_2$ might be expected to reduce the inflammatory response in the absence of a corresponding reduction of the formation of other, beneficial arachidoric acid metabolites. Such inhibition would accordingly be expected to alleviate the undesirable side-effects mentioned above.

$PGH_2$ may be transformed to $PGE_2$ by prostaglandin E synthases (PGES). Two microsomal prostaglandin E synthases (mPGES-1 and mPGES-2), and one cytosolic prostaglandin E synthase (cPGES) have been described.

The leukotrienes (LTs) are formed from arachidonic acid by a set of enzymes distinct from those in the COX/PGES pathway. Leukotriene B4 is known to be a strong proinflammatory mediator, while the cysteinyl-containing leukotrienes $C_4$, $D_4$ and $E_4$ (CysLTs) are mainly very potent bronchoconstrictors and have thus been implicated in the pathobiology of asthma. The biological activities of the CysLTs are mediated through two receptors designated $CysLT_1$ and $CysLT_1$. As an alternative to steroids, leukotriene receptor antagonists (LTRas) have been developed in the treatment of asthma. These drugs may be given orally, but do not control inflammation satisfactorily. The presently used LTRas are highly selective for $CysLT_1$. It may be hypothesised that better control of asthma, and possibly also COPD, may be attained if the activity of both of the CysLT receptors could be reduced. This may be achieved by developing unselective LTRas, but also by inhibiting the activity of proteins, e.g. enzymes, involved in the synthesis of the CysLTs. Among these proteins, 5-lipoxygenase, 5-lipoxygenase-activating protein (FLAP), and leukotriene $C_4$ synthase may be mentioned. A FLAP inhibitor would also decrease the formation of the proinflammatory $LTB_4$.

mPGES-1, FLAP and leukotriene $C_4$ synthase belong to the membrane-associated proteins in the eicosanoid and glutathione metabolism (MAPEG) family. Other members of this family include the microsomal glutathione S-transferases (MGST1, MGST2 and MGST3). For a review, c.f. P.-J. Jacobsson et al in *Am. J. Respir. Crit. Care Med.* 161, S20 (2000). It is well known that compounds prepared as antagonists to one of the MAPEGs may also exhibit inhibitory activity towards other family members, cf. J. H Hutchinson et al in *J. Med. Chem.* 38, 4538 (1995) and D. Claveau et al in *J. Immunol.* 170, 4738 (2003). The former paper also describes that such compounds may also display notable cross-reactivity with proteins in the arachidonic acid cascade that do not belong to the MAPEG family, e.g. 5-lipoxygenase.

Thus, agents that are capable of inhibiting the action of mPGES-1, and thus reducing the formation of the specific arachidonic acid metabolite $PGE_2$, are likely to be of benefit in the treatment of inflammation. Further, agents that are capable of inhibiting the action of the proteins involved in the synthesis of the leukotrienes are also likely to be of benefit in the treatment of asthma and COPD.

PRIOR ART

Certain specific 1(N)-phenylindole-2-carboxylate derivatives have been disclosed by Rajur et al in *Ind. J. Chem Section B: Organic Chemistry Including Medicinal Chemistry*, 31B, 551 (1992) as chemical intermediates useful in the synthesis of antiallergic agents. The use of these intermediates in the treatment of inflammatory disorders is not suggested in this document.

Various indole-2-carboxylates, and derivatives thereof, have been disclosed in international patent applications WO 01/30343, WO 96/03377, WO 01/00197 and WO 99/33800, U.S. Pat. Nos. 5,189,054 and 4,960,786, European patent application EP 483 881 and Italian Patent No. 1303260. However, none of these documents disclose or suggest the use of the indole-2-carboxylates in the treatment of inflammation.

Similar indole-2-carboxylates have been disclosed for potential use in the treatment of inflammation in international patent applications WO 99/07678, WO 99/07351, WO 00/46198, WO 00/46197, WO 00/46195, WO 00/46199, WO 96/18393, WO 02/30895, WO 99/05104, WO 01/32621 and WO 2005/005415, U.S. Pat. Nos. 5,081,145 and 5,081,138 and European patent applications EP 166 591 and EP 985 666. However, none of these documents disclose such compounds in which an aromatic group is directly attached to the ring system via the indole nitrogen.

International patent application WO 94/13662 and European patent application EP 186 367 also mention indoles for potential use in the treatment of inflammation. However, these documents do not mention or suggest compounds in which the benzenoid moiety of the indole is substituted with an aromatic ring.

International patent applications WO 94/14434, WO 99/43672, WO 98/08818, WO 99/43654 and WO 99/43651 and U.S. Pat. Nos. 6,500,853 and 6,630,496 also describe structurally similar indoles for such potential use. However, there is no specific disclosure in any of these documents of indole-2-carboxylates in which an aromatic group is directly attached via the indole nitrogen.

DISCLOSURE OF THE INVENTION

According to the invention there is provided a compound of formula I,

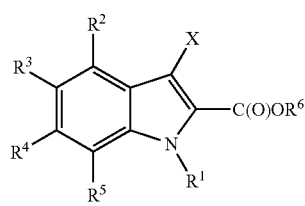

wherein

X represents H or a halo group;

$R^1$ represents an aryl group or a heteroaryl group, both of which groups are optionally substituted by one or more substituents selected from A;

one of the groups $R^2$, $R^3$, $R^4$ and $R^5$ represents an aryl group or a heteroaryl group (both of which are optionally substituted by one or more substituents selected from A) and:

a) the other groups are independently selected from hydrogen, $G^1$, an aryl group, a heteroaryl group (which latter two groups are optionally substituted by one or more substituents selected from A), $C_{1-8}$ alkyl and a heterocycloalkyl group (which latter two groups are optionally substituted by one or more substituents selected from $G^1$ and/or $Z^1$); and/or b) any two other groups which are adjacent to each other are optionally linked to form, along with two atoms of the essential benzene ring in the compound of formula I, a 3- to 8-membered ring, optionally containing 1 to 3 heteroatoms and/or 1 to 3 double bonds, which ring is itself optionally substituted by one or more substituents selected from halo, $-R^6$, $-OR^6$ and $=O$;

A represents, on each occasion when mentioned above:

I) an aryl group or a heteroaryl group, both of which are optionally substituted by one or more substituents selected from B;

II) $C_{1-8}$ alkyl or a heterocycloalkyl group, both of which are optionally substituted by one or more, substituents selected from $G^1$ and/or $Z^1$;

III) a $G^1$ group; or

IV) two A substituents may be linked together to form, along with at least two (e.g. adjacent) atoms of the aryl or heteroaryl group to which the two A substituents are attached, a further 3- to 5-membered ring, which ring optionally contains 1 to 3 (e.g. 1 or 2) hetereoatoms and/or 1 to 2 (e.g. 1) double bonds, and which is optionally substituted by halo or $C_{1-8}$ alkyl, which latter group is optionally substituted by halo;

$R^6$ represents, on each occasion when mentioned above:

I) hydrogen;

II) an aryl group or a heteroaryl group, both of which are optionally substituted by one or more substituents selected from B; or III) $C_{1-8}$ alkyl or a heterocycloalkyl group, both of which are optionally substituted by one or more substituents selected from $G^1$ and/or $Z^1$;

$G^1$ represents, on each occasion when mentioned above, halo, cyano, $-N_3$, $-NO_2$, $-ONO_2$ or $-A^1-R^7$;

wherein $A^1$ represents a single bond or a spacer group selected from $-C(O)A^2-$, $-S(O)A^3-$, $-N(R^8)A^4-$ or $-OA^5-$, in which:

$A^2$ and $A^1$ independently represent a single bond, $-O-$, $-N(R^8)-$ or $-C(O)-$;

$A^4$ and $A^5$ independently represent a single bond, $-C(O)-$, $-C(O)N(R^8)-$, $-C(O)O-$, $-S(O)-$, or $-S(O)_nN(R^8)-$;

$Z^1$ represents, on each occasion when mentioned above, $=O$, $=S$, $=NOR^7$, $=NS(O)_nN(R^8)(R^7)=NCN$ or $=C(H)NO_2$;

B represents, on each occasion when mentioned above:

I) an aryl group or a heteroaryl group, both of which are optionally substituted by one or more substituents selected from $G^2$, methylenedioxy, difluoromethylenedioxy and/or dimethylmethylenedioxy;

II) $C_{1-8}$ alkyl or a heterocycloalkyl group, both of which are optionally substituted by one or more substituents selected from $G^2$ and/or $Z^2$;

III) a $G^2$ group; or

IV) methylenedioxy, difluoromethylenedioxy or dimethylmethylenedioxy;

$G^2$ represents, on each occasion when mentioned above, halo, cyano, —$N_3$, —NO, —ONO, or -$A^6$-$R^9$;

wherein $A^6$ represents a single bond or a spacer group selected from —C(O)$A^7$-, —S(O)$_n A^8$-, —N($R^{10}$)$A^9$- or —O$A^{10}$- in which:

$A^7$ and $A^8$ independently represent a single bond, —O—, —N($R^{10}$)— or —C(O)—;

$A^9$ and $A^{10}$ independently represent a single bond, —C(O)—, —C(O)N($R^{10}$)—, —C(O)O—, —S(O)$_n$— or —S(O)$_n$N($R^{10}$)—;

$Z^2$ represents, on each occasion when mentioned above, =O, =S, =NO$R^9$, =NS(O)$_n$N($R^{10}$)($R^9$), =NCN or =C(H)NO;

$R^7$, $R^8$, $R^9$ and $R^{10}$ are independently selected from:

i) hydrogen;

ii) an aryl group or a heteroaryl group, both of which are optionally substituted by one or more substituents selected from $G^3$, methylenedioxy, difluoromethylenedioxy and/or dimethylmethylenedioxy;

iii) $C_{1-8}$ alkyl or a heterocycloalkyl group, both of which are optionally substituted by $G^3$ and/or $Z^3$; or any pair of $R^7$ and $R^8$, or $R^9$ and $R^{10}$, may, for example when present on the same or on adjacent atoms, be linked together to form with those, or other relevant, atoms a further 3- to 8-membered ring, optionally containing 1 to 3 heteroatoms and/or 1 to 3 double bonds, which ring is optionally substituted by one or more substituents selected from $G^3$ and/or $Z^3$;

$G^3$ represents, on each occasion when mentioned above, halo, cyano, —$N_3$, —$NO_2$, —$ONO_2$ or -$A^{11}$-$R^{11}$;

wherein $A^{11}$ represents a single bond or a spacer group selected from —C(O)$A^{12}$-, —S(O)$_n A^{13}$-, —N($R^{12}$)$A^{14}$- or —O$A^{15}$-, in which:

$A^{12}$ and $A^{13}$ independently represent a single bond, —O—, —N($R^{12}$)— or —C(O)—;

$A^{14}$ and $A^{15}$ independently represent a single bond, —C(O)—, —C(O)N($R^{12}$)—, —C(O)O—, —S(O)$_n$— or —S(O)$_n$N($R^{12}$)—;

$Z^3$ represents, on each occasion when mentioned above, =O, =S, =NO$R^{11}$, =NS(O)$_n$N($R^{12}$)($R^{11}$), =NCN or =C(H)NO$_2$;

n represents, on each occasion when mentioned above, 1 or 2;

$R^{11}$ and $R^{12}$ are independently selected from:

i) hydrogen;

ii) $C_{1-6}$ alkyl or a heterocycloalkyl group, both of which groups are optionally substituted by one or more substituents selected from halo, $C_{1-4}$ alkyl, —N($R^{13}$)($R^{14}$), —O($R^{13}$) and =O; and iii) an aryl or heteroaryl group, both of which are optionally substituted by one or more substituents selected from halo, $C_{1-4}$ alkyl, —N($R^{13}$)($R^{14}$) and —O($R^{13}$); or any pair $R^{11}$ and $R^{12}$ may, for example when present on the same or on adjacent atoms, be linked together to form with those, or other relevant, atoms a further 3- to 8-membered ring, optionally containing 1 to 3 heteroatoms and/or 1 to 3 double bonds, which ring is optionally substituted by one or more substituents selected from halo, $C_{1-4}$ allyl, —N($R^3$)($R^{14}$), —O($R^{13}$) and =O;

$R^{13}$ and $R^{14}$ are independently selected from hydrogen and $C_{1-4}$ alkyl, which latter group is optionally substituted by one or more halo groups;

or a pharmaceutically-acceptable salt thereof, provided that, when $R^2$, $R^4$ and $R^5$ all represent H, $R^3$ represents unsubstituted phenyl, $R^6$ represents ethyl, and X represents H or Cl, then $R^1$ does not represent 2,4-dinitrophenyl, which compounds and salts are referred to hereinafter as "the compounds of the invention".

Pharmaceutically-acceptable salts include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

Compounds of the invention may contain double bonds and may thus exist as E (entgegen) and Z (zusammen) geometric isomers about each individual double bond. All such isomers and mixtures thereof are included within the scope of the invention.

Compounds of the invention may also exhibit tautomerism. All tautomeric forms and mixtures thereof are included within the scope of the invention.

Compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person. All stereoisomers and mixtures thereof are included within the scope of the invention.

Unless otherwise specified, $C_{1-q}$ alkyl groups (where q is the upper limit of the range) defined herein may be straight-chain or, when there is a sufficient number (i.e. a minimum of two or three, as appropriate) of carbon atoms, be branched-chain and/or cyclic (so forming a $C_{3-q}$ cycloalkyl group). $C_{3-q}$ cycloalkyl groups that may be mentioned include monocyclic or bicyclic alkyl groups, which cycloalkyl groups may further be bridged. Further, when there is a sufficient number (i.e. a minimum of four) of carbon atoms, such groups may also be part cyclic. Such alkyl groups may also be saturated or, when there is a sufficient number (i.e. a minimum of two) of carbon atoms, be unsaturated (forming, for example, a $C_{3-q}$ cycloalkenyl, a $C_8$ cycloalkynyl or, more particularly, a $C_{2-q}$ alkenyl or a $C_{2-q}$ alkynyl group). Further, in the case where the substituent is another cyclic compound, then the cyclic substituent may be attached through a single atom on the cycloalkyl group, forming a so-called "spiro"-compound.

The term "halo", when used herein, includes fluoro, choro, bromo and iodo.

Heterocycloalkyl groups that may be mentioned include those in which at least one (e.g. one to four) of the atoms in the ring system is other than carbon (i.e. a heteroatom), and in which the total number of atoms in the ring system is between three and twelve (e.g. between five and ten). Further, such heterocycloalkyl groups may be saturated or unsaturated containing one or more double and/or triple bonds, forming for example a $C_{2-q}$ (e.g. $C_{3-q}$) heterocycloalkenyl (where q is the upper limit of the range) or a $C_{3-q}$ heterocycloalkynyl group. $C_{2-q}$ heterocycloalkyl groups that may be mentioned include aziridinyl, azetidinyl, dihydropyranyl, dihydropyridyl, dihydropyrrolyl (including 2,5-dihydropyrrolyl), dioxolanyl (including 1,3-dioxolanyl), dioxanyl (including 1,3-dioxanyl and 1,4-dioxanyl), dithianyl (including 1,4-dithianyl), dithiolanyl (including 1,3-dithiolanyl), imidazolidinyl, imidazolinyl, morpholinyl, oxetanyl, oxiranyl, piperazinyl, piperidinyl, pyranyl, pyrazolidinyl, pyrrolidinonyl, pyrrolidinyl, pyrrolinyl, quinuclidinyl, sulfolanyl, 3-sulfolenyl, tetrahydropyranyl, tetrahydrofuranyl, tetrahydropyridyl, thietanyl, thiiranyl, thiolanyl, thiomorpholinyl, trithianyl (including 1,3,5-trithianyl), tropanyl and the like. Other heterocycloalkyl groups that may be mentioned include 7-azabicyclo[2.2.1]heptanyl, 6-azabicyclo[3.1.1]heptanyl, 6-azabicyclo-[3.2.1]octanyl, 8-azabicyclo[3.2.1]-octanyl, 7-oxabicyclo[2.2.1]heptanyl and 6-oxabicyclo[3.2.1]octanyl. Heterocycloalkyl groups that may be mentioned include monocyclic and bicyclic heterocycloalkyl groups, which groups may further be bridged. Substituents on heterocycloalkyl groups may, where appropriate, be located on any atom in the ring system including a heteroatom. Further, ill the case where the other substituent is another cyclic compound, then the cyclic compound may be attached through a single atom on the heterocycloalkyl group, forming a so-called "spiro"-compound. The point of attachment of heterocycloalkyl groups may be via any atom in the ring system including (where appropriate) a heteroatom (such as a nitrogen atom), or an atom on any fused carbocyclic ring that may be present as part of the ring system. Heterocycloalkyl groups may also be in the N- or S-oxidised form.

For the avoidance of doubt, the term "bicyclic", when employed in the context of cycloalkyl and heterocycloalkyl groups refers to such groups in which the second ring is formed between two adjacent atoms of the first ring. The term "bridged", when employed in the context of cycloalkyl or heterocycloalkyl groups refers to monocyclic or bicyclic groups in which two non-adjacent atoms are linked by either an alkylene or heteroalkylene chain (as appropriate).

Aryl groups that may be mentioned include $C_{6-13}$ (e.g. $C_{6-10}$) aryl groups. Such groups may be monocyclic or bicyclic and have between 6 and 13 (e.g. 10) ring carbon atoms, in which at least one ring is aromatic. $C_{6-13}$ aryl groups include phenyl, naphthyl and the like, such as fluorenyl and, more particularly, 1,2,3,4-tetrahydronaphthyl, indanyl, and indenyl. The point of attachment of aryl groups may be via any atom of the ring system. However, when aryl groups are bicyclic or tricyclic, they are preferably linked to the rest of the molecule via an aromatic ring.

Heteroaryl groups that may be mentioned include those which have between 5 and 10 members. Such groups may be monocyclic, bicyclic or tricyclic, provided that at least one of the rings is aromatic and wherein at least one (e.g. one to four) of the atoms in the ring system is other than carbon (i.e. a heteroatom). Heterocyclic groups that may be mentioned include acridinyl, benzimidazolyl, benzodioxanyl, benzodioxepinyl, benzodioxolyl (including 1,3-benzodioxolyl), benzofuranyl, benzofurazanyl, benzothiazolyl (including 2,1,3-benzothiazolyl), benzoxadiazolyl (including 2,1,3-benzoxadiazolyl), benzoxazinyl (including 3,4-dihydro-2H-1,4-benzoxazinyl), benzoxazolyl, benzimidazolyl, benzomorpholinyl, benzoselenadiazolyl (including 2,1,3-benzoselenadiazolyl), benzothienyl, carbazolyl, chromanyl, cinnolinyl, furanyl, imidazolyl, imidazo[1,2-a]pyrridyl, indazoyl, indolinyl, indolyl, isobenzofuranyl, isochromanyl, isoindolinyl, isoindolyl, isoquinolinyl, isothiaziolyl, isoxazolyl, naphthyridinyl (including 1,5-naphthyridinyl and 1,8-naphthyridinyl), oxadiazolyl (including 1,2,3-oxadiazolyl, 1,2,4-oxadiazolyl and 1,3,4-oxadiazolyl), oxazolyl, phenazinyl, phenothiazinyl, phthalazinyl, pteridinyl, purinyl, pyrazinyl, pyrazolyl, pyridazinyl, pyridyl, pyrimidinyl, pyrrolyl, quinazolinyl, quinolinyl, quinolizinyl, quinoxalinyl, tetrahydroiso-quinolinyl (including 1,2,3,4-tetrahydroiso-quinlolinyl and 5,6,7,8-tetrahydroisoquinolinyl), tetrahydroquinolinyl (including 1,2,3,4-tetrahydroquinolinyl and 5,6,7,8-tetrahydroquinolinyl), tetrazolyl, thiadiazolyl (including 1,2,3-thiadiazolyl, 1,2,4-thiadiazolyl and 1,3,4-thiadiazolyl), thiazolyl, thiochromanyl, thienyl, triazolyl (including 1,2,3-triazolyl, 1,2,4-triazolyl and 1,3,4-triazolyl) and the like. Substituents on heteroaryl groups may, where appropriate, be located on any atom in the ring system including a heteroatom. The point of attachment of heteroaryl groups may be via any atom in the ring system including (where appropriate) a heteroatom (such as a nitrogen atom), or an atom on any fused carbocyclic ring that may be present as part of the ring system. However, when heteroaryl groups are bicyclic or tricyclic, they are preferably linked to the rest of the molecule via an aromatic ring. Heteroaryl groups may also be in the N- or S-oxidised form.

Heteroatoms that may be mentioned include phosphorus, silicon, boron, tellurium, preferably, selenium and, more preferably oxygen, nitrogen and/or sulfur.

For the avoidance of doubt, optionally substituted methylenedioxy groups, when attached to a ring system are formed between any two adjacent atoms of the ring system.

For the avoidance of doubt, in cases in which the identity of two or more substituents in a compound of the invention may be the same, the actual identities of the respective substituents are not in any way interdependent. For example, in the situation in which $R^1$, and any one of $R^2$ to $R^5$, both represent aryl groups substituted by one or more $C_{1-8}$ alkyl groups, the alkyl groups in question may be the same or different. Similarly, when groups are substituted by more than one substituent as defined herein, the identities of those individual substituents are not to be regarded as being interdependent. For example, when $R^1$ represents e.g. an aryl group substituted by $G^1$ in addition to, for example, $C_{1-8}$ alkyl, which latter group is substituted by $G^1$, the identities of the two $G^1$ groups are not to be regarded as being interdependent.

Compounds of the invention that may be mentioned include those hereinbefore defined, in which, when $R^1$ represents phenol substituted by one or more (e.g. two) A groups and A represents $G^1$, then:

i) $G^1$ represents halo, cyano, —$N_3$, $ONO_2$ or -$A^1$-$R^7$; and/or ii) when $G^1$ represents —$NO_2$, then $R^6$ represents:
   I) hydrogen;
   II) an aryl group or a heteroaryl group, both of which are optionally substituted by one or more substituents selected from B; or
   III) methyl, $C_{3-8}$ alkyl or a heterocycloalkyl group, all of which are optionally substituted by one or more substituents selected from $G^1$ and/or $Z^1$.

Further compounds of the invention that may be mentioned include those in which:

$A^2$ and $A^3$ independently represent a single bond, —O— or —N($R^8$)—;

$Z^1$ represents, on each occasion ashen mentioned above, =O, =NOR$^7$, =NS(O)$_n$N($R^8$)($R^7$), =NCN or =C(H)NO$_2$;

$A^7$ and $A^8$ independently represent a single bond, —O— or —N($R^{10}$)—;

$Z^2$ represents, on each occasion when mentioned above, =O, =NOR$^9$, =NS(O)$_n$N($R^{10}$)($R^9$), =NCN or =C(H)NO$_2$;

$A^{12}$ and $A^{13}$ independently represent a single bond, —O— or —N($R^{12}$)—; and/or $Z^3$ represents, on each occasion when mentioned above, =O, =NOR$^{11}$, =NS(O)$_n$N($R^{12}$)($R^{11}$), =NCN or =C(H)NO$_2$.

Preferred compounds of the invention include those in which:

$G^1$ represents halo, cyano, —$N_3$, —$NO_2$ or -$A^1$-$R^7$;

$A^4$ and $A^5$ independently represent a single bond, —C(O)—, —C(O)N($R^8$)— or —C(O)O—;

$Z^1$ represents NOR$^7$, =NCN or, preferably, =O;

$G^2$ represents cyano, —$N_3$ or, more preferably, halo, —$NO_2$ or -$A^6$-$R^9$;

$A^6$ represents —N($R^{10}$)$A^9$- or —OA$^{10}$-;

$A^9$ represents —C(O)N($R^{10}$)—, —C(O)O— or, more preferably, a single bond or —C(O)—;

$A^{10}$ represents $A^9$ and, preferably, a single bond;

$Z^2$ represents =NOR$^9$ or =NCN or, more preferably, =O;

$G^3$ represents halo, —$NO_2$ or -$A^{11}$-$R^{11}$;

$A^{11}$ represents a single bond, —C(O)$A^{12}$, —N($R^{12}$)$A^{14}$ or —OA$^{15}$;

$A^{12}$ represents a single bond or —O—;

$A^{14}$ and $A^{15}$ independently represent —C(O)— or, more preferably, a single bond;

$Z^3$ represents =O;

n represents 2;

when either of $R^{11}$ and $R^{12}$ represent optionally substituted $C_{1-6}$ alkyl, the optional substituent is one or more halo groups;

when either of $R^{13}$ and $R^{14}$ represent optionally substituted $C_{1-4}$ alkyl, the optional substituent is one or more fluoro groups.

Preferred compounds of the invention include those in which $R^1$ and (when they represent an aryl or heteroaryl group) $R^2$, $R^3$, $R^4$ and/or $R^5$ represent an optionally substituted phenyl, naphthyl, pyrrolyl, furanyl, thienyl, pyrazolyl, imidazolyl (e.g 1-imidazolyl, 2-imidazolyl or 4-imidazolyl), oxazolyl, isoxazolyl, thiazolyl, pyridyl (e.g. 2-pyridyl, 3-pyridyl or 4-pyridyl), indazolyl, indolyl, indolinyl, isoindolinyl, quinolinyl, 1,2,3,4-tetrahydroquinolinyl, isoquinolinyl, 1,2,3,4-tetrahydroisoquinolinyl, quinolizinyl, benzofuranyl, isobenzofuranyl, chromanyl, benzothienyl, pyridazinyl, pyrimidinyl, pyrazinyl, indazolyl, benzimidazolyl, quinazolinyl, quinoxalinyl, 1,3-benzodioxolyl, benzothiazolyl, and/or benzodioxanyl, group. Other groups that may be mentioned include optionally substituted 5,6,7,8-tetrahydroquinolinyl, 5,6,7,8-tetrahydroisoquinolinyl and tetrazolyl. Particularly preferred values include optionally substituted quinolinyl and pyrimidinyl and, more particularly, phenyl, naphthyl and pyridyl.

Optional substituents on such $R^1$, $R^2$, $R^3$, $R^4$ and $R^5$ groups are preferably selected from:

cyano;

—C(O)N($R^{15}$)$R^{16}$;

heterocycloalkyl, such as a nitrogen-containing 4- to 8-membered (e.g. 5- to 6-membered) heterocycloalkyl group, optionally containing one or more unsaturations and optionally substituted by one or more halo or $C_{1-3}$ alkyl groups;

heteroaryl, such as a 5- or 6-membered nitrogen-containing heteroaryl group, optionally substituted by one or more halo or $C_{1-3}$ alkyl groups; or are more preferably selected from:

—$NO_2$;

halo (e.g. fluoro, chmoro or bromo);

$C_{1-6}$ alkyl, which alkyl group may be linear or branched (e.g. $C_{1-4}$ alkyl (including methyl, ethyl, n-propyl, isopropyl, n-butyl, isobutyl or t-butyl), n-pentyl, isopentyl, n-hexyl or isohexyl), cyclic (e.g. cyclopropyl, cyclobutyl, cyclopentyl or cyclohexyl), part-cyclic (e.g. cyclobutylmethyl or cyclopropylmethyl), unsaturated (e.g. ethylene, 1-propenyl, 2-propenyl, 1-butenyl, 2-butenyl, 3-butenyl, 1-pentenyl, 2-pentenyl, 4-pentenyl or 5-hexenyl) and/or optionally substituted with one or more groups selected from halo (e.g. fluoro, so forming fluoromethyl, difluoromethyl or trifluoromethyl), —C(O)OR$^{15}$ and —OR$^{15}$;

—OR$^{15}$;

—N($R^{15}$)$R^{16}$; and

—S(O)$_2$R$^{15}$;

wherein $R^{15}$ and $R^{16}$ independently represent, on each occasion when mentioned above, H, a heterocycloalkyl group optionally substituted by one or more $C_{1-4}$ alkyl groups (such as a 4-methylpiperazinyl, group) or $C_{1-6}$ alkyl (such as cyclopentyl, cyclopropyl or, preferably, methyl, ethyl, ethylene, n-propyl, isopropyl, n-butyl, isobutyl, t-butyl or cyclobutylmethyl), which latter group is optionally substituted by one or more substituents selected from halo (e.g. fluoro) groups (so forming, for example, a fluoromethyl, difluoromethyl or trifluoromethyl group), —OR$^{17}$, —N($R^{18}$)$R^{19}$, —C(O)OR$^{17}$ and —C(O)N($R^{18}$)$R^{19}$;

wherein $R^{17}$, $R^{18}$ and $R^{19}$ independently represent, on each occasion when mentioned above, H, $C_{1-6}$ alkyl (such as methyl, ethyl, n-propyl, isopropyl, n-butyl, isobutyl, t-butyl), which alkyl groups are optionally substituted by one or more halo (especially fluoro) groups; or $R^{18}$ and $R^{19}$ are linked to form a 4- to 8-membered ring optionally containing a further 1 to 2 heteroatoms (e.g. a pyrrolidinyl or a piperazinyl group), which ring is optionally substituted by a $C_{1-3}$ alkyl group (such as methyl).

Preferred values of $R^6$ include $C_{1-4}$ alkyl and, particularly, H.

Preferred values of X include H, Cl and Br.

More preferred compounds include those in which:

$R^1$ represents an aryl group such as a phenyl or naphthyl (e.g. 2-naphthyl) group or a heteroaryl group such as a quinolinyl or, preferably, a pyridyl group, both of which are optionally substituted by one or two A groups;

$R^2$ represents $G^1$ or, more preferably, hydrogen;

$R^3$ and $R^4$ independently represent $G^1$ or, more preferably, hydrogen, an aryl group such as a phenyl group or a heteroaryl group such as a pyrimidinyl or, preferably, a pyridyl group, which latter two groups are optionally substituted by one or two A groups;

at least one of $R^3$ and $R^4$ represents optionally substituted aryl or heteroaryl, and up to one other represents $G^1$ or, more preferably, hydrogen;

when $R^3$ or $R^4$ represents an aryl or heteroaryl group, then the other substituents on the essential benzene ring in the compound of formula I (i.e. $R^2$, $R^5$ and $R^3$ or $R^4$ (as appropriate)) independently represent H or $G^1$ (e.g. halo (such as chloro), cyano, methyl, methoxy, trifluoromethyl or trifluoromethoxy);

A represents $G^1$;

$G^1$ represents cyano, halo (e.g. bromo, fluoro or, more particularly, chloro) or, more preferably, —$NO_2$ or -$A^1$-$R^7$;

$A^1$ represents —$C(O)A^2$- or, more preferably, a single bond, —$S(O)_2A^3$-, —$N(R^8)A^4$- or —$OA^5$-;

$A^2$ represents —$N(R^8)$—;

$A^3$ represents a single bond;

$A^4$ represents a single bond or —$C(O)$—;

$A^5$ represents a single bond;

$R^7$ represents hydrogen, optionally branched, optionally unsaturated and/or optionally cyclic $C_{1-6}$ alkyl, or a heterocycloalkyl group (such as a nitrogen-containing heterocycloalkyl group optionally containing one or two double bonds, so forming for example a piperidinyl, pyrrolidinyl, morpholinyl group or, more preferably a piperazinyl group), which latter two groups are optionally substituted by one or more substituents selected from $G^3$;

$R^8$ represents hydrogen or $C_{1-6}$ alkyl, which latter group is optionally substituted by one or more substituents selected from $G^3$;

$G^3$ represents halo (especially fluoro) or -$A^1$-$R^{11}$;

$A^{11}$ represents a single bond, —$C(O)A^{12}$, —$N(R^{12})$— or —O—;

$A^{12}$ represents —O— or —$N(R^{12})$—;

$R^{11}$ represents hydrogen or $C_{1-3}$ alkyl (such as methyl or ethyl); or $R^{11}$ and $R^{12}$ are linked to form a 5- to 6-membered ring optionally containing one further heteroatom (further to the nitrogen atom to which $R^{11}$ and $R^{12}$ are attached), for example a nitrogen heteroatom, and which ring is optionally substituted by a $C_{1-3}$ alkyl (e.g. methyl) group.

Especially preferred compounds of the invention are wherein:

$R^6$ represents H;

$R^1$ represents a phenyl group, optionally substituted, for example by halo (e.g. chloro), -$A^1$-$R^7$ or —$NO_2$ (e.g. optionally substituted, for example in the 4-position, by a -$A^1$-$R^7$ or a —$NO_2$ group and optionally further substituted, for example in the 3-position, by a —$NO_2$ group). In such instances, $A^1$ may represent —$OA^5$-, a single bond or a —$S(O)_2A^3$- group. When $A^1$ represents —$OA^5$-, $A^5$ is preferably a single bond and $R^7$ is preferably $C_{1-6}$ alkyl, such as cyclopropyl, cyclopentyl or, more particularly, methyl, ethyl, isopropyl, isobutyl, t-butyl or cyclobutylmethyl, optionally substituted by one or more $G^3$ groups. In such instances $G^3$ may represent halo (especially fluoro) or -$A^{11}$-$R^{11}$, wherein $A^{11}$ preferably represents —$C(O)A^{12}$, —$OA^{15}$- or —$N(R^{12})A^{14}$-, in which $A^{14}$ and $A^{15}$ are preferably single bonds and $A^{12}$ is preferably —O— or —$N(R^{12})$—. In the instance when $A^{11}$ represents —$OR^{11}$—, $R^{11}$ is preferably H, when $A^{11}$ represents —$N(R^{12})R^{11}$, $R^{11}$ and $R^{12}$ are preferably linked to form a 5-membered ring, such as a pyrrolidine ring, when $A^{11}$ represents —$C(O)OR^{11}$, $R^{11}$ is preferably H and when $A^{11}$ represents —$C(O)N(R^{12})R^{11}$, then $R^{11}$ and $R^{12}$ are preferably linked to form a 6-membered ring, optionally containing a further nitrogen heteroatom, such as a piperazine ring, which ring is optionally substituted by a $C_{1-2}$ alkyl, such as a methyl, group. When $A^1$ represents a single bond, $R^7$ may represent a $C_{1-6}$ (e.g. $C_{1-3}$) alkyl group, such as a cyclohexyl or, more particularly, a methyl or ethylene group, both of which are optionally substituted by one or more $G^3$ group. In such instances, $G^3$ may represent halo (especially fluoro), or a -$A^{11}$-$R^{11}$ group, wherein $A^{11}$ is preferably a —$C(O)A^{12}$- group, in which $A^{12}$ preferably represents —O— and $R^{11}$ is preferably H. When $A^1$ represents —$S(O)_2A^3$-, $A^3$ is preferably a single bond and $R^7$ may represent a $C_{1-3}$ alkyl group, such as ethyl or, preferably, methyl, or $R^7$ may also represent a heterocycloalkyl group, such as a piperazine group, optionally substituted by $G^3$, wherein $G^3$ is preferably -$A^{11}$-$R^{11}$, $A^{11}$ is preferably a single bond and $R^7$ may represent a $C_{1-2}$ alkyl group, such as a methyl group. Thus $R^1$ may represent a 4-cyclopropoxyphenyl, 4-cyclopentoxyphenyl, 4-cyclopentoxy-3-nitrophenyl, 4-isopropoxy-3-nitrophenyl, 4-chlorophenyl, 3,5-dichlorophenyl, 4-cyclo-hexylphenyl or, more particularly, 4-isopropoxyphenyl, 4-ethoxyphenyl, 4-isobutoxyphenyl, 4-cyclobutylmethoxyphenyl, 4-methoxy-phenyl, 4-(2-methyl-1-(pyrrolidin-1-yl)propan-2-yloxy)phenyl, 4-(1-hydroxy-2-methyl-propan-2-yloxy)phenyl, 4-trifluoromethoxyphenyl, 4-methylsulfonylphenyl, 4-methyl-3-nitrophenyl, 4-trifluoromethylphenyl, 4-(2-carboxypropan-2-yloxy)phenyl, 4-(2-carboxyvinyl)phenyl, 4-nitro-phenyl, 4-(2-methyl-1-(4-methylpiperazin-1-yl)propan-2-yloxy) phenyl, 4-(4-methylpiperazin-1-ylsulfonyl)phenyl or a phenyl group;

$R^1$ may also be a 2-naphthyl group, optionally substituted, for example in the 6-position by a single -$A^1$-$R^7$ group. In such instances, $A^1$ may represent —$OA^5$-, in which $A^5$ is a single bond and $R^7$ represents $C_{1-3}$ alkyl, such as an optionally branched propyl group, so forming, for example a 6-isopropoxynaphthalen-2-yl or 2-naphthyl group;

$R^1$ may also be a quinolinyl (e.g. 3-quinolinyl) group;

$R^1$ may alternatively represent a 2- or 3-pyridyl group, substituted at the theta or, preferably, para-position relative to the point of attachment of the $R^1$ group to the indole ring with a single substituent selected from -$A^1$-$R^7$. In such instances, $A^1$ may represent —$N(R^8)A^4$- or, more particularly, —$OA^5$— or a single bond. When $A^1$ represents —$OA^5$-, $A^5$ is preferably a single bond and $R^7$ may represent $C_{1-5}$ (e.g. $C_{1-3}$) alkyl, such as cyclopentyl or, more particularly, ethyl or isopropyl. When $A^1$ represents a single bond, $R^7$ may represent $C_{1-3}$ alkyl, such as ethyl or, preferably, methyl, which group is optionally substituted by G³, in which G³ is halo (e.g. fluoro) or, particularly, —OR¹¹ and R¹¹ may represent $C_{1-3}$ alkyl, such as ethyl. When A¹ represents —N(R⁸)A⁴-, A⁴ is preferably a single bond, R⁸ is preferably hydrogen and R⁷ may represent $C_{1-6}$ alkyl, such as cyclic $C_{3-5}$ alkyl (e.g. cyclopentyl). Thus R¹ may also represent a 6-cyclopentoxypyrid-3-yl, 5-cyclopentylaminopyrid-2-yl, 5-trifluoromethylpyrid-2-yl or, more particularly, a 5-ethoxymethylpyrid-2-yl or 6-isopropoxypyrid-3-yl group; when R² represents G¹, G¹ represents halo (e.g. chloro), cyano, methyl, trifluoromethyl or, more preferably, —NO₂ or -A¹-R⁷, in which A¹ is —N(R⁸)A⁴-. In such instances, A⁴ may represent a single bond or a —C(O)— group, R⁸ represents H and R⁷ represents H or $C_{1-3}$ alkyl, such as methyl. In this respect, R² may represent H, —N(H)C(O)Me or —NH₂;

R³ represents H or a phenyl group optionally substituted by one or more (e.g. two) groups selected from halo (e.g. chloro) and -A¹-R⁷ (e.g. substituted at the 3- or, more particularly, 4-position by a single -A¹-R⁷ group). In such instances, A¹ may represent —C(O)A²-, in which case A² represents —N(R⁸)— and R⁷ and R⁸ independently represent hydrogen, or A¹ may, more preferably, represent a single bond or —OA⁵-, in which A⁵ is a single bond, and R⁷ represents $C_{1-6}$ alkyl, such as methyl, isopropyl, t-butyl or hexyl (especially cyclohexyl) optionally substituted by one or more G³ groups in which G³ is halo, such as fluoro, to form, for example, a 4-chlorophenyl, 3,5-dichlorophenyl, 2,4-dichlorophenyl, 4-carbamoylphenyl group or, more particularly, a 4-tert-butylphenyl, 4-isopropoxyphenyl, 4-trifluoromethylphenyl, 4-trifluoromethoxyphenyl or 4-cyclohexylphenyl group;

R³ may alternatively represent a 2- or 3-pyridyl group, substituted at the meta or, preferably, para-position relative to the point of attachment of the R³ group to the indole ring with a single substituent selected from halo (e.g. chloro) or, more preferably, -A¹-R⁷. In such instances, A¹ may represent —N(R⁸)A⁴-, in which A⁴ represents a single bond, R⁸ represents hydrogen and R⁷ represents $C_{1-6}$ alkyl, such as cyclic $C_{3-5}$ alkyl (e.g. cyclopentyl) or, A¹ may, more particularly represent a single bond or —OA⁵-, in which A⁵ is a single bond and R⁷ represents a heterocycloalkyl (such as a 5-membered nitrogen containing heterocycloalkyl ring optionally containing a double bond (e.g. 3,4,5,6-tetrahydro-2H-pyridyl)) or, more particularly a $C_{1-5}$ (e.g. $C_{1-3}$) alkyl, such as cyclopentyl or, more particularly, methyl or isopropyl optionally substituted by one or more G³ groups in which G³ is halo such as fluoro, to form for example a 5-chloropyrid-2-yl, 5-cyclopentylaminopyrid-2-yl, 6-cyclopentoxypyrid-3-yl, 6-(piperidin-1-yl)pyridin-3-yl or, more particularly, a 5-trifluoromethylpyrid-2-yl or 6-isopropoxypyrid-3-yl group; R³ may alternatively represent pyrimidinyl group (e.g. 2-pyrimidinyl), optionally substituted, for example at the meta or, more particularly, para position relative to the point of attachment of the R³ group to the indole ring, with a single substituent selected from halo (e.g. bromo) and -A¹-R⁷, in which A¹ preferably represents a single bond and R⁷ represents $C_{1-3}$ alkyl (e.g. propyl) or a heteroaryl group, for example a nitrogen-containing heteroaryl group such as pyridyl (e.g. 2-pyridyl). Thus R³ may also represent 5-bromopyrimidin-2-yl, 5-propylpyrimidin-2-yl or 5-(pyridin-2-yl)pyrimidin-2-yl;

R⁴ represents H, a pyridyl group or a phenyl group, which latter group may be substituted at the 3- or, more particularly, 4-position with a single -A¹-R⁷ group. In such instances, A¹ may represent —OA⁵-, in which A⁵ is a single bond and R⁷ represents $C_{1-4}$ alkyl, such as isopropyl, optionally substituted by one or more G³ groups in which G³ is halo, such as fluoro, so forming, for example, a 4-isopropoxyphenyl group;

R⁵ represents H.

Particularly preferred compounds of the invention include those of the examples described hereinafter.

Compounds of the invention may be made in accordance with techniques that are well known to those skilled in the art, for example as described hereinafter.

According to a further aspect of the invention there is provided a process for the preparation of a compound of formula I, which process comprises:

(i) for compounds of formula I wherein X represents halo, reaction of a compound of formula I wherein X represents H, with a reagent or mixture of reagents known to be a source of halide ions. For example, for bromide ions, N-bromosuccinimide may be employed, for iodide ions, iodine or a mixture of NaI and N-chlorosuccinimide may be employed, for chloride ions, N-chlorosuccinimide may be employed and for fluoride ions, 1-(chloromethyl)-4-fluoro-1,4-diazoniabicyclo[2.2.2]octane bis(tetrafluoroborate) may be employed. This reaction may be carried out in a suitable solvent (e.g. acetone, benzene or dioxane) under conditions known to the skilled person;

(ii) for compounds of formula I wherein X represents H, reaction of a compound of formula II,

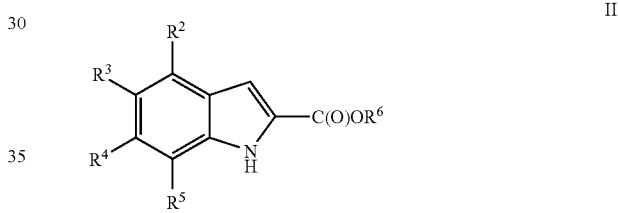

wherein R², R³, R⁴, R⁵ and R⁶ are as hereinbefore defined, with a compound of formula III,

R¹L¹    III wherein L¹ represents a suitable leaving group such as chloro, bromo, iodo, a sulfonate group (e.g. —OS(O)₂CF₃, —OS(O)₂CH₃, —OS(O)₂PhMe or a nonaflate) or —B(OH)₂ and R¹ is as hereinbefore defined, for example optionally in the presence of an appropriate metal catalyst (or a salt or complex thereof) such as Cu, Cu(OAc)₂, CuI (or CuI/diamine complex), Pd(OAc)₂, Pd₂(dba)₃ or NiCl₂, and an optional additive such as Et₃N, pyridine, N,N'-dimethylethylenediamine, Ph₃P, 2,2'-bis(diphenylphosphino)-1,1'-binaphthyl, xantphos, NaI or an appropriate crown ether such as 18-crown-6-benzene, in the presence of an appropriate base such as NaH, Et₃N, pyridine, N,N'-dimethylethylenediamine, Na₂CO₃, K₂CO₃, K₃PO₄, Cs₂CO₃, t-BuONa or t-BuOK (or a mixture thereof), in a suitable solvent (e.g. dichloromethane, dioxane, toluene, ethanol, isopropanol, dimethylformamide, ethylene glycol, ethylene glycol dimethyl ether, water, dimethylsulfoxide, acetonitrile, dimethylacetamide, N-methylpyrrolidinone, tetrahydrofuran or a mixture thereof) or in the absence of an additional solvent when the reagent may itself act as a solvent (e.g. when R¹ represents phenyl and L¹ represents bromo, i.e. bromobenzene). This reaction may be carried out at room temperature or above (e.g. at a high temperature, such as the reflux temperature of the solvent system that is employed) or using microwave irradiation;

(iii) for compounds of formula I wherein X represents H, reaction of a compound of formula IV,

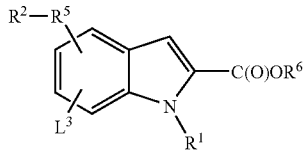

wherein $L^3$ represents $L^1$ or $L^2$, in which L represents a suitable leaving group such as chloro, bromo, iodo, —B(OH)$_2$ or a protected derivative thereof, for example a 4,4,5,5-tetramethyl-1,3,2-dioxaborolan-2-yl group, 9-borabicyclo[3.3.1]nonane (9-BBN), —Sn(alkyl)$_3$ (e.g. —SnMe$_3$ or —SnBu$_3$), or a similar group known to the skilled person, and $L^3$ is attached to one or more of the carbon atoms of the benzenoid ring of the indole, and the remaining positions of the benzenoid ring are substituted with 1 to 3 (depending on the number of $L^3$ substituents) $R^2$-$R^5$ substituents, $R^2$-$R^5$ represents any one of the substituents, i.e. $R^2$, $R^3$, $R^4$ and $R^5$, that are already present in that ring (as appropriate), and $L^1$, $R^1$, $R^2$, $R^3$, $R^4$, $R^5$ and $R^6$ are as hereinbefore defined, with a compound of formula V, $$R^{20}L^4 \qquad V$$

wherein $R^{20}$ represents $R^2$, $R^3$, $R^4$ or $R^5$ (as appropriate), and $L^4$ represents $L^1$ (when $L^3$ represents $L^2$) or $L^2$ (when $L^3$ represents $L^1$), as hereinbefore defined. The skilled person will appreciate that $L^1$ and $L^2$ will be mutually compatible. This reaction may be performed, for example in the presence of a suitable catalyst system, e.g. a metal (or a salt or complex thereof such as CuI, PdCl$_2$, Pd/C, Pd(OAc)$_2$, Pd(Ph$_3$P)$_2$Cl$_2$, Pd(Ph$_3$P)$_4$, Pd$_2$(dba)$_3$ or NiCl$_2$ and an additive such as t-Bu$_3$P, (C$_6$H$_{11}$)$_3$P, Ph$_3$P, AsPh$_3$, P(o-Tol)$_3$, 1,2-bis(diphenylphosphino)ethane, 2,2'-bis(di-tert-butylphosphino)-1,1'-biphenyl, 2,2'-bis(diphenylphosphino)-1,1'-binaphthyl, 1,1'-bis(diphenyl-phosphinoferroceine), 1,3-bis(diphenylphosphino)propane or xantphos, together with a suitable base such as, Na$_2$CO$_3$, K$_3$PO$_4$, Cs$_2$CO$_3$, KOH, NaOH, K$_2$CO$_3$, CsF, Et$_3$N, (i-Pr)$_2$NEt, t-BuONa or t-BuOK (or mixtures thereof) in a suitable solvent such as dioxane, toluene, ethanol, dimethylformamide, ethylene glycol dimethyl ether, water, dimethylsulfoxide, acetonitrile, dimethylacetamide, N-methylpyrrolidinone, tetrahydrofuran or mixtures thereof. The reaction may be carried out for example at room temperature or above (e.g. at a high temperature such as the reflux temperature of the solvent system) or using microwave irradiation. The skilled person will appreciate that when $L^3$ or $L^4$ (of the compounds of formulae IV and V, respectively, represent halo, such compounds may first be activated by:

(I) forming the corresponding Grignard reagent under standard conditions known to those skilled in the art (e.g. employing magnesium or a suitable reagent such as a mixture of C$_{1-6}$ alkyl-Mg-halide and ZnCl$_2$ or LiCl), followed by reaction with a compound of formula IV or V (as appropriate), optionally in the presence of a catalyst (e.g. FeCl$_3$) under conditions known to those skilled in the art; or (II) forming the corresponding lithiated compound under halogen-lithium exchange reaction conditions known to those skilled in the art (e.g. employing n-BuLi or t-BuLi in the presence of a suitable solvent (e.g. a polar aprotic solvent, such as THF)), followed by reaction with a compound of formula IV or V (as appropriate).

The skilled person will also appreciate that the magnesium of the Grignard reagent or the lithium of the lithiated species may be exchanged for a different metal (i.e. a transmetallation reaction may be performed), for example to zinc (e.g. using ZnCl$_2$) and the intermediate so formed may then be subjected to reaction with a compound of formula IV or V (as appropriate) under conditions known to those skilled in the art, for example such as those described above;

Compounds of formula II, may be prepared by reaction of a compound of formula VI,

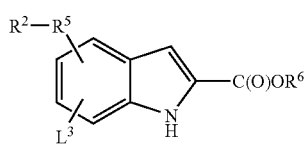

wherein $L^3$, $R^2$-$R^5$ and $R^6$ are as hereinbefore defined with a compound of formula V as hereinbefore defined, for example under conditions such as those described hereinbefore in respect of preparation of compounds of formula I (process step (iii)) above.

Compounds of formula IV, may be prepared by reaction of a compound of formula VI with a compound of formula III as hereinbefore defined, for example under reaction conditions such as those described hereinbefore in respect of preparation of compounds of formula I (process step (ii)) above.

Compounds of formula IV in which $L^3$ represents $L^2$ may be prepared by reaction of a compound of formula IV in which $L^3$ represents $L^1$, with an appropriate reagent for the introduction of the $L^2$ group. This conversion may be performed by methods known to those skilled in the art, for example:

i) compounds of formula IV, in which $L^3$ is 4,4,5,5-tetramethyl-1,3,2-dioxaborolan-2-yl may be prepared by reaction of the reagent bis(pinacolato)diboron with a compound of formula IV in which $L^3$ represents $L^1$, for example under reaction conditions such as those described hereinbefore in respect of preparation of compounds of formula I (process step (ii)) above;

ii) compounds of formula IV, in which $L^3$ represents —B(OH)$_2$ may be prepared by reaction of a corresponding compound of formula IV in which $L^3$ represents halo by reaction with, for example, boronic acid or a protected derivative thereof (e.g. bis(pinacolato)diboron or triethyl borate) followed by (if necessary) deprotection under standard conditions. The skilled person will appreciate that the compound of formula IV in which $L^3$ represents halo may first need to be converted to the corresponding Grignard reagent, or another metal (e.g. via a transmetallation reaction), for example under conditions such as those described in respect of preparation of compounds of formula I (process step (iii)) above; or (iii) compounds of formula IV in which $L^3$ represents a halo group may be prepared by reaction of a corresponding compound of formula IV in which $L^3$ represents a different halo group, for example employing a suitable source of halide ions such as those described hereinbefore in respect of preparation of compounds of formula I (process step (i)) above, under conditions known to those skilled in the art. For example, conversion of a bromo group to an iodo group may be performed in the presence of NaI, optionally in the presence of a suitable catalyst (e.g. CuI) and/or a catalytic amount of base (e.g. N'N,-dimethyl-1,2-diaminoethane) in the presence of a suitable solvent such as one described hereinbefore in respect of preparation of compounds of formula I (process step (i)) above.

Conversions of the $L^4$ group and the $L^3$ group in the compounds of formulae V and VI, respectively, may be performed in a similar manner to that described above in respect of converting the $L^3$ group in compounds of formula IV.

Compounds equivalent to compounds of formula II, IV and VI, but which are substituted in the 3-position with a halo group may be prepared by reaction of a corresponding compound of formula II, IV and VI, respectively, with a reagent known to be a source of halide ions, for example under conditions such as those hereinbefore described in respect of preparation of compounds of formula I (process step (i)) above.

Compounds of formulae III, V, and VI are either commercially available, are known in the literature, or may be obtained either by analogy with the processes described herein, or by conventional synthetic procedures, in accordance with standard techniques, from available starting materials using appropriate reagents and reaction conditions. In this respect, the skilled person may refer to inter alia "*Comprehensive Organic Synthesis*" by B. M. Trost and I. Fleming, Pergamon Press, 1991.

Indoles of formulae II, IV and VI, may also be prepared with reference to a standard heterocyclic chemistry textbook (e.g. "*Heterocyclic Chemistry*" by J. A. Joule. K. Mills and G. F. Smith, $3^{rd}$ edition, published by Chapman & Hall or "*Comprehensive Heterocyclic Chemistry II*" by A. R. Katritzhy, C. W. Rees and E. F. V. Scriven, Pergamon Press, 1996) and/or made according to the following general procedures.

For example compounds of formulae II and VI, may be prepared by reaction of a compound of formula VII,

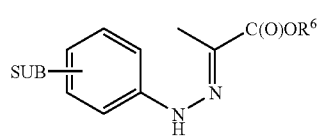

VII wherein SUB represents the substitution pattern that is present in the compound of formula II or VI to be formed and $R^6$ is as hereinbefore defined, under standard Fischer indole synthesis conditions known to the person skilled in the art.

Compounds of formulae II and VI, may alternatively be prepared by reaction of a compound of formula VIII,

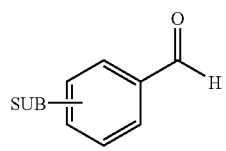

VIII wherein SUB is as hereinbefore defined with a compound of formula IX,

   IX wherein $R^6$ is as hereinbefore defined and preferably does not represent hydrogen, under conditions, known to the person skilled in the art (i.e. to induce a condensation reaction, followed by a thermally induced cyclisation).

Compounds of formula VII, may be prepared by:
(a) reaction of a compound of formula X,

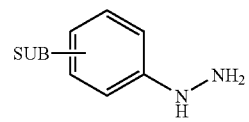

X wherein SUB is as hereinbefore defined with a compound of formula XI, $H_3CC(O)C(O)OR^6$   XI wherein $R^6$ is as hereinbefore defined under conditions known to the skilled person; or
(b) reaction of a compound of formula XII,

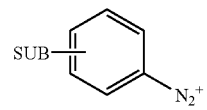

XII wherein SUB is as hereinbefore defined with a compound of formula XIII,

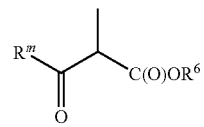

XIII wherein $R^m$ represents OH, O—$C_{1-6}$ alkyl or $C_{1-6}$ alkyl and $R^6$ is as hereinbefore defined, for example under Japp-Klingemann conditions known to the skilled person.

Compounds of formulae VIII, IX, X, XI, XII, XIII are either commercially available, are known in the literature, or may be obtained either by analogy with the processes described herein, or by conventional synthetic procedures, in accordance with standard techniques, from available starting materials using appropriate reagents and reaction conditions. In this respect, the skilled person may refer to inter alia "*Comprehensive Organic Synthesis*" by B. M. Trost and I. Fleming, Pergamon Press, 1991.

The substituents $R^1$, $R^2$, $R^3$, $R^4$, $R^5$, $R^6$ and X in final compounds of the invention or relevant intermediates may be modified one or more times, after or during the processes described above by way of methods that are well known to those skilled in the art. Examples of such methods include substitutions, reductions, oxidations, alkylations, hydrolyses, esterifications, and etherifications. The precursor groups can be changed to a different such group, or to the groups defined in formula I, at any time during the reaction sequence. For example, in cases where $R^6$ does not initially represent hydrogen (so providing an ester functional group), the skilled person will appreciate that at any stage during the synthesis (e.g. the finial step), the relevant substituent may be hydrolysed to form a carboxylic acid functional group (in which case $R^6$ will be hydrogen). Further, halo groups (e.g. of a compound of formula I when X represents halo) may be converted to other halo groups, for example as described hereinbefore. In this respect, the skilled person may also refer to "*Comprehensive Organic Functional Group Transformations*" by A. R. Katritzky, O. Meth-Cohn and C. W. Rees, Pergamon Press, 1995.

Compounds of the invention may be isolated from their reaction mixtures using conventional techniques.

It will be appreciated by those skilled in the art that, in the processes described above and hereinafter, the functional groups of intermediate compounds may need to be protected by protecting groups.

The protection and deprotection of functional groups may take place before or after a reaction in the above-mentioned schemes.

Protecting groups may be removed in accordance with techniques that are well known to those skilled in the art and as described hereinafter. For example, protected compounds/intermediates described herein may be converted chemically to unprotected compounds using standard deprotection techniques.

The type of chemistry involved will dictate the need, and type, of protecting groups as well as the sequence for accomplishing the synthesis.

The use of protecting groups is fully described in "*Protective Groups in Organic Chemistry*", edited by J W F McOmie, Plenum Press (1973), and "*Protective Groups in Organic Synthesis*", $3^{rd}$ edition, T. W. Greene & P. G. M. Wutz, Wiley-Interscience (1999).

Medical and Pharmaceutical Uses

Compounds of the invention are indicated as pharmaceuticals. According to a further aspect of the invention there is provided a compound of the invention, as hereinbefore defined but without the proviso, for use as a pharmaceutical.

Although compounds of the invention may possess pharmacological activity as such, certain pharmaceutically-acceptable (e.g. "protected") derivatives of compounds of the invention may exist or be prepared which may not possess such activity, but may be administered parenterally or orally and thereafter be metabolised in the body to form compounds of the invention. Such compounds (which may possess some pharmacological activity, provided that such activity is appreciably lower than that of the "active" compounds to which they are metabolised) may therefore be described as "prodrugs" of compounds of the invention.

By "prodrug of a compound of the invention", we include compounds that form a compound of the invention, in an experimentally-detectable amount, within a predetermined time (e.g. about 1 hour), following oral or parenteral administration. All prodrugs of the compounds of the invention are included within the scope of the invention.

Furthermore, certain compounds of the invention (including, but not limited to, compounds of formula I in which $R^6$ is other than hydrogen) may possess no or minimal pharmacological activity as such, but may be administered parenterally or orally, and thereafter be metabolised in the body to form compounds of the invention that possess pharmacological activity as such (including, but not limited to, corresponding compounds of formula I, in which $R^6$ represents hydrogen). Such compounds (which also includes compounds that may possess some pharmacological activity, but that activity is appreciably lower than that of the "active" compounds of the invention to which they are metabolised), may also be described as "prodrugs".

Thus, the compounds of the invention are useful because they possess pharmacological activity, and/or are metabolised in the body following oral or parenteral administration to form compounds which possess pharmacological activity.

Compounds of the invention are particularly useful because they may inhibit (for example selectively) the activity of prostaglandin E synthases (and particularly microsomal prostaglandin E synthase-1 (mPGES-1)), i.e. they prevent the action of mPGES-1 or a complex of which the mPGES-1 enzyme forms a part, and/or may elicit a mPGES-1 modulating effect, for example as may be demonstrated in the test described below. Compounds of the invention may thus be useful in the treatment of those conditions in which inhibition of a PGES, and particularly mPGES-1, is required.

Compounds of the invention may inhibit the activity of leukotriene $C_4$ ($LTC_4$), for example as may be shown in a test such as that described in *Eur. J. Biochem.*, 208, 725-734 (1992), and may thus be useful in the treatment of those conditions in which inhibition of $LTC_4$ is required. Compounds of the invention may also inhibit the activity of 5-lipoxygenase-activating protein (FLAP), for example as may be shown in a test such as that described in *Mol. Pharmacol.*, 41, 873-879 (1992).

Compounds of the invention are thus expected to be useful in the treatment of inflammation.

The term "inflammation" will be understood by those skilled in the art to include any condition characterised by a localised or a systemic protective response, which may be elicited by physical trauma, infection, chronic diseases, such as those mentioned hereinbefore, and/or chemical and/or physiological reactions to external stimuli (e.g. as part of an allergic response). Any such response, which may serve to destroy, dilute or sequester both the injurious agent and the injured tissue, may be manifest by, for example, heat, swelling, pain, redness, dilation of blood vessels and/or increased blood flow, invasion of the affected area by white blood cells, loss of function and/or any other symptoms known to be associated with inflammatory conditions.

The term "inflammation" will thus also be understood to include any inflammatory disease, disorder or condition per se, any condition that has an inflammatory component associated with it, and/or any condition characterised by inflammation as a symptom, including inter alia acute, chronic, ulcerative, specific, allergic and necrotic inflammation, and other forms of inflammation known to those skilled in the art. The term thus also includes, for the purposes of this invention, inflammatory pain, pain generally and/or fever.

Accordingly, compounds of the invention may be useful in the treatment of inflammatory bowel disease, irritable bowel syndrome, migraine, headache, low back pain, fibromyalgia, myofascial disorders, viral infections (e.g. hepatitis C and, particularly, influenza, common cold, herpes zoster, and AIDS), bacterial infections, fungal infections, dysmenorrhea, burns, surgical or dental procedures, malignancies (e.g. breast cancer, colon cancer, and prostate cancer), atherosclerosis, gout, arthritis, osteoarthritis, juvenile arthritis, rheumatoid arthritis, fever (e.g. rheumatic fever), ankylosing sodalities, systemic lupus erythematosus, vasculitis, pancreatitis, nephritis, bursitis, conjunctivitis, iritis, scleritis, uveitis, a wound healing, dermatitis, eczema, psoriasis, stroke, diabetes mellitus, neurodegenerative disorders such as Alzheimer's disease and multiple sclerosis, autoimmune diseases, osteoporosis, asthma, chronic obstructive pulmonary disease, pulmonary fibrosis, allergic disorders, rhinitis, ulcers, coronary heart disease, sarcoidosis and any other disease with an inflammatory component. Other diseases that may be mentioned include inflammatory pain, hyperprostaglandin E syndrome, classic Bartter syndrome, Hodgkin's disease and persistent ductus (PDA).

Compounds of the invention may also have effects that are not linked to inflammatory mechanisms, such as in the reduction of bone loss in a subject. Conditions that may be mentioned in this regard include osteoporosis, osteoarthritis, Paget's disease and/or periodontal diseases. Compounds the invention may thus also be useful in increasing bone mineral density, as well as the reduction in incidence and/or healing of fractures, in subjects.

Compounds of the invention are indicated both in the therapeutic and/or prophylactic treatment of the above-mentioned conditions.

According to a further aspect of the present invention, there is provided a method of treatment of a disease which is associated with, and/or which can be modulated by inhibition of $LTC_4$, FLAP and/or, preferably, a PGES (such as mPGES-1), and/or a method of treatment of a disease in which inhibition of the activity of $LTC_4$, FLAP and/or, preferably, a PGES (and particularly mPGES-1) is desired and/or required (e.g. inflammation), which method comprises administration of a therapeutically effective amount of a compound of the invention, as hereinbefore defined but without the proviso, to a patient suffering from, or susceptible to, such a condition.

"Patients" include mammalian (including human) patients.

The term "effective amount" refers to an amount of a compound, which confers a therapeutic effect on the treated patient. The effect may be objective (i.e. measurable by some test or marker) or subjective (i.e. the subject gives an indication of or feels an effect).

Compounds of the invention will normally be administered orally, intravenously, subcutaneously, buccally, rectally, dermally, nasally, tracheally, bronchially, sublingually, by any other parenteral route or via inhalation, in a pharmaceutically acceptable dosage form.

Compounds of the invention may be administered alone, but are preferably administered by way of known pharmaceutical formulations, including tablets, capsules or elixirs for oral administration, suppositories for rectal administration, sterile solutions or suspensions for parenteral or intramuscular administration, and the like.

Such formulations may be prepared in accordance with standard and/or accepted pharmaceutical practice.

According to a further aspect of the invention there is thus provided a pharmaceutical formulation including a compound of the invention, as hereinbefore defined but without the proviso, in admixture with a pharmaceutically acceptable adjuvant, diluent or carrier.

Compounds of the invention may also be combined with other therapeutic agents that are useful in the treatment of inflammation (e.g. NSAIDs and coxibs).

According to a further aspect of the invention, there is provided a combination product comprising:

(A) a compound of the invention, as hereinbefore defined but without the proviso; and
(B) another therapeutic agent that is useful in the treatment of inflammation, wherein each of components (A) and (B) is formulated in admixture with a pharmaceutically-acceptable adjuvant, diluent or carrier.

Such combination products provide for the administration of a compound of the invention in conjunction with the other therapeutic agent, and may thus be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the other therapeutic agent).

Thus, there is further provided:

(1) a pharmaceutical formulation including a compound of the invention, as hereinbefore defined but without the proviso, another therapeutic agent that is useful in the treatment of inflammation, and a pharmaceutically-acceptable adjuvant, diluent or carrier; and (2) a kit of parts comprising components:
(a) a pharmaceutical formulation including a compound of the invention, as hereinbefore defined but without the proviso, in admixture with a pharmaceutically-acceptable adjuvant, diluent or carrier; and
(b) a pharmaceutical formulation including another therapeutic agent that is useful in the treatment of inflammation in admixture with a pharmaceutically-acceptable adjuvant, diluent or carrier, which components (a) and (b) are each provided in a form that is suitable for administration in conjunction with the other.

Compounds of the invention may be administered at varying doses. Oral, pulmonary and topical dosages may range from between about 0.01 mg/kg of body weight per day (mg/kg/day) to about 100 mg/kg/day, preferably about 0.01 to about 10 mg/k-g/day, and more preferably about 0.1 to about 5.0 mg/k-g/day. For e.g. oral administration, the compositions typically contain between about 0.01 mg to about 500 mg, and preferably between about 1 mg to about 100 mg, of the active ingredient. Intravenously, the most preferred doses will range from about 0.001 to about 10 mg/kg/hour during constant rate infusion. Advantageously, compounds may be administered in a single daily dose, or the total daily dosage may be administered in divided doses of two, three or four times daily.

In any event, the physician, or the skilled person, will be able to determine the actual dosage which will be most suitable for an individual patient, which is likely to vary with the route of administration, the type and severity of the condition that is to be treated, as well as the species, age, weight, sex, renal function, hepatic function and response of the particular patient to be treated. The above-mentioned dosages are exemplary of the average case; there can, of course, be individual instances where higher or lower dosage ranges are merited, and such are within the scope of this invention.

Compounds of the invention may have the advantage that they are effective, and preferably selective, inhibitors of prostaglandin E synthases (PGES) and particularly microsomal prostaglandin E synthase-1 (mPGES-1). The compounds of the invention may reduce the formation of the specific arachidonic acid metabolite $PGE_2$ without reducing the formation of other COX generated arachidonic acid metabolites, and thus may not give rise to the associated side-effects mentioned hereinbefore.

Compounds of the invention may also have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art, whether for use in the above-stated indications or otherwise.

Biological Test

In the assay human mPGES-1 catalyses the reaction where the substrate $PGH_2$ is converted to $PGE_2$. mPGES-1 is expressed in E. coli and the membrane fraction is dissolved in 20 mM NaPi-buffer pH 8.0 and stored at −80° C. In the assay human mPGES-1 is dissolved in 0.1 M KPi-buffer pH 7.35 with 2.5 mM glutathione. The stop solution consists of $H_2O$/MeCN (7/3), containing $FeCl_2$ (25 mM) and HCl (0.15 M). The assay is performed at room temperature in 96-well plates. Analysis of the amount of $PGE_2$ is performed with reversed phase HPLC (Waters 2795 equipped with a 3.9×150 mm C18 column). The mobile phase consists of $H_2O$/MeCN (7/3), containing TFA (0.056%), and absorbance is measured at 195-nm with a Waters 2487 UV-detector.

The following is added chronologically to each well:
1. 100 µL human mPGES-1 in KPi-buffer with glutathione. Total protein concentration: 0.02 mg/mL.
2. 1 µL inhibitor in DMSO. Incubation of the plate at room temperature for 25 minutes.
3. 4 µL of a 0.25 mM $PGH_2$ solution. Incubation of the plate at room temperature for 60 seconds.
4. 100 µL stop solution.

180 µL per sample is analyzed with HPLC.

EXAMPLES

The invention is illustrated by way of the following examples, in which the following abbreviations may be employed:

| | |
|---|---|
| dba | dibenzylideneacetone |
| DIBAL | diisobutylalumiuium hydride |
| DMAP | 4,4-dimethylaminopyridine |
| DMF | dimethylformamide |
| DMSO | dimethylsulfoxide |
| EtOAc | ethyl acetate |
| HPLC | High Pressure Liquid Chromatography |
| MeCN | acetonitrile |
| MS | mass spectrum |
| NMR | nuclear magnetic resonance |
| TFA | trifluoroacetic acid |
| THF | tetrahydrofuran |
| xantphos | 9,9-dimethyl-4,5-bis(diphenylphosphino)-xanthene |

Starting materials and chemical reagents specified in the syntheses described below are commercially available from, e.g. Sigma-Aldrich Fine Chemicals.

The term "light petrol" when used herein refers to petroleum ether (40-60° C.).

Example 1

5-(4-tert-Butylphenyl)-1-(4-isopropoxphenyl)-indole-2-carboxylic acid (a) 5-(4-tert-t-Butylphenyl)indole-2-carboxylic acid ethyl ester A mixture of 5-bromoindole-2-carboxylic acid ethyl ester (3.48 g, 13 mmol), 4-tert-butylphenylboronic acid (4.63 g, 26 mmol), $K_3PO_4$ (9.93 g, 45 mmol), $Pd(OAc)_2$ (146 mg, 0.65 mmol), tri-o-tolylphosphine (396 mg, 1.3 mmol), EtOH (20 ml) and toluene (10 mL) was stirred under argon for 20 min at room temperature, and then heated at 100° C. for 24 h. The mixture was allowed to cool, poured into $NaHCO_3$ (aq., sat.) and extracted with EtOAc. The combined extracts were washed with water and brine and then dried over $Na_2SO_4$. Concentration and purification by chromatography gave the sub-title compound (3.27 g, 78%).

(b) 5-(4-tert-Butylphenyl)-1-(4-isopropoxyphenyl)indole-2-carboxylic acid ethyl ester 5-(4-tert-Butylphenyl)indole-2-carboxylic acid ethyl ester (198 mg, 0.60 mmol; see step (a) above), CuI (12 mg, 0.06 mmol), $K_3PO_4$ (254 mg, 1.2 mmol), N,N'-dimethyl-1,2-diaminoethane (20 µL, 0.18 mmol) and 1-bromo-4-isopropoxybenzene (258 mg, 1.2 mmol) in toluene (2 mL) was heated at 110° C. for 17 h. The mixture was diluted with EtOAc and washed with $NaHCO_3$ (aq. sat.), HCl (aq. 0.1 M), brine and then dried over $Na_2SO_4$. Concentration and purification by chromatography gave the sub-title compound (260 mg, 94%).

(c) 5-(4-tert-Butylphenyl)-1-(4-isopropoxyphenyl)-indole-2-carboxylic acid

A mixture of 5-(4-tert-butylphenyl)-1-(4-isopropoxyphenyl)indole-2-carboxylic acid ethyl ester (259 mg, 0.57 mmol; see step (b)), NaOH (114 mg, 2.85 mmol), water (0.6 mL) and dioxane (3 mL) was heated using microwave irradiation for 1 h at 120° C. An additional portion of NaOH (100 mg) was added and heating was continued for another 30 min at 120° C. After cooling, the reaction was acidified with HCl (1M) to pH 2 and extracted with EtOAc. The combined extracts were washed with water, brine and dried over $Na_2SO_4$ and purified by chromatography to give the title compound (165 mg, 60%).

200 MHz $^1$H-NMR (DMSO-$d_6$, ppm) δ 7.96 (1H, s), 7.62-7.50 (3H, m), 7.49-7.36 (3H, m), 7.30-7.20 (2H, m), 7.10-6.96 (3H, m), 4.67 (1H, septet, J=6.0 Hz), 1.32 (6H, d, J=6.0 Hz), 1.30 (9H, s).

Example 2

1,6-Bis(4-isopropoxyphenyl)-indole-2-carboxylic acid

The title compound was prepared in accordance with Example 1, using 6-bromoindole-2-carboxylic acid ethyl ester, 4-isopropoxyphenylboronic acid and 4-bromo-1-isopropoxybenzene.

200 MHz $^1$H-NMR (DMSO-$d_6$, ppm) δ 7.77 (1H, d, J=8.3 Hz), 7.50-7.22 (6H, m), 7.11-6.87 (5H, m), 4.67 (1H, septet, J=6.0 Hz), 4.59 (1H, septet, J=6.0 Hz), 1.31 (6H, d, J=6.0 Hz), 1.24 (6H, d, J=6.0 Hz).

Example 3

1,5-Bis(4-isopropoxyphenyl)-indole-2-carboxylic acid

The title compound was prepared in accordance with Example 1, using 5-bromoindole-2-carboxylic acid ethyl ester, 4-isopropoxyphenylboronic acid and 4-bromo-1-isopropoxybenzene.

200 MHz $^1$H-NMR (DMSO-$d_6$, ppm) δ 12.8 (1H, br s), 7.93 (1H, d, J=1.6 Hz), 7.61-7.49 (3H, m), 7.39 (1H, s), 7.31-7.22 (2H, m), 7.09-6.95 (5H, m), 4.69 (1H, septet, J=6.0 Hz), 4.64 (1H, septet, J=6.0 Hz), 1.33 (6H, d, J=6.0 Hz), 1.28 (6H, d, J=6.0 Hz).

Example 4

1,5-Bis(4-isopropoxyphenyl)-4-nitroindole-2-carboxylic acid (a) 1,5-Bis(4-isopropoxyphenyl)indole-2-carboxylic acid ethyl ester The sub-title compound was prepared in accordance with Example 1(b), using 5-bromoindole-2-carboxylic acid ethyl ester, 4-isopropoxyphenylboronic acid and 4-bromo-1-isopropoxybenzene.

(b) 1,5-Bis(4-isopropoxyphenyl)-4-nitroindole-2-carboxylic acid ethyl ester $Cu(NO_3)_2$×2.5 $H_2O$ (230 mg, 0.99 mmol), whilst stirring, was added to $Ac_2O$ (5 mL) at −5° C. This was followed by the dropwise addition of 1,5-bis(4-isopropoxyphenyl)indole-2-carboxylic acid ethyl ester (570 mg, 1.24 mmol; see step (a)) in $Ac_2O$ (10 mL). After 2 h at room temperature, the solid was filtered off and washed with Ac$_2$O. The combined filtrates were poured onto ice and stirred for 18 h. The solid was collected and purified by chromatography to yield the sub-title compound (335 mg, 54%).

(c) 1,5-Bis(4-isopropoxyphenyl)-4-nitroindole-2-carboxylic acid

The title compound was prepared by hydrolysis of 1,5-bis (4-isopropoxyphenyl)-4-nitroindole-2-carboxylic acid ethyl ester in accordance with the procedure described in Example 1(c).

200 MHz $^1$H-NMR (DMSO-d$_6$, ppm) δ 13.3 (1H, br s), 7.39-7.28 (5H, m), 7.28-7.20 (2H, m), 7.09-6.93 (4H, m), 4.69 (1H, septet, J=6.0 Hz), 4.64 (1H, septet, J=6.0 Hz), 1.31 (6H, d, J=6.0 Hz), 1.27 (6H, d, J=6.0 Hz).

Example 5

4-Amino-1,5-bis(4-isopropoxyphenyl)2-carboxylic acid hydrochloride

(a) 4-Amino-1,5-bis(4-isopropoxyphenyl)indole-2-carboxylic acid ethyl ester A stirred mixture of 1,5-bis(4-isopropoxyphenyl)-4-nitroindole-2-carboxylic acid ethyl ester (335 mg, 0.67 mmol; see Example 4(b)) and Pd/C (10%, 120 mg) in EtOAc was hydrogenated at ambient pressure and temperature for 10 h and filtered through Celite®. The filter cake was washed with EtOAc and the combined filtrates were concentrated and purified by chromatography to yield the sub-title compound (272 mg, 86%).

(b) 4-Amino-1,5-bis(4-isopropoxyphenyl)indole-2-carboxylic acid hydrochloride A mixture of 4-amino-1,5-bis(4-isopropoxyphenyl)indole-2-carboxylic acid ethyl ester (160 mg, 340 nmol; see step (a)), acetonitrile (5 mL), and aqueous NaOH (1M, 2 mL) was heated at reflux for 3 h, and then allowed to cool. The pH was adjusted to 7 with 1 M HCl, and the mixture extracted with EtOAc. The combined extracts were washed with brine, dried over Na$_2$SO$_4$, concentrated, purified by chromatography, and dissolved in Et$_2$O/absolute ethanol (3 mL). 4M HCl (100 µL) in dioxane was added. The precipitate was filtered off, washed with Et$_2$O, and dried to yield the title compound (124 mg, 86%).

200 MHz $^1$H-NMR (DMSO-d$_6$, ppm) δ 7.75-7.71 (1H, m), 7.41-7.32 (2H, m), 7.29-7.19 (2H, m), 7.12-6.96 (5H, m), 6.72-6.54 (1H, m), 4.68 (1H, septet, J=5.7 Hz), 4.66 (1H, septet, J=5.7 Hz), 1.33 (6H, d, J=5.7 Hz), 1.30 (6H, d, J=5.7 Hz).

Example 6

4-Acetamido-1,5-bis(4-isopropoxyphenyl)-indole-2-carboxylic acid

(a) 4-Acetamido-1,5-bis(4-isopropoxyphenyl)indole-2-carboxylic acid ethyl ester A mixture of 4-amino-1,5-bis(4-isopropoxyphenyl)indole-2-carboxylic acid ethyl ester (160 mg, 0.34 mmol; see Example 5(a)), acetyl chloride (50 mg, 0.63 mmol), Et$_3$N (63 mg, 0.63 mmol) and MeCN (10 mL) was stirred at room temperature for 30 minutes, then poured into HCl (1M) and extracted with EtOAc. The combined extracts were washed with water and brine, and dried over Na$_2$SO$_4$. Concentration and purification by chromatography gave the sub-title compound (182 mg, 84%).

(b) 4-Acetamido-1,5-bis(4-isopropoxyphenyl)indole-2-carboxylic acid

The title compound (23 mg, 49%) was prepared by hydrolysis of 4-acetamido-1,5-bis(4-isopropoxyphenyl)indole-2-carboxylic acid ethyl ester (see step (a)) in accordance with the procedure described in Example 1(c).

200 MHz $^1$H-NMR (DMSO-d$_6$, ppm) δ 12.8-12.7 (1H, br s), 9.58 (1H, s) 7.33-7.20 (5H, m), 7.14 (1H, s), 7.09-7.01 (2H, m), 7.00-6.91 (3H, m), 4.70 (1H, septet, J=6.0 Hz), 4.64 (1H, septet, J=6.0 Hz), 2.01 (3H, s), 1.34 (6H, d, J=6.0 Hz), 1.29 (6H, d, J=6.0 Hz).

Example 7

1-(4-Isopropoxyphenyl)-5-(4-(trifluoromethyl)phenyl)-indole-2-carboxylic acid The title compound was prepared in accordance with Example 1, using 5-bromoindole-2-carboxylic acid ethyl ester, 4-(trifluoromethyl)phenyl-boronic acid and 4-bromo-1-isopropoxybenzene.

200 MHz $^1$H-NMR (CDCl$_3$, ppm) δ 8.01-7.94 (1H, m), 7.80-7.66 (4H, m), 7.31-7.14 (5H, m), 7.62-7.50 (2H, m), 4.65 (1H, septet, J=5.8 Hz), 1.44 (6H, d, J=5.8).

Example 8

1-(4-Isopropoxyphenyl)-5-(5-(trifluoromethyl)pyrid-2-yl)indole-2-carboxylic acid

(a) 5-(4,4,5,5-Tetramethyl-1,3,2-dioxaborolan-2-yl)indole-2-carboxylic acid ethyl ester A mixture prepared from Pd$_2$(dba)$_3$ (0.229 g, 0.25 mmol), tricyclohexylphosphine (0.421 g, 1.5 mmol) and dioxane (25 mL) was added under argon to a stirred mixture of 5-bromoindole-2-carboxylic acid ethyl ester (1.94 g, 7.2 mmol), KOAc (1.10 g, 11 mmol), bis(pinacolato)diboron (2.00 g, 7.9 mmol) and dioxane (25 mL) at 80° C. After 2 h at 80° C. another portion (16 mL) of the mixture prepared from Pd$_2$(dba)$_3$, tricyclohexylphosphine and dioxane, as described herein, was added and the resulting mixture stirred at 80° C. for 16 h. The mixture was allowed to cool and filtered through Celite®. The filter cake was washed with EtOAc and the combined filtrates were concentrated and purified by chromatography to yield the sub-title compound (1.10 g, 46%).

(b) 5-(5-(Trifluoromethyl)pyrid-2-yl)indole-2-carboxylic acid ethyl ester

A stirred mixture of 5-(4,4,5,5-tetramethyl-1,3,2-dioxaborolan-2-yl)indole-2-carboxylic acid ethyl ester (300 mg, 0.95 mmol; see step (a)), 2-bromo-5-(trifluoromethyl)pyridine (323 mg, 1.43 mmol), sodium carbonate (2M, 1.43 mL, 2.85 mmol), Pd(PPh$_3$)$_4$ (54 mg, 0.05 mmol), EtOH (5 mL) and toluene (20 mL) was heated at 80° C. for 2 h. Another portion of Pd(PPh$_3$)$_4$ (54 mg, 0.05 mmol) was added and the heating continued for 16 h. The mixture was diluted with EtOAc, washed with brine, dried over MgSO$_4$, concentrated and purified by chromatography to give the sub-title compound (247 mg, 77%).

(c) 1-(4-Isopropoxyphenyl)-5-(5-(trifluoromethyl) pyrid-2-yl)indole-2-carboxylic acid ethyl ester Anhydrous $CH_2Cl_2$ (10 mL), followed by $Et_3N$ (92 μL, 0.66 mmol), pyridine (54 μL, 0.66 mmol) and 3 Å molecular sieves (1 g) were added to a mixture of 5-(5-(trifluoromethyl) pyrid-2-yl)indole-2-carboxylic acid ethyl ester (110 mg, 1.33 mmol; see step (b)), $Cu(OAc)_2$ (120 mg, 0.66 mmol), and 4-isopropoxyphenylboronic acid (119 mg, 0.66 mmol). The mixture was stirred vigorously at ambient temperature for 18 h after which additional $Cu(OAc)_2$ (59.9 mg, 0.33 mmol), 4-isopropoxyphenylboronic acid (59.4 mg, 0.33 mmol), $Et_3N$ (46.4 μL, 0.33 mmol) and pyridine (27 μL, 0.33 mmol) were added. After a further 30 h of stirring, the mixture was filtered through Celite®. The filter cake was washed with EtOAc and the solvents concentrated and purified by chromatography to give the sub-title compound.

(d) 1-(4-Isopropoxyphenyl)-5-(5-(trifluoromethyl) pyrid-2-yl)indole-2-carboxylic acid The title compound was prepared by hydrolysis of 1-(4-isopropoxyphenyl)-5-(4-(trifluoromethyl)pyrid-2-yl)indole-2-carboxylic acid ethyl ester (see step (c)) in accordance with the procedure described in Example 1(c).

200 MHz $^1$H-NMR (DMSO-$d_6$, ppm) δ 9.03 (1H, m), 8.62-8.56 (1H, m), 8.29-8.17 (2H, m), 8.10 (1H, dd, J=1.4, 8.8 Hz), 7.46 (1H, s), 7.32-7.23 (2H, m), 7.12 (1H, d, J=8.8 Hz), 7.07-6.99 (2H, m), 4.69 (1H, septet, J=6.2 Hz), 1.32 (6H, d, J=6.2 Hz).

Example 9

1-(4-Isopropoxyphenyl-5-(6-isopropoxypyrid-3-yl) indole-2-carboxylic acid

(a) 5-(6-Isopropoxypyrid-3-yl)indole-2-carboxylic acid ethyl ester

The sub-title compound was prepared in accordance with Example 8(b), using 5-bromo-2-isopropoxypyridine instead of 2-bromo-5-(trifluoromethyl)pyridine.

(b) 1-(4-Isopropoxyphenyl)-5-(6-isopropoxypyrid-3-yl)indole-2-carb-oxylic acid ethyl ester A mixture of CuI (7.14 mg, 51 mmol), N,N'-dimethyl-1,2-diaminoethane (16.7 μL, 0.153 mmol) and toluene (0.5 mL) was added to a mixture of 5-(6-isopropoxypyrid-3-yl)indole-2-carboxylic acid ethyl ester (165 mg, 0.510 mmol; see step (a)), 1-bromo-4-isopropoxybenzene (219 mg, 1.02 mmol), $K_3PO_4$ (108 mg, 0.510 mmol) and toluene (2 mL) under argon. The mixtures was heated at 110° C. for 5 h and at 140° C. for 16 h, then allowed to cool to room temperature and filtered through Celite®. The filter cake was washed with EtOAc and the combined filtrates were concentrated and purified by chromatography to give the sub-title compound (163 mg, 70%).

(c) 1-(4-Isopropoxyphenyl)-5-(6-isopropoxypyrid-3-yl)indole-2-carb-oxylic acid The title compound was prepared by hydrolysis of 1-(4-isopropoxyphenyl)-5-(6-isopropoxypyrid-3-yl)indole-2-carboxylic acid ethyl ester (see step (b)) in accordance with the procedure described in Example 1(c).

200 MHz $^1$H-NMR (DMSO-$d_6$, ppm) δ 8.43 (1H, d, J=2.2 Hz), 8.00-7.92 (2H, m), 7.54-7.46 (1H, m), 7.32-7.20 (3H, m), 7.06-6.98 (3H, m), 6.84-6.77 (1H, m), 5.27 (1H, septet, J=6.2 Hz), 4.67 (1H, septet, J=6.2 Hz), 1.32 (6H, d, J=6.2 Hz), 1.30 (6H, d, J=6.2 Hz).

Example 10

1-(4-Methoxyphenyl)-5-(4-(trifluoromethoxy)phenyl)indole-2-carboxylic acid

The title compound was prepared from 5-(4-(trifluoromethoxy)-phenyl)indole-2-carboxylic acid ethyl ester (prepared in accordance with Example 1(a) from 5-bromoindole-2-carboxylic acid ethyl ester and 4-(trifluoromethoxy) phenylboronic acid) and 1-bromo-4-methoxybenzene in accordance with the procedure described in Example 9(b), followed by hydrolysis in accordance with the procedure described in Example 1(c).

200 MHz $^1$H-NMR (DMSO-$d_6$, ppm) δ 12.8 (1H, br s), 8.03 (1H, d, J=1.7 Hz), 7.83-7.73 (2H, m), 7.57 (1H, dd, J=8.8, 1.7 Hz), 7.48-7.38 (2H, m), 7.41 (1H, s), 7.34-7.25 (2H, m), 7.11-7.03 (3H, m), 3.83 (3H, s).

Example 11

1-(4-Ethoxyphenyl)-5-(4-(trifluoromethoxy)phenyl) indole-2-carboxylic acid

The title compound was prepared in accordance with Example 10 using 1-bromo-4-ethoxybenzene instead of 1-bromo-4-methoxybenzene.

200 MHz $^1$H-NMR (DMSO-$d_6$, ppm) δ 12.8 (1H, br s), 8.03 (1H, d, J=1.8 Hz), 7.83-7.73 (2H, m), 7.57 (1H, dd, J=8.9, 1.8 Hz), 7.48-7.38 (2H, m), 7.41 (1H, s), 7.32-7.23 (2H, m), 7.10-7.02 (2H, m), 7.04 (1H, d, J=8.9 Hz), 4.10 (2H, q, J=7.0 Hz), 1.37 (3H, t, J=7.0 Hz).

Example 12

1-(4-Isopropoxyphenyl)-5-(4-(trifluoromethoxy) phenyl)indole-2-carboxylic acid The title compound was prepared in accordance with Example 10 using 1-bromo-4-isopropoxybenzene instead of 1-bromo-4-methoxybenzene.

200 MHz $^1$H-NMR (DMSO-$d_6$, ppm) δ 12.8 (1H, br s), 8.02 (1H, d, J=1.8 Hz), 7.83-7.73 (2H, m), 7.56 (1H, dd, J=8.9, 1.8 Hz), 7.48-7.38 (2H, m), 7.39 (1H, s), 7.30-7.21 (2H, m), 7.08 (1H, d, J=8.9 Hz), 7.06-6.98 (2H, m), 4.68 (1H, septet, J=6.0 Hz), 1.32 (6H, t, J=6.0 Hz).

Example 13

1-(4-Isobutoxyphenyl)-5-(4-(trifluoromethoxy)phenylindole-2-carboxylic acid

(a) 1-Bromo-4-isobutoxybenzene 4-bromophenol (2.4 g, 13.8 mmol), 1-iodo-2-methylpropane (3.45 mL, 20 mmol), sodium hydroxide (0.8 g, 20 mmol) and DMF (2 mL) were allowed to react to yield the sub-title compound (615 mg, 19%).

(b) 1-(4-Isobutoxyphenyl)-5-(4-(trifluoromethoxy) phenyl)indole-2-carboxylic acid The title compound was prepared in accordance with Example 10 using 1-bromo-4-isobutoxybenzene instead of 1-bromo-4-methoxybenzene.

200 MHz $^1$H-NMR (DMSO-d$_6$, ppm) δ 12.8 (1H, br s), 8.03 (1H, d, J=1.7 Hz), 7.83-7.74 (2H, m), 7.57 (1H, dd, J=8.8, 1.7 Hz), 7.47-7.39 (2H, m), 7.41 (1H, s), 7.31-7.23 (2H, m), 7.11-7.03 (2H, m), 7.05 (1H, d, J=8.8 Hz), 3.82 (2H, d, J=6.4 Hz), 2.16-1.95 (1H, m), 1.01 (6H, d, J=6.8 Hz).

Example 14

1-(4-Cyclobutylmethoxy-phenyl)-5-(4-(trifluoromethoxy)phenyl)indole-2-carboxylic acid (a) 1-Bromo-4-(cyclobutylmethoxy)benzene 4-Bromophenol (2.5 g, 14.5 mmol), (bromomethyl)cyclobutane (1.6 mL, 15 mmol), sodium hydroxide (0.8 g, 20 mmol) and DMF (3 mL) were allowed to react to yield the sub-title compound (1.3 g, 36%).

(b) 1-(4-Cyclobutylmethoxy)phenyl)-5-(4-(trifluoromethoxy)phenyl)indole-2-carboxylic acid The title compound was prepared in accordance with Example 10 using 1-bromo-4-(cyclobutylmethoxy)benzene instead of 1-bromo-4-methoxybenzene.
200 MHz $^1$H-NMR (DMSO-d$_6$, ppm) δ 12.8 (1H, br s), 8.03 (1H, d, J=1.8 Hz), 7.83-7.74 (2H, m), 7.57 (1H, dd, J=8.8, 1.8 Hz), 7.48-7.39 (2H, m), 7.41 (1H, s), 7.32-7.23 (2H, m), 7.11-7.02 (2H, m), 7.05 (1H, d, J=8.8 Hz), 4.02 (2H, d, J=6.7 Hz), 2.85-2.67 (1H, m), 2.17-1.76 (6H, m).

Example 15

5-(4-Isopropoxyphenyl)-1-phenylindole-2-carboxylic acid

The title compound was prepared in accordance with Example 10 using 5-(4-isopropoxyphenyl)indole-2-carboxylic acid ethyl ester and iodobenzene.
200 MHz $^1$H-NMR (DMSO-d$_6$, ppm) δ 12.9-12.8 (1H, br s), 7.83 (1H, s), 7.61-7.44 (6H, m), 7.43-7.32 (3H, m), 7.10-6.92 (3H, m), 4.63 (1H, septet, J=6.0 Hz), 1.27 (6H, d, J=6.0 Hz).

Example 16

1-(5-(Ethoxymethyl)pyrid-2-yl)-5-(4-isopropoxyphenyl)indole-2-carboxylic acid

The title compound was prepared in accordance with Example 10 using 5-(4-isopropoxyphenyl)indole-2-carboxylic acid ethyl ester and 2-chloro-5-(ethoxymethyl)pyridine.
200 MHz $^1$H-NMR (DMSO-d$_6$, ppm) δ 13.0 (1H, br s), 8.52 (1H, s), 7.98-7.87 (2H, m), 7.62-7.44 (4H, m), 7.39-7.29 (2H, m), 7.02-6.92 (2H, m), 4.63 (1H, septet, J=6.1 Hz), 4.57 (2H, s), 3.56 (2H, q, J=7.0 Hz), 1.26 (6H, d; J=6.1 Hz), 1.18 (3H, t, J=7.0 Hz).

Example 17

5-(4-Isopropoxyphenyl)-1-(6-isopropoxypyrid-3-yl)indole-2-carboxylic acid

The title compound was prepared in accordance with Example 10 using 5-(4-isopropoxyphenyl)indole-2-carboxylic acid ethyl ester and 5-bromo-2-isopropoxypyridine.
200 MHz $^1$H-NMR (DMSO-d$_6$, ppm) δ 12.9 (1H, br s), 8.18 (1H, d, J=2.8 Hz), 7.94 (1H, s), 7.74 (1H, dd, J=8.8, 2.8 Hz), 7.61-7.49 (3H, m), 7.45 (1H, s), 7.08 (1H, d, J=8.8 Hz), 7.03-6.93 (2H, m), 6.88 (1H, d, J=8.8 Hz), 5.30 (1H, septet, J=6.2 Hz), 4.64 (1H, septet, J=6.0 Hz), 1.35 (6H, d, J=6.2 Hz), 1.27 (6H, dt, J=6.0 Hz).

Example 18

5-(4-Isopropoxyphenyl)-1-(2-naphthyl)indole-2-carboxylic acid (a) 5-(4-Isopropoxyphenyl)indole-2-carboxylic acid ethyl ester The sub-title compound was prepared in accordance with Example 1(a) form 5-bromoindole-2-carboxylic acid ethyl ester and 4-isopropoxyphenylboronic acid.

(b) 5-(4-Isopropoxyphenyl)-1-(2-naphthyl)indole-2-carboxylic acid

The title compound was prepared in accordance with Example 8(c) from 5-(4-isopropoxyphenyl)indole-2-carboxylic acid ethyl ester (see step (a) above) and 2-naphthylboronic acid followed by hydrolysis in accordance with the procedure described in Example 1(c).
200 MHz $^1$H-NMR (DMSO-d$_6$, ppm) δ 12.9-12.8 (1H, br s), 8.07-7.96 (5H, m), 7.62-7.45 (7H, m), 7.12 (1H, d, J=8.8 Hz), 7.01-6.95 (2H, m), 4.62 (1H, septet, J=6.0 Hz), 1.26 (6H, d, J=6.0 Hz).

Example 19

Sodium 5-(4-isopropoxyphenyl)-1-(2-naphthyl)indole-2-carboxylate 5-(4-Isopropoxyphenyl)-1-(2-naphthyl)indole-2-carboxylic acid (40 mg, 0.095 mmol; see Example 18) was dissolved in dry THF (1 mL) and NaOMe (3.37 M, 28 μL) was added via syringe. After stirring for 30 min at room temperature, the solvents were removed under reduced pressure and the residue dried in vacuo to yield the title compound (42 mg, 99%).

Example 20

5-(4-tert-Butylphenyl)-1-(4-(trifluoromethoxy)phenyl)indole-2-carboxylic acid

The title compound was prepared in accordance with Example 8(c) using 5-(4-tert-butylphenyl)indole-2-carboxylic acid ethyl ester and 4-(trifluoromethoxy)phenylboronic acid, followed by hydrolysis in accordance with the procedure described in Example 1(c).
200 MHz $^1$H-NMR (DMSO-d$_6$, ppm) δ 12.92 (1H, s), 7.99 (1H, d, J=1.1 Hz), 7.60-7.53 (7H, m), 7.47-7.43 (3H, m), 7.09 (1H, d, J=8.8 Hz), 1.29 (9H, s).

Example 21

5-(4-tert-Butylphenyl)-1-(4-(methylsulfonyl)phenyl)indole-2-carboxylic acid

The title compound was prepared in accordance with Example 8(c) using 5-(4-tert-butylphenyl)indole-2-carboxylic acid ethyl ester and 4-(methylsulfonyl)phenylboronic acid, followed by hydrolysis in accordance with the procedure described in Example 1(c).
200 MHz $^1$H-NMR (DMSO-d$_6$, ppm) δ 13.03 (1H, s), 8.12-8.05 (2H, m), 8.02 (1H, d, J=1.2 Hz), 7.74-7.67 (2H, m), 7.62-7.57 (3H, m), 7.51-7.44 (3H, m), 7.18 (1H, d, J=8.8 Hz), 3.34 (3H, s), 1.30 (9H, s).

Example 22

5-(4-tert-Butylphenyl)-1-(4-methyl-3-nitrophenyl) indole-2-carboxylic acid

The title compound was prepared in accordance with Example 1 using 5-(4-tert-butylphenyl)indole-2-carboxylic acid ethyl ester and 4-bromo-1-methyl-2-nitrobenzene.

200 MHz $^1$H-NMR (DMSO-$d_6$, ppm) δ 13.02 (1H, br s), 8.08 (1H, d, J=1.8 Hz), 8.03-8.02 (1H, m), 7.73 (1H, dd, J=8.2, 1.8 Hz), 7.69 (1H, s), 7.65-7.58 (3H, m), 7.50-7.45 (3H, m), 7.18 (1H, d, J=8.8 Hz), 2.62 (3H, s), 1.31 (9H, s).

Example 23

5-(4-tert-Butylphenyl)-1-(4-(trifluoromethyl)phenyl) indole-2-carboxylic acid

The title compound was prepared in accordance with Example 8(c) using 5-(4-tert-butylphenyl)indole-2-carboxylic acid ethyl ester and 4-(trifluoromethyl)phenylboronic acid, followed by hydrolysis in accordance with the procedure described in Example 1(c).

200 MHz $^1$H-NMR (DMSO-$d_6$, ppm) δ 12.99 (1H, s), 8.02-8.01 (1H, m), 7.93-7.89 (2H, m), 7.68-7.56 (5H, m), 7.49-7.44 (3H, m), 7.16 (1H, d, J=8.8 Hz), 1.30 (9H, s).

Example 24

5-(4-tert-Butylphenyl)-1-(6-isopropoxy-2-naphthyl) indole-2-carboxylic acid

The title compound was prepared in accordance with Example 1 using 5-(4-tert-butylphenyl)indole-2-carboxylic acid ethyl ester and 2-bromo-6-isopropoxynaphthalene.

200 MHz $^1$H-NMR (DMSO-$d_6$, ppm) δ 13.2-12.4 (1H, br s), 8.00 (1H, d, J=1.4 Hz), 7.93-7.87 (3H, m), 7.61-7.51 (3H, m), 7.47-7.37 (5H, m), 7.20 (1H, dd, J=9.0, 2.4 Hz), 7.11 (1H, d, J=8.8 Hz), 4.81 (1H, septet, J=6.1 Hz), 1.35 (6H, d, J=6.1 Hz), 1.29 (9H, s).

Example 25

Sodium 5-(4-tert-butylphenyl)-1-(4-nitrophenyl) indole-2-carboxylate 5-(4-tert-Butylphenyl)-1-(4-nitrophenyl)indole-2-carboxylic acid ethyl ester was prepared in accordance with Example 1 using 5-(4-tert-butylphenyl)indole-2-carboxylic acid ethyl ester and 1-bromo-4-nitrobenzene. This ester (207 mg, 0.47 mmol) was dissolved in dioxane (2 mL) to which aqueous NaOH (1M, 1 mL) was added. The mixture was heated using microwave irradiation at 120° C. for 15 min and allowed to cool. The precipitate was filtered off, washed with water and recrystallised from EtOH/EtOAc to yield the title compound.

200 MHz $^1$H-NMR (DMSO-$d_6$, ppm) δ 8.34-8.26 (2H, m), 7.85-7.84 (1H, m), 7.62-7.56 (4H, m), 7.45-7.39 (3H, m), 7.20 (1H, d, J=8.6 Hz), 6.95 (1H, s), 1.30 (9H, s).

Example 26

Sodium 5-(4-tert-butylphenyl)-1-(4-(4-methylpiperazin-1-ylsulfonyl)phenyl)indole-2-carboxylate (a) 1-(4-Bromophenylsulfonyl)-4-methylpiperazine 4-Bromobenzene-1-sulfonyl chloride (2.56 g, 10 mmol) in anhydrous CH$_2$Cl$_2$ (10 mL) was added to a mixture of 1-methylpiperazine (2.0 g, 20 mmol), pyridine (2.37 g, 30 mmol) and anhydrous CH$_2$Cl$_2$ (10 mL) at 0° C. The mixture was stirred at room temperature for 16 h, concentrated, recrystallised, and dried over P$_2$O$_5$ to yield the sub-title compound (2.27 g, 71%).

(b) Sodium 5-(4-tert-butylphenyl)-1-(4-(4-methylpiperazin 1-ylsulfonyl)-phenyl)indole-2-carboxylate 5-(4-tert-Butylphenyl) 1-(4-(4-methylpiperazin-1-ylsulfonyl)phenyl)indole-2-carboxylic acid ethyl ester was prepared in accordance with Example 1 using 5-(4-tert-butylphenyl)indole-2-carboxylic acid ethyl ester and 1-(4-bromophenylsulfonyl)-4-methylpiperazine (see step (a)). The title compound was prepared by hydrolysis and precipitation in accordance with the procedure described in Example 25.

200 MHz $^1$H-NMR (DMSO-$d_6$, ppm) δ 7.86 (1H, d, J=1.1 Hz), 7.83-7.77 (2H, m), 7.61-7.56 (4H, m), 7.48-7.40 (3H, m), 7.17 (1H, d, J=8.8 Hz), 6.96 (1H, s), 2.99-2.95 (4H, m), 2.42-2.38 (4H, m), 2.16 (3H, s), 1.32 (9H, s).

Example 27

5-(4-tert-Butylphenyl)-1-(4-(2-carboxyvinyl)phenyl) indole-2-carboxylic acid a) (E)-3-(4-Bromophenyl)acrylic acid ethyl ester Ph$_3$P=CHCO$_2$Et (6.2 g, 17.8 mmol) was added to 4-bromobenzaldehyde (3.0 g, 16.2 mmol) in anhydrous DMF (20 mL) at room temperature. The mixture stirred for 2 h, washed with water and extracted with EtOAc. The combined extracts were washed with brine, dried over Na$_2$SO$_4$, concentrated and purified by chromatography and distillation to give the sub-title compound (2.99 g, 72%).

(b) 5-(4-tert-Butylphenyl)-1-(4-(2-carboxyvinyl) phenyl)indole-2-carboxylic acid The title compound was prepared in accordance with Example 1 using 5-(4-tert-butylphenyl)indole-2-carboxylic acid ethyl ester and (E)-3-(4-bromophenyl)acrylic acid ethyl ester.

200 MHz $^1$H-NMR (DMSO-$d_6$, ppm) δ 7.98-7.97 (1H, m), 7.86-7.80 (2H, m), 7.69 (1H, d, J=16.0 Hz), 7.63-7.52 (3H, m), 7.50-7.40 (4H, m), 7.35 (1H, s), 7.16 (1H, d, J=8.8 Hz), 6.64 (1H, d, J=16.0 Hz), 1.32 (9H, s).

Example 28

5-(4-tert-Butylphenyl-1-(4-(2-carboxypropan-2-yloxy)phenyl)indole-2-carboxylic acid (a) 2-(4-Bromophenoxy)-2-methylpropanoic acid Finely crushed NaOH pellets (23.0 g, 576 mmol) were added in portions to 4-bromophenol (10.4 g, 60 mmol) in acetone (146 mL, 1980 mmol) keeping the temperature below 28° C. CHCl$_3$ (13 mL, 161 mmol)) was added dropwise keeping the temperature below 35° C. and the mixture was stirred at that temperature for 30 min, then at reflux for 3 h and at room temperature for 18 h. The mixture was then concentrated and the residue was diluted with water, cooled in an ice-bath and acidified with HCl (6M). The precipitate was allowed to settle and was collected by decantation. Water was added to the solid and the mixture was stirred vigorously for 5 min and then filtered. The solid was dried to give the sub-title compound (14.0 g, 91%).

(b) 2-(4-Bromophenoxy)-2-methylpropanoyl chloride

A mixture of 2-(4-bromophenoxy)-2-methylpropanoic acid (10.0 g, 38.6 mmol). DMF (0.5 mL) and $SOCl_2$ (40 mL) was heated for 3 h, allowed to cool and distilled to yield the sub-title compound (8.4 g, 78%).

(c) 2-(4-Bromophenoxy)-2-methylpropanoic acid methyl ester 2-(4-Bromophenoxy)-2-methylpropanoyl chloride (2.34 g, 8.4 mmol) in THF (10 mL) was added dropwise whilst stirring to anhydrous MeOH (1.34 g, 42 mmol), $Et_3N$ (1.7 g, 16.8 mmol) and THF at 0° C. The mixture was stirred at room temperature for 3 h, concentrated and distilled to afford the sub-title compound (1.74 g, 97%).

(d) 5-(4-tert-Butylphenyl-1-(4-(2-carboxypropan-2-yloxy)phenyl)indole-2-carboxylic acid The title compound was prepared in accordance with Example 1 using 5-(4-tert-butylphenyl)indole-2-carboxylic acid ethyl ester and 2-(4-bromophenoxy)-2-methylpropanoic acid methyl ester.

200 MHz $^1$H-NMR (DMSO-$d_6$, ppm) δ 7.89-7.88 (1H, m), 7.60-7.55 (2H, m), 7.46-7.41 (3H, m), 7.17-7.13 (3H, m), 7.02 (1H, d, J=8.6 Hz), 6.93-6.87 (2H, m), 1.52 (6H, s), 1.31 (9H, s).

Example 29

5-(4-tert-Butylphenyl)-1-(4-(2-methyl-1-(pyrrolidin-1-yl)propan-2-yloxy)phenyl)indole-2-carboxylic acid (a) 2-(4-Bromophenoxy)-2-methyl-1-(pyrrolidin-1-yl)propan-1-one Pyrrolidine (1.54 g, 21.6 mmol) in anhydrous MeCN (10 mL) was added with stirring to 2-(4-bromophenoxy)-2-methylpropanoyl chloride (2 g, 7.2 mmol) in anhydrous MeCN (10 mL) at 0° C. The mixture was stirred at room temperature for 18 h and acidified with HCl (aq. 1M, 40 mL). Brine was added and the mixture was extracted with $CH_2Cl_2$. The combined extracts were washed with $NaHCO_3$ (aq. sat) and brine, dried ($Na_2SO_4$), and concentrated to give the sub-title compound (2.12 g, 94%).

(b) 1-(2-(4-Bromophenoxy)-2-methylpropyl)pyrrolidine $BH_3 \times THF$ (1M, 27.0 mmol, 27.0 mL) was added dropwise under argon to 2-(4-bromophenoxy)-2-methyl-1-(pyrrolidin-1-yl)propan-1-one (2.12 g, 6.8 mmol; see step (a)) in THF (40 mL) at 0° C. The reaction was quenched by careful addition of $NH_4Cl$ (aq. sat.). The reaction mixture was acidified by HCl (1M). NaOH (aq. 0.5M, 30 mL) was added to the filtrate which was then extracted with $CH_2Cl_2$. The combined extracts were washed with brine, dried ($Na_2SO_4$), concentrated and distilled under reduced pressure to yield the title compound (1.5 g, 76%).

(c) 5-(4-tert-Butylphenyl)-1-(4-(2-methyl-1-(pyrrolidin-1-yl)propan-2-yl-oxy)phenyl)indole-2-carboxylic acid The title compound was prepared in accordance with Example 1 using 5-(4-tert-butylphenyl)indole-2-carboxylic acid ethyl ester and 1-(2-(4-bromophenoxy)-2-methylpropyl)pyrrolidine.

200 MHz $^1$H-NMR (DMSO-$d_6$, ppm) δ 7.97-7.96 (1H, m), 7.62-7.44 (5H, m), 7.35 (1H, s), 7.29-7.24 (2H, m), 7.14-7.06 (3H, m), 2.81 (2H, s), 2.79-2.74 (4H, m), 1.80-1.68 (4H, m), 1.33 (6H, s), 1.32 (9H, s).

Example 30

5-(4-tert-Butylphenyl)-1-(4-(2-methyl-1-(4-methylpiperazin-1-yl)-1-oxopropan-2-yloxy)phenyl)indole-2-carboxylic acid hydrochloride (a) 1-(2-(4-Bromophenoxy)-2-methylpropanoyl)-4-methylpiperazine hydrochloride 1-(2-(4-Bromophenoxy)-2-methylpropanoyl)-4-methylpiperazine was prepared in accordance to the procedure described in Example 29(a) from 2-(4-bromophenoxy)-2-methylpropanoyl chloride and 1-methylpiperazine (5.3 mL, 17.5 mmol). This compound (2.37 g, 6.95 mmol) was dissolved in $Et_2O$ and HCl in dioxane (4M, 2.26 mL) was added dropwise with stirring. The precipitate was filtered off and dried to yield the sub-title compound (2.5 g, 95%).

(b) 5-(4-tert-Butylphenyl)-1-(4-(2-methyl-1-(4-methylpiperazin-1-yl)-1-oxopropan-2-yloxy)phenyl)indole-2-carboxylic acid hydrochloride The title compound was prepared in accordance with Example 1 using 5-(4-tert-butylphenyl)indole-2-carboxylic acid ethyl ester and 1-(2-(4-bromophenoxy)-2-methylpropanoyl)-4-methylpiperazine hydrochloride (see (a)), followed by precipitation of the hydrochloride salt using HCl (4 M in dioxane).

200 MHz $^1$H-NMR (DMSO-$d_6$, ppm) δ 12.76 (1H, s), 11.06 (1H, s), 7.97 (1H, d, J=1.1 Hz), 7.60-7.53 (3H, m), 7.48-7.41 (3H, m), 7.36-7.30 (2H, m), 7.08 (1H, d, J=8.8 Hz), 6.98-6.91 (2H, m), 4.80-4.46 (2H, m), 3.62-2.97 (4H, m, overlapped with water peak), 2.82-2.57 (1H, m), 2.68 (3H, s), 2.41-2.13 (1H, m), 1.64 (6H, s), 1.30 (9H, s).

Example 31

5-(4-tert-Butylphenyl)-1-(4-(1-hydroxy-2-methylpropan-2-yloxy)phenyl)-indole-2-carboxylic acid (a) 2-(4-Bromophenoxy)-2-methylpropan-1-ol The sub-title compound was prepared by reduction of 2-(4-bromophenoxy)-2-methylpropanoic acid (2 g, 7.7 mmol) with $BH_3 \times THF$ (1M, 27.0 mmol, 27.0 mL) in accordance with the procedure described in Example 29(b). Distillation under reduced pressure gave the sub-title compound (1.60 g, 85%).

(b) 5-(4-tert-Butylphenyl)-1-(4-(1-hydroxy-2-methylpropan-2-yloxy)phenyl)indole-2-carboxylic acid The title compound was prepared in accordance with Example 1 using 5-(4-tert-butylphenyl)indole-2-carboxylic acid ethyl ester and 2-(4-bromophenoxy)-2-methylpropan-1-ol.

200 MHz $^1$H-NMR (DMSO-$d_6$, ppm) δ 12.80 (1H, s), 7.99 (1H, d, J=1.1 Hz), 7.62-7.55 (3H, m), 7.50-7.42 (3H, m), 7.32-7.25 (2H, m), 7.19-7.12 (2H, m), 7.08 (1H, d, J=8.8 Hz), 4.98 (1H, t, J=5.7 Hz), 3.45 (2H, d, J=5.7 Hz), 1.32 (9H, s), 1.28 (6H, s).

Example 32

5-(4-Cyclohexylphenyl)-1-(4-isopropoxyphenyl) indole-2-carboxylic acid (a) 5-Bromo-1-(4-isopropoxyphenyl)indole-2-carboxylic acid ethyl ester The sub-title compound was prepared in accordance with Example 8(c) from 5-bromoindole-2-carboxylic acid ethyl ester and 4-isopropoxyphenylboronic acid.

(b) 5-(4-Cyclohexylphenyl)-1-(4-isopropoxyphenyl) indole-2-carboxylic acid ethyl ester A mixture of 5-bromo-1-(4-isopropoxyphenyl)indole-2-carboxylic acid ethyl ester (154 mg, 0.38 mmol), K$_3$PO$_4$ (282 mg, 1.83 mmol), Pd(OAc)$_2$ (4.5 mg, 0.02 mmol), tri(o-tolyl) phosphine (12 mg, 0.04 mmol), and toluene (3.5 mL) was stirred under argon for 25 min at room temperature. 4-Cyclohexylphenylboronic acid (117 mg, 0.57 mmol) in EtOH (0.5 mL) was added and the mixture was heated at reflux for 1 h. The mixture was allowed to cool, poured into NaHCO$_3$ (aq. sat.), and extracted wait EtOAc. The combined extracts were washed with brine, dried over Na$_2$SO$_4$, concentrated and purified by chromatography to give the sub-title compound (170 mg, 93%).

(c) 5-(4-Cyclohexylphenyl)-1-(4-isopropoxyphenyl) indole-2-carboxylic acid

The title compound was prepared by hydrolysis of 5-(4-cyclohexylphenyl)-1-(4-isopropoxyphenyl)indole-2-carboxylic acid ethyl ester in accordance with the procedure described in Example 1(c).

200 MHz $^1$H-NMR (DMSO-$d_6$, ppm) δ 12.8 (1H, br s), 7.97 (1H, d, J=1.2 Hz), 7.61-7.49 (3H, m), 7.41 (1H, s), 7.33-7.22 (4H, m), 7.10-6.99 (3H, m), 4.69 (1H, septet, J=6.0 Hz), 2.66-2.43 (1H, m, overlapped with DMSO signal), 1.89-1.65 (5H, m), 1.53-1.25 (5H, m) 1.33 (6H, d, J=6.0 Hz).

Example 33

3-Chloro-5-(4-isopropoxyphenyl)-1-(6-isopropoxypyrid-3-yl )indole-2-carboxylic acid (a) 3-Chloro-5-(4-isopropoxyphenyl)-1-(6-isopropoxypyrid-3-yl)indole-2-carboxylic acid ethyl ester N-Chlorosuccinimide (37 mg, 280 nmol) and 5-(4-isopropoxyphenyl)-1-(6-isopropoxypyrid-3-yl)indole-2-carboxylic acid ethyl ester (117 mg, 255 nmol; see Example 17) were mixed in CCl$_4$ (2 mL) and stirred at 80° C. for 2 h. The mixture was diluted with EtOAc and washed with Na$_2$S$_2$O$_3$ (aq., 10%) and NaHCO$_3$ (aq., sat.). The combined extracts were washed with water, brine and dried over Na$_2$SO$_4$. Concentration gave the sub-title compound (116 mg, 92%).

(b) 3-Chloro-5-(4-isopropoxyphenyl)-1-(6-isopropoxypyrid-3-yl)indole-2-carboxylic acid The title compound was prepared in accordance with Example 1(c).

200 MHz $^1$H-NMR (DMSO-$d_6$, ppm) δ 13.5-13.3 (1H, br s), 8.20 (1H, d, J=2.7 Hz), 7.79 (1H, s), 7.77 (1H, dd, J=6.0, 2.7 Hz), 7.64-7.56 (3H, m), 7.11 (1H, d, J=8.8 Hz), 7.04-6.94 (2H, m), 6.88 (1H, d, J=8.8 Hz), 5.23 (1H, septet, J=6.2 Hz), 4.64 (1H, septet, J=6.0 Hz), 1.27 (6H, d, J=6.2 Hz), 1.25 (6H, d, J=6.0 Hz).

Example 34

3-Bromo-1,5-bis(4-isopropoxyphenyl)indole-2-carboxylic acid (a) 3-Bromo-1,5-bis(4-isopropoxyphenyl)indole-2-carboxylic acid ethyl ester N-Bromosuccinimide (467 mg, 2.62 mmol) was added in portions to 1,5-bis(4-isopropoxyphenyl)indole-2-carboxylic acid ethyl ester (1.0 g, 2.19 mmol; see Example 3) in CCl$_4$ (50 mL) at room temperature. The mixture was stirred at 60° C. for 2.5 h after which additional N-bromosuccinimide (100 mg, 560 mol) was added and the mixture was heated for another 1 h. The mixture was allowed to cool, poured into Na$_2$S$_2$O$_3$ (aq., 10%) and extracted with EtOAc. The combined extracts were washed with Na$_2$S$_2$O$_3$ (aq., 10%), NaHCO$_3$ (aq., sat.) and brine and then dried over Na$_2$S$_2$O$_4$. Concentration and purification by chromatography gave the sub-title compound (968 mg, 82%).

(b) 3-Bromo-1,5-bis(4-isopropoxyphenyl)indole-2-carboxylic acid

The title compound was prepared in accordance with Example 1(c).

200 MHz $^1$H-NMR (DMSO-$d_6$, ppm) δ 13.5-13.2 (1H, br s), 7.72 (1H, d, J=1.2 Hz), 7.64-7.57 (3H, m), 7.35-7.26 (2H, m), 7.10 (1H, d, J=8.8 Hz), 7.08-6.98 (4H, m), 4.69 (1H, septet, J=6.0 Hz), 4.66 (1H, septet, J=6.0 Hz), 1.33 (6H, d, J=6.0 Hz), 1.29 (6H, d, J=6.0 Hz).

Example 35

3-Chloro-1-(4-isopropoxphenyl)-5-(5-trifluoromethylpyrid-2-yl)-1H-indole-2-carboxylic acid Method 1

(a) 5-Bromo-3-chloro-1H-indole-2-carboxylic acid ethyl ester

A mixture of 5-bromoindole-2-carboxylic acid ethyl ester (4.00 g, 14.9 mmol), sulfurylchloride (1.8 mL, 22.4 mmol) and benzene (125 mL) was stirred at 90° C. for 2.5 h. The mixture was cooled to room temperature, NaHCO$_3$ (aq., sat.) was added and the mixture extracted with EtOAc. The combined extracts were washed with water, brine and dried over Na$_2$SO$_4$. Concentration and recrystallisation (from toluene) gave the sub-title compound (3.87 g 85%).

(b) 5-Bromo-3-chloro-1-(4-isopropoxyphenyl)-1H-indole-2-carboxylic acid ethyl ester The sub-title compound was prepared in accordance with Example 8(c), using 5-bromo-3-chloro-1H-indole-2-carboxylic acid ethyl ester (see step (a) above) and 4-isopropoxyphenylboronic acid.

(c) 3-Chloro-1-(4-isopropoxyphenyl)-5-(4,4,5,5-tetramethyl[1,3,2]dioxaborolan-2-yl)-1H-indole-2-carboxylic acid ethyl ester The sub-title compound was prepared in accordance with Example 8(a), using 5-bromo-3-chloro-1-(4-isopropoxyphenyl)-1H-indole-2-carboxylic acid ethyl ester (see step (b)) and bis(pinacolato)diboron.

(d) 3-Chloro-1-(4-isopropoxyphenyl)-5-(5-trifluoromethylpyrid-2-yl)-1H-indole-2-carboxylic acid ethyl ester The sub-title compound was prepared in accordance with Example 8(b), from 3-chloro-1-(4-isopropoxyphenyl)-5-(4,4,5,5-tetramethyl[1,3,2]dioxaborolan-2-yl)-1H-indole-2-carboxylic acid ethyl ester (see step (c)) and 2-bromo-5-(trifluoromethyl)pyridine.

(e) 3-Chloro-1-(4-isopropoxyphenyl)-5-(5-trifluoromethylpyrid-2-yl)-1H-indole-2-carboxylic acid The title compound was prepared by hydrolysis of 3-chloro-1-(4-isopropoxyphenyl)-5-(5-trifluoromethylpyrid-2-yl)-1H-indole-2-carboxylic acid ethyl ester in accordance with the procedure described in Example 1(c).

200 MHz $^1$H-NMR (DMSO-$d_6$, ppm) δ 9.06-9.00 (1H, m) 8.48-8.42 (1H, m) 8.32-8.21 (2H, m) 8.17-8.05 (1H, m) 7.37-7.27 (2H, m) 7.19 (1H, d, J=8.8 Hz) 7.10-6.98 (2H, m) 4.67 (1H, septet, J=5.9 Hz) 1.31 (6H, d, J=5.9 Hz).

Method 2

(a) 3-Chloro-5-iodo-1-(4-isopropoxyphenyl)-1H-indole-2-carboxylic acid ethyl ester A mixture of 5-bromo-3-chloro-1-(4-isopropoxyphenyl)-1H-indole-2-carboxylic acid ethyl ester (2.80 g, 6.44 mmol) (prepared in accordance with the procedure described in Example 35, Method 1, step (b)), CuI (122 mg, 0.64 mmol), NaI (1.94 g, 12.9 mmol), N,N'-dimethyl-1,2-diaminoethane (142 µL, 1.28 mmol) and 1,4-dioxane (10 ml) was stirred at 120° C. for 24 h. The mixture was cooled to room temperature and diluted with EtOAc (200 ml). The combined organic phase was washed with diluted NH$_4$OH solution (2×200 mL), HCl (0.1 N solution; 2×200 mL), brine (100 mL) and dried over Na$_2$SO$_4$. Filtration and concentration of the organic phase gave the sub-title compound (3.02 g 97%).

(b) 3-Chloro-5-(dihydroxyboryl)-1-(4-isopropoxyphenyl)-1H-indole-2-carboxylic acid ethyl ester To solution of 3-chloro-5-iodo-1-(4-isopropoxyphenyl)-1H-indole-2-carboxylic acid ethyl ester (1.45 g, 3.0 mmol, see step (a) above) in THF (9 mL) was added i-PrMgCl×LiCl (0.95 M solution in THF; 3.26 mL, 3.1 mmol) at −40° C. over 5 min. After stirring for 15 min at −40° C., B(OEt)$_3$ (1.56 mL, 9.0 mmol) was added. The temperature of the reaction mixture was allowed to reach 0° C. over 2 h, then HCl (2.5 M solution in water; 3.6 mL, 36 mmol) was added and stirring continued for a further 1 h at 0° C. The reaction mixture was diluted with brine (70 mL) and extracted with t-BuOMe (4×70 mL). The combined organic extracts were washed with brine (100 mL), dried over Na$_2$SO$_4$ and concentrated. The solid thereby obtained was washed several times with light petrol and filtered affording pure sub-title compound (1.04 g, 86%)

(c) 3-Chloro-1-(4-isopropoxyphenyl)-5-(5-trifluoromethylpyrid-2-yl)-1H-indole-2-carboxylic acid ethyl ester A stirred mixture of 3-chloro-5-(dihydroxyboryl)-1-(4-isopropoxyphenyl)-1H-indole-2-carboxylic acid ethyl ester (200 mg, 0.50 mmol; see step (b) above), 2-bromo-5-(trifluoromethyl)pyridine (170 mg, 0.75 mmol), sodium carbonate (2M in water, 0.75 mL, 1.5 mmol), Pd(PPh$_3$)$_4$ (29 mg, 0.025 mmol), EtOH (0.4 mL) and toluene (1.6 mL) was heated at 85° C. for 3 h. The reaction was diluted with EtOAc, washed with brine, dried over MgSO$_4$, concentrated and purified by chromatography to give the sub-title compound (239 mg, 95%).

(d) 3-Chloro-1-(4-isopropoxyphenyl)-5-(5-trifluoromethylpyrid-2-yl)-1H-indole-2-carboxylic acid The title compound was prepared by hydrolysis of 3-chloro-1-(4-isopropoxyphenyl)-5-(5-trifluoromethylpyrid-2-yl)-1H-indole-2-carboxylic acid ethyl ester in accordance with the procedure described in Example 1(c).

Method 3

(a) 3-Chloro-1-(4-isopropoxyphenyl)-5-(5-trifluoromethylpyrid-2-yl)-1H-indole-2-carboxylic acid ethyl ester t-BuLi (3.25 mL of 1.5M solution in pentane) was added dropwise at −78° C. to Et$_2$O (5 mL). To the resulting solution was added, via syringe, a solution of 2-bromo-5-(trifluoromethyl)pyridine (550 mg, 2.43 mmol) in Et$_2$O (2.5 mL). Stirring at −78° C. was continued for 20 min after which the cold reaction mixture was transferred via cannula to a cooled (−78° C.) 1M solution of ZnCl$_2$ in Et$_2$O (5.25 mL, 5.35 mmol). The reaction was allowed to warm to room temperature and left to stir for 3 h. THF (10 mL) was then added and the resulting solution was transferred via cannula to a mixture of 5-bromo-3-chloro-1-(4-isopropoxyphenyl)-1H-indole-2-carboxylic acid ethyl ester (see Example 35, Method 1, step (b)) (531 mg, 1.22 mmol), Pd(dppf)Cl$_2$ (118.4 mg, 0.145 mmol), CuI (56.2 mg, 0.295 mmol) and N-methylpyrrolidine-2-one (2.5 mL) under argon. The reaction was heated at 80° C. for 6 h, poured into NH$_4$Cl (aq. sat., 50 mL) and extracted with t-BuOMe (3×25 mL). The combined organic extracts were washed with brine, dried (Na$_2$SO$_4$), then filtered through a Celite® pad and the filter cake was washed with t-BuOMe. The solvent was removed and the residue dissolved in dry Et$_2$O and HCl (4M in dioxane; 360 µL, 1.4 mmol) was added. After stirring for 10 min, solvents were removed by evaporation and the residue was twice recrystalised from EtOH to yield the sub-title compound (462 mg, 75%).

(b) 3-Chloro-1-(4-isopropoxyphenyl)-5-(5-trifluoromethylpyrid-2-yl)-1H-indole-2-carboxylic acid To a solution of 3-chloro-1-(4-isopropoxyphenyl)-5-(5-trifluoromethylpyrid-2-yl)-1H-indole-2-carboxylic acid ethyl ester (see step (a) above; 500 mg, 1.0 mmol) in dioxane (5 mL) was added NaOH (aq. 2N, 2.5 mL) and the reaction was refluxed for 4 h. After cooling to room temperature, the reaction was diluted with water and acidified by the addition of HCl (aq. 1N) to about pH 6. The precipitate was filtered, washed with water and dried. Recrystallisation (from EtOAc/petroleum ether) afforded the title compound (289 mg, 62%).

Example 36

3-Chloro-1-(6-cyclopentoxypyrid-3-yl)-5-(5-trifluoromethylpyrid-2-yl)-1H-indole-2-carboxylic acid

(a) 3-Chloro-5-(5-trifluoromethylpyrid-2-yl)-1H-indole-2-carboxylic acid ethyl ester N-Chlorosuccimimide (480 mg, 3.86 mmol) and 5-(5-trifluoromethylpyrid-2-yl)-1H-indole-2-carboxylic acid ethyl ester (800 mg, 2.4 mmol; see Example 8 (b)) were mixed in $CCl_4$ (50 mL) and stirred at 80° C. for 2 h. The mixture was diluted with EtOAc and washed with $Na_2S_2O_3$ (aq., sat.), $NaHCO_3$ (aq., sat.), brine and dried over $Na_2SO_4$ Concentration gave the sub-title compound (870 mg, 98%).

(b) 5-Bromo-2-cyclopentoxypyridine

A mixture of 5-bromo-1H-pyridin-2-one (4.0 g, 23 mmol), $Ag_2CO_3$ (3.77 g, 1.37 mmol), cyclopentyl bromide (7.4 mL, 29 mmol) and toluene (30 ml) was stirred at 60° C. for 2 days. The reaction was filtered through Celite® and the filter cake was washed with EtOAc. Concentration and vacuum distillation gave the sub-title compound (5.09 g, 92%).

(c) 6-Cyclopentoxypyridine-3-boronic acid

To a mixture of 5-bromo-2-cyclopentoxypyridine (2.5 g, 10.3 mmol, see step (b) above), $B(O-iPr)_3$ (2.33 g, 13.4 mmol), THF (4.1 mL) and toluene (16.5 mL) was portionwise-added BuLi (2.5 M in hexane; 4.96 ml, 13.4 mmol) at −70° C. over 1 h. The reaction mixture was stirred over a further 40 min at −70° C. and then allowed to warm to −20° C. The acidity of the reaction mixture was adjusted to about pH 1 by addition of HCl (2 M aq. solution). The reaction was diluted with water (50 mL) and extracted with $Et_2O$ (2×50 mL). The pH of the water phase was then adjusted to about pH 7 by the addition of NaOH (5 M aq. solution). Brine was added and the product was extracted with EtOAc (4×50 mL). Removal of the solvent afforded the sub-title compound (0.99 g, 46%).

(d) 3-Chloro-1-(6-cyclopentoxypyrid-3-yl)-5-(5-trifluoromethylpyrid-2-yl)-1H-indole-2-carboxylic acid ethyl ester The sub-title compound was prepared in accordance with Example 8(c), using 3-chloro-5-(5-trifluoromethylpyrid-2-yl)-1H-indole-2-carboxylic acid ethyl ester (see step (a) above) and 6-cyclopentoxypyridine-3-boronic acid (see step (c) above).

(e) 3-Chloro-1-(6-cyclopentoxypyrid-3-yl)-5-(5-trifluoromethylpyrid-2-yl-1H-indole-2-carboxylic acid The title compound was prepared by hydrolysis of 3-chloro-1-(6-cyclopentoxypyrid-3-yl)-5-(5-trifluoromethylpyrid-2-yl)-1H-indole-2-carboxylic acid ethyl ester (see step (d) above) in accordance with the procedure described in Example 1(c).

200 MHz $^1$H-NMR (DMSO-$d_6$, ppm) δ 9.05 (1H, s) 8.54 (1H, s) 8.36-8.17 (4H, m) 7.82 (1H, dd, J=8.8, 2.7 Hz) 7.22 (1H, d, J=9.0 Hz) 6.92 (1H, d, J=8.8 Hz) 5.85-5.38 (1H, m) 2.08-1.51 (8H, m).

Example 37

1-(6-Cyclopentoxypyrid-3-yl)-5-(5-trifluoromethylpyrid-2-yl)-1-H-indole-2-carboxylic acid The title compound was prepared in accordance with Example 36(d) from 5-(5-trifluoromethylpyrid-2-yl)-1H-indole-2-carboxylic acid ethyl ester (see Example 8(b)) and 6-cyclopentoxypyridine-3-boronic acid (see Example 36(c)), followed by ester hydrolysis (see Example 36(e)).

200 MHz $^1$H-NMR (DMSO-$d_6$, ppm) δ 9.00 (1H, s) 8.63-8.58 (1H, m) 8.28-8.18 (3H, m) 8.12 (1H, dd, J=8.8, 1.7 Hz) 7.76 (1H, dd, J=8.8, 2.7 Hz) 7.50 (1H, s) 7.17 (1H, d, J=8.9 Hz) 6.89 (1H, d, J=8.8 Hz) 5.31 (1H, septet, J=6.2 Hz) 1.35 (6H., d, J=6.2 Hz).

Example 38

1-(6-Isopropoxypyrid-3-yl)-5-(5-trifluoromethylpyrid-2-yl)-1H-indole-2-carboxylic acid

(a) 5-Bromo-2-isopropoxypyridine

The sub-title compound was prepared in accordance with Example 36(b) from isopropylbromide and 5-bromo-1H-pyridin-2-one.

(b) 6-Isopropoxpyridine-3-boronic acid

The sub-title compound was prepared in accordance with Example 36(c) from 5-bromo-2-isopropoxypyridine.

(c) 1-(6-Isopropoxypyrid-3-yl)-5-(5-trifluoromethylpyrid-2-yl)-1H-indole-2-carboxylic acid ethyl ester The sub-title compound was prepared in accordance with Example 8(c) from 5-(5-trifluoromethylpyrid-2-yl)-1H-indole-2-carboxylic acid ethyl ester (see Example 8(b)) and 6-isopropoxypyridine-3-boronic acid (see step (b) above).

(d) 1-(6-Isopropoxypyrid-3-yl)-5-(5-trifluoromethylpyrid-2-yl)-1H-indole-2-carboxylic acid The title compound was prepared by hydrolysis of 1-(6-isopropoxypyrid-3-yl)-5-(5-trifluoromethylpyrid-2-yl)-1H-indole-2-carboxylic acid ethyl ester (see step (c) above) in accordance with the procedure described in Example 1(c).

200 MHz $^1$H-NMR (DMSO-$d_6$, ppm) δ 9.05 (1H, s) 8.54 (1H, s) 8.36-8.17 (4H, m) 7.82 (1H, dd, J=8.8, 2.7 Hz) 7.22 (1H, d, J=9.0 Hz) 6.92 (1H, d, J=8.8 Hz) 5.85-5.38 (1H, m) 2.08-1.51 (8H, m).

Example 39

5-(4-tert-Butylphenyl)-1-(4-cyclopropoxyphenyl)-1H-indole-2-carboxylic acid

(a) 1-Bromo-4-(2-bromoethoxy)benzene

A mixture of 4-bromophenol (30 g, 173 mmol), dibromoethane (40 mL, 464 mmol), NaOH (11.0 g, 275 mmol) and water (430 mL) was refluxed for 11 h. The phases were separated and the organic phase was further purified by distillation, yielding the sub-title compound (40.1 g 83%).

(b) 1-Bromo-4-vinyloxybenzene

To a solution of 1-bromo-4-(2-bromoethoxy)benzene (19.9 g, 100 mmol; see step (a) above) in THF (120 mL) was portion-wise added t-BuOK (14.0 g, 125 mmol) over 10 min at 0° C. After stirring at room temperature for 16 h, the mixture was diluted with water (400 mL) and the product was extracted with light petrol (4×100 mL). The combined organic extracts were washed with brine, dried ($Na_2SO_4$), concentrated and distilled under vacuum to yield the sub-title compound (11.5 g, 58%).

(c) 1-Bromo-4-cyclopropoxybenzene

To mixture of 1-bromo-4-vinyloxybenzene (11.5 g, 58 mmol), chloroiodomethane (41 g, 232 mmol) and dichloroethane (180 mL) was added diethylzinc (15% solution in hexanes-95.5 mL, 116 mmol) over 3 h at 0° C. After 30 min stirring, $NH_4Cl$ solution (200 mL, aq. sat.) and light petrol (300 mL) was added. The organic phase was separated and concentrated in vacuo (8 bar, 50° C.). The residue was redissolved in light petrol and the insoluble material was filtered off. The filtrate was concentrated to afford sub-title compound (11.7 g, 94%).

(d) 5-(4-tert-Butylphenyl)-1-(4-cyclopropoxyphenyl)-1H-indole-2-carboxylic acid ethyl ester The sub-title compound was prepared in accordance with Example 1(b) from 5-(4-tert-butylphenyl)indole-2-carboxylic acid ethyl ester (see Example 1(a)) and 1-bromo-4-cyclopropoxybenzene (see step (c) above).

(e) 5-(4-tert-Butylphenyl) 1-(4-cyclopropoxyphenyl)-1H-indole-2-carboxylic acid

The sub-title compound was prepared by hydrolysis of 5-(4-tert-butyl-phenyl)-1-(4-cyclopropoxyphenyl)-1H-indole-2-carboxylic acid ethyl ester (see step (c) above) in accordance with the procedure described in Example 1(c).
200 MHz $^1$H-NMR (DMSO-$d_6$, ppm) δ 7.96 (1H, d, J=1.7) 7.63-7.50 (3H, m) 7.49-7.37 (31H, m) 7.34-7.25 (2H, m) 7.22-7.12 (2H, m) 7.05 (1H, d, J=8.8 Hz) 3.97-3.85 (1H, m) 1.30 (9H, s) 0.89-0.66 (4H, m).

Example 40

1-(4-Cyclopropoxyphenyl)-5-(5-trifluoromethylpyrid-2-yl)-1H-indole-2-carboxylic acid (a) 4-Cyclopropoxyphenylboronic acid To a solution of 4-bromo-4-cyclopropoxybenzene (5.0 g, 23.4 mmol, see Example 39(c)) in THF (80 mL) at −78° C. was added n-BuLi (2.5 M solution in hexane; 9.76 mL, 24.4 mmol) over 17 min. After 40 min, B(OEt)$_3$ (5.9 mL, 34.3 mmol) was added and the reaction was warmed to room temperature and stirred at ambient temperature for 18 h. After re-cooling to 0° C., HCl (1M solution; 70 mL, aq.) was added. After 30 min the mixture was extracted with t-BuOMe (3×50 mL), the combined organic extracts were washed with brine, dried ($Na_2SO_4$) and concentrated. The residue was washed with light petrol and filtered yielding the sub-title compound (1.5 g, 34%).

(b) 1-(4-Cyclopropoxyhenyl)-5-(5-trifluoromethylpyrid-2-yl-1H-indole-2-carboxylic acid ethyl ester The sub-title compound was prepared in accordance with Example 8(c) from 5-(5-trifluoromethylpyrid-2-yl)-1H-indole-2-carboxylic acid ethyl ester (see Example 8(b)) and 4-cyclopropoxyphenylboronic acid (see step (a) above).

(c) 1-(4-Cyclopropoxyphenyl)-5-(5-trifluoromethylpyrid-2-yl)-1H-indole-2-carboxylic acid The title compound was prepared by hydrolysis of 1-(4-cyclopropoxyphenyl)-5-(5-trifluoromethylpyrid-2-yl)-1H-indole-2-carboxylic acid ethyl ester (see step (b) above) in accordance with the procedure described in Example 1(c).
200 MHz $^1$H-NMR (DMSO-$d_6$, ppm) δ 9.03 (1H, s) 8.47 (1H, s) 8.33-8.19 (2H, m) 8.13 (1H, dd, J=8.8, 1.5 Hz) 7.42-7.30 (2H, m) 7.23-7.11 (3H, m) 3.97-3.85 (1H, m) 0.90-0.65 (4H, m).

Example 41

3-Chloro-1-(4-cyclopropoxyphenyl)-5-(5-trifluoromethylpyrid-2-yl)-1H-indole-2-carboxylic acid The title compound was prepared in accordance with Example 8(c) from 3-chloro-5-(5-trifluoromethylpyrid-2-yl)-1H-indole-2-carboxylic acid ethyl ester (see Example 36(a)) and 4-cyclopropoxyphenylboronic acid (see Example 40(a)), followed by ester hydrolysis in accordance with Example 1(c).
200 MHz $^1$H-NMR (DMSO-$d_6$, ppm) δ 9.03 (1H, s) 8.47 (1H, s) 8.33-8.19 (2H, m) 8.13 (1H, dd, J=8.8, 1.5 Hz) 7.42-7.30 (2H, m) 7.23-7.11 (3H, m) 3.97-3.85 (1H, m) 0.90-0.65 (4H, m).

Example 42

5-(4-Carbamoylphenyl)-1-(4-cyclopropoxphenyl)-1H-indole-2)-carboxylic acid (a) 5-(4-Cyanophenyl)-1H-indole-2-carboxylic acid ethyl ester The sub-title compound was prepared in accordance with Example 8(b) from 5-(4,4,5,5-tetramethyl-1,3,2-dioxaborolan-2-yl)indole-2-carboxylic acid ethyl ester (see Example 8(a)) and 4-iodobenzonitrile.

(b) 5-(4-Cyanophenyl)-1-(4-cyclopropoxyphenyl)-1H-indole-2-carboxylic acid ethyl ester The sub-title compound was prepared in accordance with Example 8(c) from 5-(5-trifluoromethylpyrid-2-yl)-1H-indole-2-carboxylic acid ethyl ester (see step (a) above) and 4-cyclopropoxyphenylboronic acid (see Example 40(a)).

(c) -5-(4-Carbamoylphenyl)-1-(4-cyclopropoxyphenyl)-1H-indole-2-carboxylic acid

The title compound was prepared by hydrolysis of 5-(4-cyanophenyl)-1-(4-cyclopropoxyphenyl)-1H-indole-2-carboxylic acid ethyl ester (see step (b) above) in accordance with the procedure described in Example 1(c).
200 MHz $^1$H-NMR (DMSO-$d_6$, ppm) δ 12.8 (1H, br s) 8.09 (1H, d, J=1.6) 8.03-7.90 (3H, m) 7.79-7.70 (2H, m) 7.63 (1H, dd, J=8.9, 1.6 Hz) 7.42 (1H, s) 7.38-7.27 (3H, m) 7.23-7.14 (2H, m) 7.08 (1H, d, J=8.9 Hz) 3.97-3.85 (1H, m) 0.89-0.66 (4H, m).

Example 43

3-Chloro-5-(6-cyclopentoxypyrid-3-yl)-1-(4-isopropoxyphenyl)-1H-indole-2-carboxylic acid The title compound was prepared in accordance with Example 8(b) from 3-chloro-1-(4-isopropoxyphenyl)-5-(4,4,5,5-tetramethyl[1,3,2]dioxaborolan-2-yl)-1H-indole-2-carboxylic acid ethyl ester (see Example 35(c)) and 5-bromo-2-cyclopentoxypyridine (see Example 36(b)), followed by ester hydrolysis in accordance with Example 1(c).

200 MHz $^1$H-NMR (DMSO-$d_6$, ppm) δ 8.48 (1H, d, J=2.5 Hz) 8.02 (1H, dd, J=8.8, 2.5 Hz) 7.84 (1H, d, J=1.5 Hz) 7.61 (1H, dd, J=8.8, 1.5 Hz) 7.35-7.24 (2H, m) 7.12 (1H, d, J=8.8 Hz) 7.08-6.98 (2H, m) 6.84 (1H, d, J=8.8 Hz) 5.46-5.33 (1H, m) 4.68 (1H, septet, J=5.9 Hz) 2.06-1.50 (8H, m) 1.32 (6H, d, J=5.9 Hz).

Example 44

3-Chloro-1-(4-isopropoxyphenyl)-5-(5-propylpyrimidin-2-yl)-1H-indole-2-carboxylic acid The title compound was prepared in accordance with Example 35, Method 1, step (d) from 3-chloro-1-(4-isopropoxyphenyl)-5-(4,4,5,5-tetramethyl-[1,3,2]dioxaborolan-2-yl)-1H-indole-2-carboxylic acid ethyl ester (see Example 35, Method 1, step (c)) and 2-chloro-5-propylpyrimidine, followed by ester hydrolysis in accordance with Example 1(c).

200 MHz $^1$H-NMR (DMSO-$d_6$, ppm) δ 8.79-8.67 (3H, m) 8.37 (1H, dd, J=8.8, 1.5 Hz) 7.38-7.26 (2H, m) 7.17 (1H, d, J=8.8 Hz) 7.09-6.98 (2H, m) 4.68 (1H, septet, J=5.9 Hz) 2.60 (2H, t, J=7.7 Hz) 1.64 (2H, m) 1.32 (6H, d, J=5.9 Hz) 0.93 (3H, t, J=7.7 Hz).

Example 45

3-Chloro-5-(4-cyclohexylphenyl)-1-(5-cyclopentylaminopyrid-2-yl)-1H-indole-2-carboxylic acid sodium salt (a) 3-Chloro-5-(4-cyclohexylphenyl)-1H-indole-2-carboxylic acid The sub-title compound was prepared in accordance with Example 1(a) from 5-bromo-3-chloroindole-2-carboxylic acid ethyl ester (see Example 35, Method 1, step (a)) and 4-cyclohexylphenylboronic acid.

(b) (6-Bromopyrid-3-yl)cyclopentylamine

To a solution of 6-bromopyrid-3-ylamine (2.0 g, 11.6 mmol) in $CH_2Cl_2$ (30 mL) was added cyclopentanone (1.3 mL) 15.5 mmol), followed by $TiCl_4$ (1.4 mL, 12.7 mmol) in $CH_2Cl_2$ (20 mL) and after stirring for 3.5 h at room temperature, $NaBH_3CN$ (2.17 g, 34.5 mmol) was added portion-wise. The reaction was left to stir overnight at ambient temperature, diluted with t-BuOMe (200 mL), washed with water, brine and dried ($Na_2SO_4$). Solvent removal and purification by chromatography afforded the sub-title compound (880 mg, 40%).

(c) 3-Chloro-5-(4-cyclohexylphenyl)-1-(5-cyclopentylaminopyrid-2-yl-1H-indole-2-carboxylic acid ethyl ester The title compound was prepared in accordance with Example 1(b) from 3-chloro-5-(4-cyclohexylphenyl)-1H-indole-2-carboxylic acid (see step (a) above) and (6-bromopyrid-3-yl)cyclopentylamine (see step (b) above).

(d) 3-Chloro-5-(4-cyclohexylphenyl)-1-(5-cyclopentylaminopyrid-2-yl)-1H-indole-2-carboxylic acid sodium salt A mixture of 3-chloro-5-(4-cyclohexylphenyl)-1-(5-cyclopentylamino-pyrid-2-yl)-1H-indole-2-carboxylic acid ethyl ester (see step (c) above) (120 mg, 0.22 mmol), NaOH (2M aq., 1.0 mL, 2.0 mmol) and dioxane (2.0 mL) was heated in a sealed vessel at 140° C. for 2 h. After dilution with water (5 mL) the precipitate formed was filtered, washed with water and dried ($P_2O_5$) to yield the title compound (105 mg, 85%).

200 MHz $^1$H-NMR (DMSO-$d_6$, ppm) δ 7.83 (1H, d, J=1.6 Hz) 7.63-7.56 (3H, m) 7.41 (2H, m) 7.31-7.25 (2H, m) 7.12 (1H, d, J=8.8 Hz) 7.01 (1H, dd, J=8.8, 2.6 Hz) 5.98 (1H, d, J=6.4 Hz) 3.81-3.67 (1H, m) 2.59-2.51 (1H, m) 2.00-1.13 (18H, m).

Example 46

3-Chloro-5-(4-cyclohexylphenyl)-1-(5-trifluoromethylpyrid-2-yl)-1H-indole-2-carboxylic acid sodium salt The title compound was prepared in accordance with Example 45 from 3-chloro-5-(4-cyclohexylphenyl)-1H-indole-2-carboxylic acid (Example 45(a) and 2-bromo-5-(trifluoromethyl)pyridine, followed by ester hydrolysis in accordance with Example 45(d).

200 MHz $^1$H-NMR (DMSO-$d_6$, ppm) δ 8.97 (1H, s) 8.30 (1H, dd, J=8.6, 2.1 Hz) 7.88 (1H, d, J=8.6 Hz) 7.72-7.71 (1H, m) 7.65-7.52 (4H, m) 7.34-7.28 (2H, m) 2.61-2.46 (1H, m, overlapped with DMSO) 1.83-1.63 (5H, m) 1.53-1.15 (5H, m).

Example 47

3-Chloro-5-(5-cyclopentylaminopyrid-2-yl)-1-(4-isopropoxyphenyl)-1H-indole-2-carboxylic acid The title compound was prepared in accordance with Example 8(b) from 3-chloro-1-(4-isopropoxyphenyl)-5-(4,4,5,5-tetramethyl[1,3,2]dioxaborolan-2-yl)-1H-indole-2-carboxylic acid ethyl ester (see Example 35, Method 1, step (c)) and 6-bromopyrid-3-ylcyclopentylamine (see Example 45(b)), followed by ester hydrolysis according to Example 35, Method 3, step (b).

200 MHz $^1$H-NMR (DMSO-$d_6$, ppm) δ 8.28-8.20 (1H, m) 8.14-8.04 (1H, m) 7.96 (1H, d, J=1.5 Hz) 7.89-7.80 (1H, m) 7.68-7.56 (1H, m) 7.38-7.25 (2H, m) 7.19 (1H, d, J=8.7 Hz) 7.12-6.98 (2H, m) 4.69 (1H, septet, J=5.9 Hz) 3.96-3.78 (1H, m) 3.78-3.28 (3H, m) 2.08-1.84 (2H, m) 1.81-1.37 (6H, m) 1.32 (6H, d, J=5.9 Hz).

Example 48

5-(5-Bromopyrimidin-2-yl)-1-(4-cyclopentoxyphenyl)-1H-indole-2-carboxylic acid

(a) 1-Bromo-4-cyclopentoxybenzene

A mixture of 4-bromophenol (40 g, 231 mmol), cyclopentylbromide (50 ml, 462 mmol), NaOH (18.5 g, 462 mmol) and DMF (150 mL) was stirred at 100° C. for 13.5 h, poured into water (300 mL) and extracted with t-BuOMe (4×100 mL). The combined organic extracts were washed with water (2×100 mL), brine, dried ($Na_2SO_4$), concentrated and distilled in vacuo to yield the sub-title compound (46.4 g, 94%).

(b) 4-Cyclopentoxyphenylboronic acid

The sub-title compound was prepared in accordance with Example 40(a) from 1-bromo-4-cyclopentoxybenzene (see step (a) above).

(c) 5-Bromo-1-(4-cyclopentoxyphenyl)-1H-indole-2-carboxylic acid ethyl ester The sub-title compound was prepared in accordance with Example 8(c), using 5-bromo-1H-indole-2-carboxylic acid ethyl ester and 4-cyclopentoxy-phenylboronic acid (see step (b) above).

(d) 1-(4-Cyclopentoxyphenyl)-5-(4,4,5,5-tetramethyl[1,3,2]dioxaborolan-2-yl)-1H-indole-2-carboxylic acid ethyl ester The sub-title compound was prepared in accordance with Example 8(a) from 5-bromo-1-(4-cyclopentoxyphenyl)-1H-indole-2-carboxylic acid ethyl ester (see step (c) above) and bis(pinacolato)diboron.

(e) 5-Bromo-1H-pyrimidin-2-one

To a solution of 2-amino-5-bromopyrimidine (2.0 g, 11.5 mmol) in acetic acid (35 mL) was added a solution of $NaNO_2$ (4.76 g, 69 mmol) in water (25 mL) at room temperature over 1.5 h. After stirring at room temperature for 5 h the reaction mixture was partly evaporated, the precipitate formed was filtered and washed with water to yield the sub-title compound (1.4 g, 70%).

(f) 2,5-Dibromopyrimidine

A mixture of 5-bromo-1H-pyridin-2-one (see step (e) above; 1.40 g, 8.0 mmol), $POBr_3$ (2.8 g, 9.8 mmol) and $PBr_3$ (7.7 mL) was refluxed for 1.5 h. After cooling to room temperature the reaction was poured into a mixture of crushed ice and $Na_2CO_3$ (saturated aq. solution) and extracted with EtOAc (3×100 mL). The combined organic extracts were washed with brine, dried with $Na_2SO_4$ and concentrated. The residue was re-dissolved in EtOAc/light petrol (1:1) and filtered through a silica pad. Concentration of the filtrate gave the sub-title compound (0.95 g, 50%).

(g) 5-(5-Bromopyrimidin-2-yl)-1-(4-cyclopentoxyphenyl)-1H-indole-2-carboxylic acid ethyl ester The sub-title compound was prepared in accordance with Example 8(b), from 1-(4-cyclopentoxyphenyl)-5-(4,4,5,5-tetramethyl[1,3,2]dioxaborolan-2-yl)-1H-indole-2-carboxylic acid ethyl ester (see step (d) above) and 2,5-dibromopyrimidine (see step (f) above).

(h) 5-(5-Bromopyrimidin-2-yl)-1-(4-cyclopentoxyphenyl)-1H-indole-2-carboxylic acid The title compound was prepared by hydrolysis of 5-(5-bromopyrimidin-2-yl)-1-(4-cyclopentoxyphenyl)-1H-indole-2-carboxylic acid ethyl ester (see step (g) above) in accordance with the procedure described in Example 35, Method 3, step (b).

200 MHz $^1$H-NMR (DMSO-$d_6$, ppm) δ 13.1-12.7 (1H, br.s) 9.02 (2H, s) 8.80 (1H, d, J=1.5 Hz) 8.27 (1H, dd, J=8.9, 1.5 Hz) 7.48 (1H, s) 7.32-7.22 (2H, m) 7.10 (1H, d, J=8.9 Hz) 7.06-6.96 (2H, m) 4.93-4.82 (1H, m) 2.06-1.48 (8H, m).

Example 49

1-(4-Cyclopentoxyphenyl)-5-(5-pyrid-2-ylpyrimidin-2-yl)-1H-indole-2-carboxylic acid The title compound was prepared in accordance with Example 8(b) from 5-(5-bromopyrimidin-2-yl)-1-(4-cyclopentoxyphenyl)-1H-indole-2-carboxylic acid ethyl ester (see Example 48(g)) and 3-(4,4,5,5-tetramethyl-[1,3,2]dioxaborolan-2-yl)pyridine, followed by ester hydrolysis in accordance with the procedure described in Example 35, Method 3, step (b).

200 MHz $^1$H-NMR (DMSO-$d_6$, ppm) δ 13.3-12.4 (1H, br.s) 9.27 (2H; s) 9.12-9.04 (1H, m) 8.90 (1H, d, J=1.5 Hz) 8.73-8.62 (1H, m) 8.40 (1H, dd, J=8.8, 1.5 Hz) 8.34-8.24 (1H, m) 7.65-7.50 (2H, m) 7.36-7.24 (2H, m) 7.13 (1H, d, J=8.8 Hz) 7.08-6.97 (2H, m) 4.95-4.82 (1H, m) 1.92-1.47 (8H, m).

Example 50

3-Chloro-1-(4-cyclopentoxyphenyl)-5-(5-trifluoromethylpyrid-2-yl)-1H-indole-2-carboxylic acid

(a) 5-Bromo-3-chloro-1-(4-cyclopentoxyphenyl)-1H-indole-2-carboxylic acid ethyl ester The sub-title compound was prepared in accordance with the procedure described in Example 8(c) using 5-bromo-3-chloro-1H-indole-2-carboxylic acid ethyl ester (see Example 3)5, Method 1, step (a)) and 4-cyclopentoxyphenylboronic acid instead of 4-isopropoxyphenylboronic acid.

(b) 3-Chloro-1-(4-cyclopentoxyphenyl)-5-(4,4,5,5-tetramethyl[1,3,2]dioxaborolan-2-yl)-1H-indole-2-carboxylic acid ethyl ester The sub-title compound was prepared from 5-bromo-3-chloro-1-(4-cyclopentoxyphenyl)-1H-indole-2-carboxylic acid ethyl ester (see step (a) above) in accordance with the procedure described in Example 35, Method 1, step (c).

(c) 3-Chloro-1-(4-cyclopentoxyphenyl)-5-(5-trifluoromethylpyrid-2-yl)-1H-indole-2-carboxylic acid ethyl ester The sub-title compound as prepared from 3-chloro-1-(4-cyclopentoxyphenyl)-5-(4,4,5,5-tetramethyl[1,3,2]dioxaborolan-2-yl)-1H-indole-2-carboxylic acid ethyl ester (see step (b) above) in accordance with the procedure described in Example 8(a).

(d) 3-Chloro-1-(4-cyclopentoxyphenyl)-5-(5-trifluoromethylpyrid-2-yl)-1H-indole-2-carboxylic acid The title compound was prepared by hydrolysis of 3)-chloro-1-(4-cyclopentoxyphenyl)-5-(5-trifluoromethylpyrid-2-yl)-1H-indole-2-carboxylic acid ethyl ester (see step (c) above) in accordance with the procedure described in Example 35, Method 3, step (b).

200 MHz $^1$H-NMR (DMSO-$d_6$, ppm) δ 13.8-13.0 (1H, br s) 9.07-9.01 (1H, m) 8.51 (1H, s) 8.35-8.22 (2H, m) 8.18 (1H, dd, J=8.8, 1.2 Hz) 7.37-7.27 (2H, m) 7.19 (1H, d, J=8.8 Hz) 7.08-6.99 (2H, m) 4.94-4.83 (1H, m) 2.07-1.87 (2H, m) 1.86-1.54 (6H, m).

Example 51

3-Chloro-1-(4-cyclopentoxyphenyl)-5-(6-(piperidin-1-yl)pyridin-3-yl)-1H-indole-2-carboxylic acid (a) Trifluoromethanesulfolic acid 5-bromopyrid-2-yl ester To a solution of 5-bromo-1H-pyridin-2-one (4.0 g, 23.0 mmol) in CH$_2$Cl$_2$ (100 mL) was added Et$_3$N (3.9 mL, 27.6 mmol) and the resulting solution was cooled to −45° C., after which trifluoromethanesulfonic acid anhydride (5.8 mL, 34.5 mmol) was gradually added via syringe. The reaction was warmed to room temperature and left to stir overnight. The reaction was then washed twice with NaHCO$_3$ (aq. sat.), brine and dried (Na$_2$SO$_4$). Solvent removal and distillation of the residue in vacuo afforded the sub-title compound (6.51 g, 93%).

(b) 3-Bromo-6-(piperidin-1-yl)pyridine

A mixture of trifluoromethanesulfonic acid 5-bromopyrid-2-yl ester (see step (a) above; 1.5 g, 4.9 mmol), piperidine (1.07 mL, 10.8 mmol) and DMF (5 mL) was heated at 40° C. for 3 h. DMF was then removed in vacuo, water (20 mL) was added to the residue and the product extracted with EtOAc (3×15 mL) and CH$_2$Cl$_2$ (15 mL). The combined organic extracts were washed with brine and dried (Na$_2$SO$_4$). After removal of the solvent, the residue was dissolved in Et$_2$O and HCl (4M in dioxane; 4 mL) was added.

The precipitate was filtered, washed with Et$_2$O and dried to afford the sub-title compound (994 mg, 84%).

(c) 3-Chloro-1-(4-cyclopentoxyphenyl)-5-(6-(piperidin-1-yl)pyridin-3-yl)-1H-indole-2-carboxylic acid The title compound was prepared in accordance with Example 8(b), from 1-(4-cyclopentoxyphenyl)-5-(4,4,5,5-tetramethyl[1,3,2]dioxaborolan-2-yl)-1H-indole-2-carboxylic acid ethyl ester (see Example 50(b)) and 3-bromo-6-(piperidin-1-yl)pyridine (see step (b) above), followed by ester hydrolysis in accordance with the procedure described in Example 35, Method 3, step (b).

200 MHz $^1$H-NMR (DMSO-$d_6$, ppm) δ 13.5-13.1 (1H, br s) 8.44 (1H, d, J=2.4 Hz) 7.85 (1H, dd, J=9.0, 2.6 Hz) 7.79 (1H, d, J=1.1 Hz) 7.60 (1H, dd, J=8.8, 1.6 Hz) 7.32-7.24 (2H, m) 7.07 (1H, d, J=8.8 Hz) 7.05-6.98 (2H, m) 6.89 (1H, d, J=9.0 Hz) 4.92-4.82 (1H, m) 3.57-3.52 (4H, m) 2.01-1.50 (14H, m).

Example 52

3-Chloro-5-(5-chloropyrid-2-yl)-1-(4-cyclopentoxyphenyl)-1H-indole-2-carboxylic acid (a) 5-Iodo-1-(4-cyclopentoxyphenyl)-3-chloro-1H-indole-2-carboxylic acid ethyl ester The sub-title compound was prepared in accordance with Example 35, Method 2, step (a) from 5-bromo-1-(4-cyclopentoxyphenyl)-3-chloro-1H-indole-2-carboxylic acid ethyl ester (see Example 50, step (a)).

(b) 3-Chloro-5-(dihydroxyboryl)-1-(4-cyclopentoxyphenyl)-1H-indole-2-carboxylic acid ethyl ester The sub-title compound was prepared in accordance with Example 35, Method 2, step (b) from 3-chloro-1-(4-cyclopentoxyphenyl)-5-iodo-1H-indole-2-carboxylic acid (see step (a) above).

(c) Trifluoromethanesulfonic acid 5-chloropyrid-2-yl ester

The sub-title compound was prepared in accordance with Example 51(a) from 5-chloro-1H-pyridin-2-one.

(d) 3-Chloro-5-(5-chloropyrid-2-yl)-1-(4-cyclopentoxyphenyl)-1H-indole-2-carboxylic acid ethyl ester To a stirred suspension of 3-chloro-5-(dihydroxyboryl)-1-(4-cyclopentoxyphenyl)-1H-indole-2-carboxylic acid ethyl ester (see step (b) above; 214 mg, 0.5 mmol), trifluoromethanesulfonic acid 5-chloropyrid-2-yl ester (see step (c) above; 130.0 mg, 0.5 mmol) and K$_3$PO$_4$ (200 mg, 0.95 mmol) in THF (2.0 mL) under argon at room temperature was added a mixture of Pd(OAc)$_2$ (23.0 mg, 0.1 mmol) and tricyclohexylphosphine (34 mg, 0.12 mmol) in THF (2.0 mL). The reaction was stirred at ambient temperature for 12 h, diluted with Et$_2$O (10 mL), washed with brine and dried (Na$_2$SO$_4$). Concentration and purification by chromatography afforded the sub-title product (100 mg, 40%).

(e) 3-Chloro-5-(5-chloropyrid-2-yl)-1-(4-cyclopentoxyphenyl)-1H-indole-2-carboxylic acid The title compound was prepared in accordance with Example 35, Method 3, step (b) from 3-chloro-5-(5-chloropyrid-2-yl)-1-(4-cyclopentoxyphenyl)-1H-indole-2-carboxylic acid ethyl ester (see step (d) above).

200 MHz $^1$H-NMR (DMSO-$d_6$, ppm) δ 8.74-8.72 (1H, m) 8.44 (1H, s) 8.16-8.10 (2H, m) 8.02 (1H, dd, J=8.8; 2.6 Hz) 7.38-7.30 (2H, m) 7.18 (1H, d, J=9.0 Hz) 7.09-7.03 (2H, m) 4.95-4.88 (1H, m) 2.02-1.64 (8H, m).

Example 53

5-(4-Chlorophenyl)-1-(4-isopropoxyphenyl)-1H-indole-2-carboxylic acid (a) 5-(4-Chlorophenyl)-1-(4-isopropoxyphenyl)-1H-indole-2-carboxylic acid ethyl ester A mixture of 5-bromo-3-chloro-1-(4-isopropoxyphenyl)-1H-indole-2-carboxylic acid ethyl ester (see Example 35(b) 402 mg, 1.0 mmol), K$_3$PO$_4$ (716 mg, 3.37 mmol), Pd(OAc)$_2$ (22 mg, 0.1 mmol) and biphenyl-2-yldi-tert-butylphosphine (53 mg, 0.18 mmol) in toluene (10 mL) was stirred at ambient temperature for 10 min after which 4-chlorophenyl boronic acid (233 mg, 1.49 mmol) was added. The reaction was heated at reflux for 5 h, cooled to room temperature and filtered. The filter cake was washed with toluene (5 mL), the combined filtrates were concentrated and the residue was purified by chromatography to afford the sub-title compound (150 mg, 35%).

(b) 5-(4-Chlorophenyl)-1-(4-isopropoxyphenyl)-1H-indole-2-carboxylic acid

The title compound was prepared in accordance with Example 35, Method 3, step (b) from 5-(4-Chlorophenyl)-1-(4-isopropoxyphenyl)-1H-indole-2-carboxylic acid ethyl ester (see step (a) above).

200 MHz $^1$H-NMR (DMSO-$d_6$, ppm) δ 12.73 (1H, bs) 8.03-7.98 (1H, m) 7.74-7.64 (2H, m) 7.60-7.38 (4H, m) 7.31-7.21 (2H, m) 7.12-6.98 (3H, m) 4.67 (1H, septet, J=5.9 Hz) 1.32 (6H, d, J=5.9 Hz).

Example 54

5-(3,5-Dichlorophenyl)-1-(4-isopropoxyphenyl)-1H-indole-2-carboxylic acid (a) 5-(3,5-Dichlorophenyl)-1H-indole-2-carboxylic acid ethyl ester To a stirred solution of 5-bromo-3-chloro-1H-indole-2-carboxylic acid ethyl ester (500 mg, 1.86 mmol) and 3,5-dichlorophenyl boronic acid (530 mg, 2.78 mmol) in a mixture of MeCN (26 mL) and i-PrOH (3.3 mL) at room temperature under argon, was added Pd(OAc)$_2$ (12 mg, 0.05 mmol), Ph$_3$P (40 mg, 0.15 mmol) and Na$_2$CO$_3$ (2M aq., 16 mL) and the resulting mixture was heated at reflux for 3 h. After cooling to room temperature the reaction was diluted with water (20 mL) and extracted with EtOAc (3×30 mL). The combined organic extracts were washed with water, brine and dried (MgSO$_4$). Solvent removal and purification by chromatography afforded the sub-title compound (430 mg, 69%).

(b) 5-(3.5-Dichlorophenyl)-1-(4-isopropoxyphenyl)-1H-indole-2-carboxylic acid

The title compound was prepared in accordance with Example 8(c) from 5-(3,5-dichlorophenyl)-1H-indole-2-carboxylic acid ethyl ester (see step (a) above) and 4-isopropoxyphenylboronic acid, followed by ester hydrolysis in accordance with the procedure described in Example 35, Method 3, step (b).

200 MHz $^1$H-NMR (DMSO-$d_6$, ppm) δ 12.86-12.80 (1H, br s) 8.15-8.10 (1H, m) 7.75-7.71 (2H, m) 7.67-7.59 (1H, m) 7.57-7.53 (1H, m) 7.42-7.38 (1H, m) 7.12-6.99 (3H, m) 4.68 (1H, septet, J=5.9 Hz) 1.32 (6H, d, J=5.9 Hz).

Example 55

5-(2,4-Dichlorophenyl)-1-(4-isopropoxyphenyl)-1H-indole-2-carboxylic acid

The title compound was prepared in accordance with Example 54 from 5-bromo-3-chloro-1H-indole-2-carboxylic acid ethyl ester, 2,4-dichlorophenyl boronic acid and 4-isopropoxyphenyl boronic acid, followed by ester hydrolysis.

200 MHz $^1$H-NMR (DMSO-$d_6$, ppm) δ 12.69 (1H, bs) 7.80-7.68 (2H, m) 7.55-7.39 (3H, m) 7.35-7.22 (3H, m) 7.11-6.98 (3H, m) 4.68 (1H, septet, J=5.9 Hz) 1.32 (6H, d, J=5.9 Hz).

Example 56

5-(4-tert-Butylphenyl)-1-(4-cyclopentoxyphenyl)-1H-indole-2-carboxylic acid

The title compound was prepared in accordance with Example 1(b) from 5-(4-tert-butylphenyl)indole-2-carboxylic acid ethyl ester (see Example 1(a)) and 1-bromo-4-cyclopentoxybenzene (see Example 48(a)), followed by ester hydrolysis in accordance with the procedure described in Example 35, Method 3, step (b).

200 MHz $^1$H-NMR (DMSO-$d_6$, ppm) δ 12.77 (1H, s) 7.96 (1H, d, J=1.1 Hz) 7.60-7.50 (3H, m) 7.46-7.40 (3H, m) 7.28-7.20 (2H, m) 7.07-6.98 (3H, m) 4.90-4.82 (1H, m) 2.01-1.55 (8H, m) 1.29 (9H, s).

Example 57

5-(4-tert-Butylphenyl)-1-(5-cyclopentylaminopyrid-2-yl)-1H-indole-2-carboxylic acid sodium salt The title compound was prepared in accordance with Example 1(b) from 5-(4-tert-butylphenyl)indole-2-carboxylic acid ethyl ester (see Example 1(a)) and 6-bromopyrid-3-yl)cyclopentylamine (see Example 45(b)), followed by ester hydrolysis in accordance with Example 45(d).

200 MHz $^1$H-NMR (DMSO-$d_6$, ppm) δ 7.81-7.74 (2H, m) 7.59-7.54 (2H, m) 7.44-7.39 (2H, m) 7.31 (1H, dd, J=8.6, 1.5 Hz) 7.17 (1H, d, J=8.6 Hz) 6.98-6.97 (2H, m) 6.72 (1H, s) 5.89 (1H, d, J=6.4 Hz) 3.80-3.65 (1H, m) 1.99-1.89 (2H, m) 1.74-1.43 (6H, m) 1.29 (9H, s).

Example 58

5-(4-tert-Butylphenyl)-1-(6-cyclopentoxypyrid-3-yl)-1H-indole-2-carboxylic acid

The title compound was prepared in accordance with Example 1(b) from 5-(4-tert-butylphenyl)indole-2-carboxylic acid ethyl ester (see Example 1(a)) and 5-bromo-2-cyclopentoxypyridine (see Example 36(b)), followed by ester hydrolysis in accordance with the procedure described in Example 35, Method 3, step (b).

200 MHz $^1$H-NMR (DMSO-$d_6$, ppm) δ 12.95-12.80 (1H, br s) 8.20-8.19 (1H, m) 8.00-7.99 (1H, m) 7.77-7.71 (1H, m) 7.62-7.56 (3H, m) 7.49-7.45 (3H, m) 7.12-7.07 (1H, m) 6.90 (1H, d, J=8.8 Hz) 5.48-5.39 (1H, m) 2.05-1.61 (8H, m) 1.31 (9H, s).

Example 59

5-(4-tert-Butylphenyl)-1-(4-cyclopentoxy-3-nitrophenyl)-1H-indole-2-carboxylic acid (a) 4-Bromo-1-cyclopentoxy-2-nitrobenzene To a mixture of 4-bromo-2-nitrophenol (1.0 g, 4.6 mmol), cyclopentanol (600 mg, 7.0 mmol) and Ph$_3$P (1.47 g, 5.6 mmol) in THF (50 mL) at 0° C. was portion-wise added diisopropylazodicarboxylate (1.52 g, 7.5 mmol) in THF (10 mL) and the resulting mixture was left to stir overnight at ambient temperature. Solvent removal and purification by chromatography on silica gel afforded the sub-title compound (1.24 g, 94%).

(b) 5-(4-tert-Butylphenyl)-1-(4-cyclopentoxy-3-nitrophenyl)-1H-indole-2-carboxylic acid The title compound was prepared in accordance with Example 1(b) from 5-(4-tert-butylphenyl)indole-2-carboxylic acid ethyl ester (see Example 1(a)) and 4-bromo-1-cyclopentoxy-2-nitrobenzene (see step (a) above), followed by ester hydrolysis in accordance with the procedure described in Example 35, Method 3, step (b).

200 MHz $^1$H-NMR (DMSO-$d_6$, ppm) δ 7.91-7.85 (2H, m) 7.61-7.39 (7H, m) 7.15-7.08 (2H, m) 5.15-5.07 (1H, m) 1.98-1.61 (8H, m) 1.31 (9H, s).

Example 60

5-(4-tert-Butylphenyl-1-(4-isopropoxy-3-nitro-phenyl)-1H-indole-2-carboxylic acid (a) 4-Bromo-1-isopropoxy-2-nitrobenzene A mixture of 4-bromo-2-nitrophenol (2.17 g, 10 mmol), 2-bromopropane (2.44 g, 20 mmol), KOH (2.24 g, 40 mmol) and 18-crown-6 (224 mg, 1.0 mmol) in benzene (100 mL) was heated at reflux for 4 h. Cooling to room temperature, concentration and purification by chromatography afforded the sub-title compound (1.59 g, 61%).

(b) 5-(4-tert-Butylphenyl)-1-(4-isopropoxy-3-nitrophenyl)-1H-indole-2-carboxylic acid The title compound was prepared in accordance with Example 1(b) from 5-(4-tert-butylphenyl)indole-2-carboxylic acid ethyl ester (see Example 1(a)) and 4-bromo-1-isopropoxy-2-nitrobenzene (see step (a) above), followed by ester hydrolysis in accordance with the procedure described in Example 35, Method 3, step (b).

200 MHz $^1$H-NMR (DMSO-$d_6$, ppm) δ 13.1-12.8 (1H, br s) 8.01-7.95 (2H, m) 7.69-7.44 (8H, m) 7.15 (1H, d, J=8.8 Hz) 4.91 (1H, septet, J=6.0 Hz) 1.35 (6H, d, J=6.0 Hz) 1.30 (9H, s).

Example 61

5-(4-tert-Butylphenyl)-1-quinolin-3-yl-1H-indole-2-carboxylic acid

The title compound was prepared in accordance with Example 8(c) from 5-(4-tert-butylphenyl)indole-2-carboxylic acid ethyl ester (see Example 1(a)) and quinoline-3-boronic acid, followed by ester hydrolysis in accordance with the procedure described in Example 35, Method 3, step (b).

200 MHz $^1$H-NMR (DMSO-$d_6$, ppm) δ 13.05 (1H, s) 8.90 (1H, d, J=2.5 Hz) 8.58 (1H, d, J=2.4 Hz) 8.18-8.07 (3H, m) 7.92-7.84 (1H, m) 7.77-7.69 (1H, m) 7.64-7.57 (4H, m) 7.51-7.46 (2H, m) 7.23 (1H, d, J=8.8 Hz) 1.32 (9H, s).

Example 62

5-(4-tert-Butylphenyl)-1-(4-chlorophenyl)-1H-indole-2-carboxylic acid

The title compound was prepared in accordance with Example 8(c) from 5-(4-tert-butylphenyl)indole-2-carboxylic acid ethyl ester (see Example 1(a)) and 4-chlorophenylboronic acid, followed by ester hydrolysis in accordance with the procedure described in Example 35, Method 3, step (b).

200 MHz $^1$H-NMR (DMSO-$d_6$, ppm) δ 12.94-12.87 (1H, br s) 8.03-7.98 (1H, m) 7.66-7.54 (5H, m) 7.53-7.41 (5H, m) 7.17-7.08 (1H, m) 1.36-1.28 (9H, m).

Example 63

5-(4-tert-Butylphenyl)-1-(3,5-dichlorophenyl)-1H-indole-2-carboxylic acid

The title compound was prepared in accordance with Example 8(c) from 5-(4-tert-butylphenyl)indole-2-carboxylic acid ethyl ester (see Example 1(a)) and 3,5-dichlorophenylboronic acid, followed by ester hydrolysis in accordance with the procedure described in Example 35, Method 3, step (b).

200 MHz $^1$H-NMR (DMSO-$d_6$, ppm) δ 13.02-12.96 (1H, br s) 8.03-7.99 (1H, m) 7.78-7.754 (1H, m) 7.65-7.56 (5H, m) 7.52-7.43 (3H, m) 7.21-7.14 (1H, m) 1.34-1.27 (9H, m).

Example 64

5-(4-tert-Butylphenyl)-1-(4-cyclohexylphenyl)-1H-indole-2-carboxylic acid

The title compound was prepared in accordance with Example 8(c) from 5-(4-tert-butylphenyl)indole-2-carboxylic acid ethyl ester (see Example 1(a)) and 4-cyclohexanephenylboronic acid, followed by ester hydrolysis in accordance with the procedure described in Example 35, Method 3, step (b).

200 MHz $^1$H-NMR (DMSO-$d_6$, ppm) δ 12.8-12.7 (1H, br s) 7.99-7.96 (1H, m) 7.60-7.41 (6H, m) 7.40-7.33 (2H, m) 7.30-7.24 (2H, m) 7.06 (1H, d, J=8.8 Hz) 2.67-2.52 (1H, m, overlapped with DMSO signal) 1.95-1.16 (10H, m) 1.30 (9H, s).

Example 65

Title compounds of the examples were tested in the biological test described above and were found to exhibit 50% inhibition of mPGES-1 at a concentration of 10 μM or below. For example, for the following compounds of the examples, 50% inhibition was observed at:

Example 1: 62 nM

Example 9: 610 nM

Example 33: 390 nM

Example 36: 1100 nM

Example 64: 170 nM

The invention claimed is:
1. A compound of formula I,

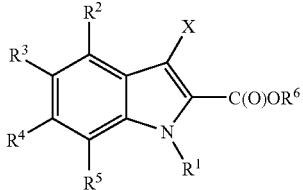

wherein
X represents H or a halo group;
$R^1$ represents a phenyl group optionally substituted by one or more substituents selected from A;
one of the groups $R^2$, $R^3$, $R^4$ and $R^5$ represents an aryl group or a heteroaryl group (both of which are optionally substituted by one or more substituents selected from A) and:
a) the other groups are independently selected from hydrogen, $G^1$, an aryl group, a heteroaryl group (which latter two groups are optionally substituted by one or more substituents selected from A), $C_{1-8}$ alkyl and a heterocycloalkyl group (which latter two groups are optionally substituted by one or more substituents selected from $G^1$ and $Z^1$); and/or
b) any two other groups which are adjacent to each other are optionally linked to form, along with two atoms of the essential benzene ring in the compound of formula I, a 3- to 8-membered ring, optionally containing 1 to 3 heteroatoms and/or 1 to 3 double bonds, which ring is itself optionally substituted by one or more substituents selected from halo, —$R^6$, —$OR^6$ and =O;
A represents, on each occasion when mentioned above:
I) an aryl group or a heteroaryl group, both of which are optionally substituted by one or more substituents selected from B;
II) $C_{1-8}$ alkyl or a heterocycloalkyl group, both of which are optionally substituted by one or more substituents selected from $G^1$ and $Z^1$;
III) a $G^1$ group; or
IV) two A substituents may be linked together to form, along with at least two atoms of the aryl or heteroaryl group to which the two A substituents are attached, a further 3- to 5-membered ring, which ring optionally contains 1 to 3 heteroatoms and/or 1 to 2 double bonds, and which is optionally substituted by halo or $C_{1-8}$ alkyl, which latter group is optionally substituted by halo;
$R^6$ represents, on each occasion when mentioned above:
I) hydrogen; or
II) $C_{1-8}$ alkyl group optionally substituted by one or more substituents selected from $G^1$ and $Z^1$;
$G^1$ represents, on each occasion when mentioned above, halo, cyano, —$N_3$, —$NO_2$, —$ONO_2$, or -$A^1$-$R^7$;
wherein
$A^1$ represents a single bond or a spacer group selected from —C(O)$A^2$-, —S(O)$_n A^3$-, —N($R^8$)$A^4$- and —O$A^5$- in which:
$A^2$ and $A^3$ independently represent a single bond, —O—, —N($R^8$)— or —C(O)—;
$A^4$ and $A^5$ independently represent a single bond, —C(O)—, —C(O)N($R^8$)—, —C(O)O—, —S(O)$_n$— or —S(O)$_n$N($R^8$)—;

$Z^1$ represents, on each occasion when mentioned above, =O, =S, =NO$R^7$, =NS(O)$_n$N($R^8$)($R^7$), =NCN or =C(H)NO$_2$;
B represents, on each occasion when mentioned above:
I) an aryl group or a heteroaryl group, both of which are optionally substituted by one or more substituents selected from $G^2$, methylenedioxy, difluoromethylenedioxy and dimethylmethylenedioxy;
II) $C_{1-8}$ alkyl or a heterocycloalkyl group, both of which are optionally substituted by one or more substituents selected from $G^2$ and $Z^2$;
III) a $G^2$ group; or
IV) methylenedioxy, difluoromethylenedioxy or dimethylmethylenedioxy;
$G^2$ represents, on each occasion when mentioned above, halo, cyano, —$N_3$, —$NO_2$, —$ONO_2$ or -$A^6$-$R^9$;
wherein
$A^6$ represents a single bond or a spacer group selected from —C(O)$A^7$, —S(O)$_n A^8$-, —N($R^{10}$)$A^9$- and —O$A^{10}$-, in which:
$A^7$ and $A^8$ independently represent a single bond, —O—, —N($R^{10}$)— or —C(O)—;
$A^9$ and $A^{10}$ independently represent a single bond, —C(O)—, —C(O)N($R^{10}$)—, —C(O)O—, —S(O)$_n$— or —S(O)$_n$N($R^{10}$)—;
$Z^2$ represents, on each occasion when mentioned above, =O, =S, =NO$R^9$, =NS(O)$_n$N($R^{10}$)($R^9$), =NCN or =C(H)NO$_2$;
$R^7$, $R^8$, $R^9$ and $R^{10}$ are independently selected from:
i) hydrogen;
ii) an aryl group or a heteroaryl group, both of which are optionally substituted by one or more substituents selected from $G^3$, methylenedioxy, difluoromethylenedioxy and dimethylmethylenedioxy; and
iii) $C_{1-8}$ alkyl or a heterocycloalkyl group, both of which are optionally substituted by $G^3$ and/or $Z^3$; or
any pair of $R^7$ and $R^8$, or $R^9$ and $R^{10}$, may, when present on the same or on adjacent atoms, be linked together to form a further 3- to 8-membered ring, optionally containing 1 to 3 heteroatoms and/or 1 to 3 double bonds, which ring is optionally substituted by one or more substituents selected from $G^3$ and $Z^3$;
$G^3$ represents, on each occasion when mentioned above, halo, cyano, —$N_3$, —$NO_2$, —$ONO_2$ or -$A^{11}$-$R^{11}$;
wherein
$A^{11}$ represents a single bond or a spacer group selected from —C(O)$A^{12}$-, —S(O)$_n A^{13}$-, —N($R^{12}$)$A^{14}$- and —O$A^{15}$-, in which:
$A^{12}$ and $A^{13}$ independently represent a single bond, —O—, —(N$R^{12}$)— or —C(O)—;
$A^{14}$ and $A^{15}$ independently represent a single bond, —C(O)—, —C(O)N($R^{12}$)—, —C(O)O—, —S(O)$_n$— or —S(O)$_n$N($R^{12}$)—;
$Z^3$ represents, on each occasion when mentioned above, =O, =S, =NO$R^{11}$, =NS(O)$_n$N($R^{12}$)($R^{11}$), =NCN or =C(H)NO$_2$;
n represents, on each occasion when mentioned above, 1 or 2;
$R^{11}$ and $R^{12}$ are independently selected from:
i) hydrogen;
ii) $C_{1-6}$ alkyl or a heterocycloalkyl group, both of which groups are optionally substituted by one or more substituents selected from halo, $C_{1-4}$ alkyl, —N($R^{13}$)($R^{14}$), —O($R^{13}$) and =O; and
iii) an aryl or heteroaryl group, both of which are optionally substituted by one or more substituents selected from halo, $C_{1-4}$ alkyl, —N($R^{13}$)($R^{14}$) and —O($R^{13}$); or any pair $R^{11}$ and $R^{12}$ may, when present on the same or on adjacent atoms, be linked together to form a further 3- to 8-membered ring, optionally containing 1 to 3 heteroatoms and/or 1 to 3 double bonds, which ring is optionally substituted by one or more substituents selected from halo, $C_{1-4}$ alkyl, —$N(R^{13})(R^{14})$, —$O(R^{13})$ and =O;

$R^{13}$ and $R^{14}$ are independently selected from hydrogen and $C_{1-4}$ alkyl, which latter group is optionally substituted by one or more halo groups;

or a pharmaceutically-acceptable salt thereof, provided that, when $R^2$, $R^4$ and $R^5$ all represent H, $R^3$ represents unsubstituted phenyl, $R^6$ represents ethyl, and X represents H or Cl, then $R^1$ does not represent 2,4-dinitrophenyl.

2. A compound as claimed in claim 1, wherein:

$A^2$ and $A^3$ independently represent a single bond, —O— or —$N(R^8)$—;

$Z^1$ represents, on each occasion when mentioned above, =O, =$NOR^7$, =$NS(O)_nN(R^8)(R^7)$, =NCN or =C(H)NO$_2$;

$A^7$ and $A^8$ independently represent a single bond, —O— or —$N(R^{10})$—;

$Z^2$ represents, on each occasion when mentioned above, =O, =$NOR^9$, =$NS(O)_nN(R^{10})(R^9)$, —NCN or =C(H)NO$_2$;

$A^{12}$ and $A^{13}$ independently represent a single bond, —O— or —$N(R^{12})$—; and $Z^3$ represents, on each occasion when mentioned above, =O, =$NOR^{11}$, =$NS(O)_nN(R^{12})(R^{11})$, =NCN or =C(H)NO$_2$.

3. A compound as claimed in claim 1 or claim 2, wherein X represents H, Cl or Br.

4. A compound as claimed in claim 1, wherein n represents 2.

5. A compound as claimed in claim 1, wherein A represents $G^1$.

6. A compound as claimed in claim 1, wherein $G^1$ represents cyano, halo, —NO$_2$ or -$A^1$-$R^7$.

7. A compound as claimed in claim 6, wherein $G^1$ represents —NO$_2$ or -$A^1$-$R^7$.

8. A compound as claimed in claim 1, wherein $A^1$ represents —C(O)$A^2$-, a single bond, —$S(O)_2A^3$, —$N(R^8)A^4$- or —$OA^5$-.

9. A compound as claimed in claim 8, wherein $A^1$ represents a single bond, —$S(O)_2A^3$, —$N(R^8)A^4$- or —$OA^5$-.

10. A compound as claimed in claim 1, wherein $A^2$ represents —$N(R^8)$—.

11. A compound as claimed in claim 1, wherein $A^4$ represents a single bond or —C(O)—.

12. A compound as claimed in claim 1, wherein $A^3$ and $A^5$ independently represent a single bond.

13. A compound as claimed in claim 1, wherein $R^7$ represents hydrogen, $C_{1-6}$ alkyl or a heterocycloalkyl group, which latter two groups are optionally substituted by one or more substituents selected from $G^3$.

14. A compound as claimed in claim 1, wherein $R^8$ represents hydrogen or $C_{1-6}$ alkyl, which latter group is optionally substituted by one or more substituents selected from $G^3$.

15. A compound as claimed in claim 1, wherein $G^3$ represents halo or -$A^{11}$-$R^{11}$.

16. A compound as claimed in claim 1, wherein $A^{11}$ represents a single bond, —C(O)$A^{12}$-, —$N(R^{12})$— or —O—.

17. A compound as claimed in claim 1, wherein $A^{12}$ represents —O— or —$N(R^{12})$—.

18. A compound as claimed in claim 1, wherein $R^{11}$ represents hydrogen or $C_{1-3}$ alkyl, or $R^{11}$ and $R^{12}$ are linked to form a 5- to 6-membered ring optionally containing one further heteroatom, which ring is optionally substituted by a $C_{1-3}$ alkyl group.

19. A compound as claimed in claim 1, wherein $R^1$ represents phenyl.

20. A compound as claimed in claim 1, wherein $R^2$ represents $G^1$ or hydrogen.

21. A compound as claimed in claim 20, wherein $R^2$ represents hydrogen.

22. A compound as claimed in claim 1, wherein $R^3$ and $R^4$ independently represent $G^1$, hydrogen or an optionally substituted phenyl, pyrimidinyl or pyridyl group.

23. A compound as claimed in claim 22, wherein $R^3$ and $R^4$ independently represent hydrogen or an optionally substituted phenyl or pyridyl group.

24. A compound as claimed in claim 1, wherein at least one of $R^3$ and $R^4$ represents optionally substituted aryl or heteroaryl, and up to one other represents $G^1$ or hydrogen.

25. A compound as claimed in claim 22, wherein when $R^3$ or $R^4$ represents an optionally substituted phenyl, pyridyl or pyrimidinyl group, then the other substituents $R^2$, $R^5$ and $R^3$ or $R^4$ on the essential benzene ring of the indole of formula I independently represent H or $G^1$.

26. A compound as claimed in claim 22, wherein the optional substituents are selected from cyano, —$C(O)N(R^{15})R^{16}$, heterocycloalkyl optionally containing one or more unsaturations and optionally substituted by one or more halo or $C_{1-3}$ alkyl groups, heteroaryl optionally substituted by one or more halo or $C_{1-3}$ alkyl groups, —NO$_2$, halo, $C_{1-6}$ alkyl (which alkyl group may be linear or branched, cyclic, part-cyclic, or unsaturated and/or optionally substituted with one or more groups selected from halo, —$C(O)OR^{15}$ and —$OR^{15}$), —$OR^{15}$, —$N(R^{15})R^{16}$ and —$S(O)_2R^{15}$, wherein $R^{15}$ and $R^{16}$ independently represent H, a heterocycloalkyl group optionally substituted by one or more $C_{1-4}$ alkyl groups, or $C_{1-6}$ alkyl, which alkyl group is optionally substituted by one or more substituents selected from halo, —$OR^{17}$, —$N(R^{18})R^{19}$, —$C(O)OR^{17}$ and —$C(O)N(R^{18})R^{19}$, wherein $R^{17}$, $R^{18}$ and $R^{19}$ independently represent H, $C_{1-6}$ alkyl, which alkyl groups are optionally substituted by one or more halo groups, or $R^{18}$ and $R^{19}$ are linked to form a 4- to 8-membered ring optionally containing a further 1 to 2 heteroatoms, which ring is optionally substituted by a $C_{1-3}$ alkyl group.

27. A compound as claimed in claim 26, wherein the optional substituents are selected from —NO$_2$, halo, $C_{1-6}$ alkyl (which alkyl group may be linear or branched, cyclic, part-cyclic or unsaturated and/or optionally substituted with one or more groups selected from halo, —$C(O)OR^{15}$ and —$OR^{15}$), —$OR^{15}$, —$N(R^{15})R^{16}$ and —$S(O)_2R^{15}$, wherein $R^{15}$ and $R^{16}$ independently represent, H, a heterocycloalkyl group optionally substituted by one or more $C_{1-4}$ alkyl groups, or $C_{1-6}$ alkyl, which alkyl group is optionally substituted by one or more substituents selected from halo, —$OR^{17}$, —$N(R^{18})R^{19}$, —$C(O)OR^{17}$ and —$C(O)N(R^{18})R^{19}$, wherein $R^{17}$, $R^{18}$ and $R^{19}$ independently represent H, $C_{1-6}$ alkyl, which alkyl groups are optionally substituted by one or more halo groups, or $R^{18}$ and $R^{19}$ are linked to form a 4- to 8-membered ring optionally containing a further 1 to 2 heteroatoms, which ring is optionally substituted by a $C_{1-3}$ alkyl group.

28. A pharmaceutical formulation comprising a compound of formula I,

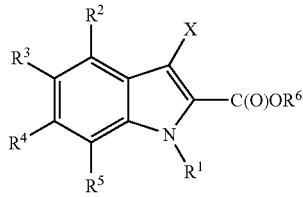

wherein
X represents H or a halo group;
R$^1$ represents a phenyl group optionally substituted by one or more substituents selected from A;
one of the groups R$^2$, R$^3$, R$^4$ and R$^5$ represents an aryl group or a heteroaryl group (both of which are optionally substituted by one or more substituents selected from A) and:
a) the other groups are independently selected from hydrogen, G$^1$, an aryl group, a heteroaryl group (which latter two groups are optionally substituted by one or more substituents selected from A), C$_{1-8}$ alkyl and a heterocycloalkyl group (which latter two groups are optionally substituted by one or more substituents selected from G$^1$ and Z$^1$); and/or
b) any two other groups which are adjacent to each other are optionally linked to form, along with two atoms of the essential benzene ring in the compound of formula I, a 3- to 8-membered ring, optionally containing 1 to 3 heteroatoms and/or 1 to 3 double bonds, which ring is itself optionally substituted by one or more substituents selected from halo, —R$^6$, —OR$^6$ and =O;
A represents, on each occasion when mentioned above:
I) an aryl group or a heteroaryl group, both of which are optionally substituted by one or more substituents selected from B;
II) C$_{1-8}$ alkyl or a heterocycloalkyl group, both of which are optionally substituted by one or more substituents selected from G$^1$ and Z$^1$;
III) a G$^1$ group; or
IV) two A substituents may be linked together to form, along with at least two atoms of the aryl or heteroaryl group to which the two A substituents are attached, a further 3- to 5-membered ring, which ring optionally contains 1 to 3 heteroatoms and/or 1 to 2 double bonds, and which is optionally substituted by halo or C$_{1-8}$ alkyl, which latter group is optionally substituted by halo;
R$^6$ represents, on each occasion when mentioned above:
I) hydrogen; or
II) C$_{1-8}$ alkyl group optionally substituted by one or more substituents selected from G$^1$ and Z$^1$;
G$^1$ represents, on each occasion when mentioned above, halo, cyano, —N$_3$, —NO$_2$, —ONO$_2$, or -A$^1$-R$^7$;
wherein
A$^1$ represents a single bond or a spacer group selected from —C(O)A$^2$-, —S(O)$_n$A$^3$-, —N(R$^8$)A$^4$- and —OA$^5$- in which:
A$^2$ and A$^3$ independently represent a single bond, —O—, —N(R$^8$)— or —C(O)—;
A$^4$ and A$^5$ independently represent a single bond, —C(O)—, —C(O)N(R$^8$)—, —C(O)O—, —S(O)$_n$— or —S(O)$_n$N(R$^9$)—;

Z$^1$ represents, on each occasion when mentioned above, =O, =S, =NOR$^7$, =NS(O)$_n$N(R$^8$)(R$^7$), =NCN or =C(H)NO$_2$;
B represents, on each occasion when mentioned above:
I) an aryl group or a heteroaryl group, both of which are optionally substituted by one or more substituents selected from G$^2$, methylenedioxy, difluoromethylenedioxy and dimethylmethylenedioxy;
II) C$_{1-8}$ alkyl or a heterocycloalkyl group, both of which are optionally substituted by one or more substituents selected from G$^2$ and Z$^2$; III) a G$^2$ group; or
IV) methylenedioxy, difluoromethylenedioxy or dimethylmethylenedioxy;
G$^2$ represents, on each occasion when mentioned above, halo, cyano, —N$_3$, —NO$_2$, —ONO$_2$ or -A$^6$-R$^9$;
wherein
A$^6$ represents a single bond or a spacer group selected from —C(O)A$^7$-, —S(O)$_n$A$^8$-, —N(R$^{10}$)A$^9$- and —OA$^{10}$-, in which:
A$^7$ and A$^8$ independently represent a single bond, —O—, —N(R$^{10}$)— or —C(O)—;
A$^9$ and A$^{10}$ independently represent a single bond, —C(O)—, —C(O)N(R$^{10}$)—, —C(O)O—, —S(O)$_n$— or —S(O)$_n$N(R$^{10}$)—;
Z$^2$ represents, on each occasion when mentioned above, =O, =S, =NOR$^9$, =NS(O)$_n$N(R$^{10}$)(R$^9$), =NCN or =C(H)NO$_2$;
R$^7$, R$^8$, R$^9$ and R$^{10}$ are independently selected from:
i) hydrogen;
ii) an aryl group or a heteroaryl group, both of which are optionally substituted by one or more substituents selected from G$^3$, methylenedioxy, difluoromethylenedioxy and dimethylmethylenedioxy; and
iii) C$_{1-8}$ alkyl or a heterocycloalkyl group, both of which are optionally substituted by G$^3$ and/or Z$^3$; or
any pair of R$^7$ and R$^8$, or R$^9$ and R$^{10}$, may, when present on the same or on adjacent atoms, be linked together to form a further 3- to 8-membered ring, optionally containing 1 to 3 heteroatoms and/or 1 to 3 double bonds, which ring is optionally substituted by one or more substituents selected from G$^3$ and Z$^3$;
G$^3$ represents, on each occasion when mentioned above, halo, cyano, —N$_3$, —NO$_2$, —ONO$_2$ or -A$^{11}$-R$^{11}$;
wherein
A$^{11}$ represents a single bond or a spacer group selected from —C(O)A$^{12}$-, —S(O)$_n$A$^{13}$-, —N(R$^{12}$)A$^{14}$- and —OA$^{15}$-, in which:
A$^{12}$ and A$^{13}$ independently represent a single bond, —O—, —(NR$^{12}$)— or —C(O)—;
A$^{14}$ and A$^{15}$ independently represent a single bond, —C(O)—, —C(O)N(R$^{12}$)—, —C(O)O—, —S(O)$_n$— or
Z$^3$ represents, on each occasion when mentioned above, =O, =S, =NOR$^{11}$, =NS(O)$_n$N(R$^{12}$)(R$^{11}$), =NCN or =C(H)NO$_2$;
n represents, on each occasion when mentioned above, 1 or 2;
R$^{11}$ and R$^{12}$ are independently selected from:
i) hydrogen;
ii) C$_{1-6}$ alkyl or a heterocycloalkyl group, both of which groups are optionally substituted by one or more substituents selected from halo, C$_{1-4}$ alkyl, —N(R$^{13}$)(R$^{14}$), —O(R$^{13}$) and =O; and
iii) an aryl or heteroaryl group, both of which are optionally substituted by one or more substituents selected from halo, C$_{1-4}$ alkyl, —N(R$^{13}$)(R$^{14}$) and —O(R$^{13}$); or any pair $R^{11}$ and $R^{12}$ may, when present on the same or on adjacent atoms, be linked together to form a further 3- to 8-membered ring, optionally containing 1 to 3 heteroatoms and/or 1 to 3 double bonds, which ring is optionally substituted by one or more substituents selected from halo, $C_{1-4}$ alkyl, —N($R^{13}$)($R^{14}$), —O($R^{13}$) and =O;

$R^{13}$ and $R^{14}$ are independently selected from hydrogen and $C_{1-4}$ alkyl, which latter group is optionally substituted by one or more halo groups;

or a pharmaceutically-acceptable salt thereof, in admixture with a pharmaceutically acceptable adjuvant, diluent or carrier.

29. A combination product comprising:
a compound of formula I,

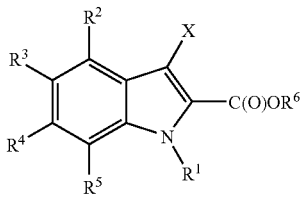

wherein
X represents H or a halo group;
$R^1$ represents a phenyl group optionally substituted by one or more substituents selected from A;
one of the groups $R^2$, $R^3$, $R^4$ and $R^5$ represents an aryl group or a heteroaryl group (both of which are optionally substituted by one or more substituents selected from A) and:
a) the other groups are independently selected from hydrogen, $G^1$, an aryl group, a heteroaryl group (which latter two groups are optionally substituted by one or more substituents selected from A), $C_{1-8}$ alkyl and a heterocycloalkyl group (which latter two groups are optionally substituted by one or more substituents selected from $G^1$ and $Z^1$); and/or
b) any two other groups which are adjacent to each other are optionally linked to form, along with two atoms of the essential benzene ring in the compound of formula I, a 3- to 8-membered ring, optionally containing 1 to 3 heteroatoms and/or 1 to 3 double bonds, which ring is itself optionally substituted by one or more substituents selected from halo, —$R^6$, —O$R^6$ and =O;

A represents, on each occasion when mentioned above:
I) an aryl group or a heteroaryl group, both of which are optionally substituted by one or more substituents selected from B;
II) $C_{1-8}$ alkyl or a heterocycloalkyl group, both of which are optionally substituted by one or more substituents selected from $G^1$ and $Z^1$; III) a $G^1$ group; or
IV) two A substituents may be linked together to form, along with at least two atoms of the aryl or heteroaryl group to which the two A substituents are attached, a further 3- to 5-membered ring, which ring optionally contains 1 to 3 heteroatoms and/or 1 to 2 double bonds, and which is optionally substituted by halo or $C_{1-8}$ alkyl, which latter group is optionally substituted by halo;

$R^6$ represents, on each occasion when mentioned above:
I) hydrogen; or
II) $C_{1-8}$ alkyl group optionally substituted by one or more substituents selected from $G^1$ and $Z^1$ $G^1$ represents, on each occasion when mentioned above, halo, cyano, —$N_3$, —$NO_2$, —$ONO_2$, or -$A^1$-$R^7$;
wherein
$A^1$ represents a single bond or a spacer group selected from —C(O)$A^2$-, —S(O)$_n A^3$-, —N($R^8$)$A^4$- and —O$A^5$- in which:
$A^2$ and $A^3$ independently represent a single bond, —O—, —N($R^8$)— or —C(O)—;
$A^4$ and $A^5$ independently represent a single bond, —C(O)—, —C(O)N($R^8$)—, —C(O)O—, —S(O)$_n$— or —S(O)$_n$N($R^8$)—;
$Z^1$ represents, on each occasion when mentioned above, =O, =S, =NO$R^7$, =NS(O)$_n$N($R^8$)($R^7$), =NCN or =C(H)NO$_2$;

B represents, on each occasion when mentioned above:
I) an aryl group or a heteroaryl group, both of which are optionally substituted by one or more substituents selected from $G^2$, methylenedioxy, difluoromethylenedioxy and dimethylmethylenedioxy;
II) $C_{1-8}$ alkyl or a heterocycloalkyl group, both of which are optionally substituted by one or more substituents selected from $G^2$ and $Z^2$; III) a $G^2$ group; or
IV) methylenedioxy, difluoromethylenedioxy or dimethylmethylenedioxy;

$G^2$ represents, on each occasion when mentioned above, halo, cyano, —$N_3$, —$NO_2$, —$ONO_2$ or -$A^6$-$R^9$;
wherein
$A^6$ represents a single bond or a spacer group selected from —C(O)$A^7$, —S(O)$_n A^8$-, —N($R^{10}$)$A^9$- and —O$A^{10}$-, in which:
$A^7$ and $A^8$ independently represent a single bond, —O—, —N($R^{10}$)— or —C(O)—;
$A^9$ and $A^{10}$ independently represent a single bond, —C(O)—, —C(O)N($R^{10}$)—, —C(O)O—, —S(O)$_n$— or —S(O)$_n$N($R^{10}$)—;
$Z^2$ represents, on each occasion when mentioned above, =O, =S, =NO$R^9$, =NS(O)$_n$N($R^{10}$)($R^9$), =NCN or =C(H)NO$_2$;

$R^7$, $R^8$, $R^9$ and $R^{10}$ are independently selected from:
i) hydrogen;
ii) an aryl group or a heteroaryl group, both of which are optionally substituted by one or more substituents selected from $G^3$, methylenedioxy, difluoromethylenedioxy and dimethylmethylenedioxy; and
iii) $C_{1-8}$ alkyl or a heterocycloalkyl group, both of which are optionally substituted by $G^3$ and/or $Z^3$; or
any pair of $R^7$ and $R^8$, or $R^9$ and $R^{10}$, may, when present on the same or on adjacent atoms, be linked together to form a further 3- to 8-membered ring, optionally containing 1 to 3 heteroatoms and/or 1 to 3 double bonds, which ring is optionally substituted by one or more substituents selected from $G^3$ and $Z^3$;

$G^3$ represents, on each occasion when mentioned above, halo, cyano, —$N_3$, —$NO_2$, —$ONO_2$ or -$A^{11}$-$R^{11}$;
wherein
$A^{11}$ represents a single bond or a spacer group selected from —C(O)$A^{12}$-, —S(O)$_n A^{13}$-, —N($R^{12}$)$A^{14}$- and —O$A^{15}$-, in which:
$A^{12}$ and $A^{13}$ independently represent a single bond, —O—, —(N$R^{12}$)— or —C(O)—;
$A^{14}$ and $A^{15}$ independently represent a single bond, —C(O)—, —C(O)N($R^{12}$)—, —C(O)O—, —S(O)$_n$— or —S(O)$_n$N($R^{12}$)—;
$Z^3$ represents, on each occasion when mentioned above, =O, =S, =NO$R^{11}$, =NS(O)$_n$N($R^{12}$)($R^{11}$), =NCN or =C(H)NO$_2$;

n represents, on each occasion when mentioned above, 1 or 2;

$R^{11}$ and $R^{12}$ are independently selected from:
i) hydrogen;
ii) $C_{1-6}$ alkyl or a heterocycloalkyl group, both of which groups are optionally substituted by one or more substituents selected from halo, $C_{1-4}$ alkyl, —$N(R^{13})(R^{14})$, —$O(R^{13})$ and =O; and
iii) an aryl or heteroaryl group, both of which are optionally substituted by one or more substituents selected from halo, $C_{1-4}$ alkyl, —$N(R^{13})(R^{14})$ and —$O(R^{13})$;

or any pair $R^{11}$ and $R^{12}$ may, when present on the same or on adjacent atoms, be linked together to form a further 3- to 8-membered ring, optionally containing 1 to 3 heteroatoms and/or 1 to 3 double bonds, which ring is optionally substituted by one or more substituents selected from halo, $C_{1-4}$ alkyl, —$N(R^{13})(R^{14})$, —$O(R^{13})$ and =O;

$R^{13}$ and $R^{14}$ are independently selected from hydrogen and $C_{1-4}$ alkyl, which latter group is optionally substituted by one or more halo groups;

or a pharmaceutically-acceptable salt thereof; and
another therapeutic agent that is useful in the treatment of inflammation, wherein each of the compound of formula I and the therapeutic agent is formulated in admixture with a pharmaceutically-acceptable adjuvant, diluent or carrier.

30. A combination product which comprises a kit of parts comprising:
(a) a pharmaceutical formulation as claimed in claim 28; and
(b) a pharmaceutical formulation comprising another therapeutic agent that is useful in the treatment of inflammation in admixture with a pharmaceutically-acceptable adjuvant, diluent or carrier,
which components (a) and (b) are each provided in a form that is suitable for administration in conjunction with the other.

31. A compound as claimed in claim 1, said compound being (3-chloro-1-(4-isopropoxyphenyl)-5-(5-trifluoromethylpyrid-2yl)-1H-indole-2-carboxylic acid).

* * * * *